(12) United States Patent
Smith et al.

(10) Patent No.: US 8,435,522 B2
(45) Date of Patent: May 7, 2013

(54) HUMANIZED ANTIBODIES AGAINST CXCR3

(75) Inventors: Rodger Smith, Jefferson, MD (US);
Palanisamy Kanakaraj, Germantown, MD (US); Viktor Roschke, Rockville, MD (US)

(73) Assignee: Teva Biopharmaceuticals USA, Inc., Rockville, MD (US)

( * ) Notice: Subject to any disclaimer, the term of this patent is extended or adjusted under 35 U.S.C. 154(b) by 670 days.

(21) Appl. No.: 12/449,222

(22) PCT Filed: Jan. 29, 2008

(86) PCT No.: PCT/US2008/052356
§ 371 (c)(1),
(2), (4) Date: Aug. 26, 2009

(87) PCT Pub. No.: WO2008/094942
PCT Pub. Date: Aug. 7, 2008

(65) Prior Publication Data
US 2010/0047238 A1    Feb. 25, 2010

Related U.S. Application Data

(60) Provisional application No. 60/898,709, filed on Feb. 1, 2007.

(51) Int. Cl.
*A61K 39/395* (2006.01)
*A61K 38/17* (2006.01)
*C07K 16/18* (2006.01)
*C12N 15/63* (2006.01)
*C12P 21/04* (2006.01)

(52) U.S. Cl.
USPC ............... 424/145.1; 424/134.1; 435/69.3; 435/320.1; 435/325; 530/387.3; 530/388.1; 530/391.3; 530/391.7

(58) Field of Classification Search .................. None
See application file for complete search history.

(56) References Cited

FOREIGN PATENT DOCUMENTS

WO    WO 01/72334 A2    10/2001
WO    WO 2005/030793 A2    4/2005

OTHER PUBLICATIONS

Paul, Fundamental Immunology, 3rd Edition, 1993, pp. 292-295.*
Casset et al (Biochemical and Biophysical Research Communications, 2003, 307:198-205.*
International Search Report for related International Patent Application No. PCT/US2008/052356, completed Sep. 29, 2008.
Written Opinion for related International Patent Application No. PCT/US2008/052356, completed Sep. 29, 2008.
Studnicka et al., "Human-engineered Monoclonal Antibodies Retain full Specific Binding Activity by Preserving non-CDR Complementarity-Modulating Residues," *Protein Engineering*, vol. 7, No. 6, pp. 805-814 (1994).
Roguska et al., "A comparison of Two Murine Monoclonal Antibodies Humanized by CDR-Grafting and Variable Domain Resurfacing," *Protein Engineering*, vol. 9, No. 10, pp. 895-904 (1996).
Jones et al., "Replacing the Complementarity-Determining Regions in a Human Antibody with Those from a Mouse," *Nature*, vol. 321, pp. 522-525 (1986).
International Preliminary Report on Patentability for PCT/US2008/052356 issued Aug. 4, 2009.

* cited by examiner

*Primary Examiner* — Bridget E Bunner
*Assistant Examiner* — Fozia Hamud
(74) *Attorney, Agent, or Firm* — Foley & Lardner LLP

(57) ABSTRACT

Disclosed are humanized antibodies that bind specifically to the receptor CXCR3. The humanized antibodies may be antagonists and may be used to treat or diagnose conditions associated with CXCR3 function.

25 Claims, 24 Drawing Sheets

```
                    EV.L.ESGGGLV.PGGSL.LSCAASGFTFS  Consensus #1
                    EVQLVESGGGLVQPGGSLRLSCAASGFTFS  Majority
                             10        20        30
   1    EVMLVESGGGLVKPGGSLKLSCAASGFTFS  V4407A Heavy/CXCR3
   1    EVQLVESGGGLVQPGGSLRLSCAASGFTFS  AAD53829
   1    EVQLLESGGGLVQPGGSLRLSCAASGFTFS  VH3-23 germ .YAMSWVRQ.P.K.LEWV..IS..GG.TYY  Consensus #1
                    SYAMSWVRQAPGKGLEWVSAISGSGGSTYY  Majority
                             40        50        60
  31    NYAMSWVRQTPEKRLEWVATISSGGYTYY   V4407A Heavy/CXCR3
  31    SYAMSWVRQAPGKGLEWVSAISGSGGSTYY  AAD53829
  31    SYAMSWVRQAPGKGLEWVSAISGSGGSTYY  VH3-23 germ .DS.KGRFTISRDN.KNTL.LQM.SLR.ED  Consensus #1
                    ADSVKGRFTISRDNSKNTLYLQMNSLRAED  Majority
                             70        80        90
  61    PDSLKGRFTISRDNAKNTLFLQMSSLRSED  V4407A Heavy/CXCR3
  61    ADSVKGRFTISRDNSKNTLYLQMNSLRAED  AAD53829
  61    ADSVKGRFTISRDNSKNTLYLQMNSLRAED  VH3-23 germ TAVYYC........................  Consensus #1
                    TAVYYCAKXXXXXXXXXXXYXXYXXDXWGQG Majority
                             100       110       120
  91    TAVYYCVRHGAPNTTWITYAPYYFDYWGQG  V4407A Heavy/CXCR3
  91    TAVYYCAKD-VLWVPAAPYYYYGMDVWGQG  AAD53829
  91    TAVYYCAK                        VH3-23 germ .......                         Consensus #1
                    TTXTVSS                         Majority 121    TTLTVSS                         V4407A Heavy/CXCR3
 120    TTVTVSS                         AAD53829
```

```
        Q X V L T Q S P A I M S A S P G E K V T M T C R A S S S V X   Majority
                    10              20              30
    1   E N V L T Q S P A I M S A L G E K V T M N C R A S S S V K   V3G6A Light
    1   Q I Q L T Q S P A I M S A S P G E K V T M T C R A S S S V S   CAC008834
    1   Q V V M T Q S P A F L S V T P G E K V T I T C Q A S E G I G   VBase-A14

-  X Y L Y W Y Q Q K S D A S P K L W I Y Y T S N L A S G V P   Majority
                    40              50              60
    31  -  -  Y M Y W Y Q Q K S D A S P K L W I Y Y T S N L A P G V P   V3G6A Light
    31  S S Y L H W Y Q Q K S G A S P K L W I Y S T S N L A S G V P   CAC008834
    31  -  N Y L Y W Y Q Q K P D Q A P R L L I K Y A S Q S I S G V P   VBase-A14

A R F S G S G S G T S Y S L T I S S X E A E D A A T Y Y C Q   Majority
                    70              80              90
    59  A R F S G S G S G N S Y S L T I S S M E G E D A A T Y Y C Q   V3G6A Light
    61  A R F S G S G S G T S Y S L T I S S V E A E D A A T Y Y C Q   CAC008834
    60  S R F S G S G S G T D F T F T I S S L E A E D A A T Y Y C Q   VBase-A14

Q X X X X P Y T F G G G T K L E I K                          Majority
                    100
    89  Q F T T S P Y T F G G G T K L E I K                          V3G6A Light
    91  Q Y S G Y P Y T F G G G T K L E I K                          CAC008834
    90  Q G N K H P                                                  VBase-A14
```

SEQUENCE LISTING

```
<160> NUMBER OF SEQ ID NOS: 83

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Met Ala Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ile Ser Ser Gly Gly Gly Tyr Thr Tyr Tyr Pro Asp Ser Leu Lys
1               5                   10                  15
Gly

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Asp or Tyr

<400> SEQUENCE: 3

His Gly Ala Pro Met Thr Thr Val Ile Thr Tyr Ala Pro Tyr Tyr Phe
1               5                   10                  15
```

Xaa Tyr

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Ser Ser Val Lys Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Thr Ser Asn Leu Ala Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Phe Thr Thr Ser Pro Tyr Thr
1               5

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gly Ala Pro Met Thr Thr Val Ile Thr Tyr Ala Pro Tyr Tyr Phe
1               5                   10                  15

Tyr Tyr

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Ile, Asn or Val
<220> FEATURE:
<221> NAME/KEY: MOD_RES
<222> LOCATION: (4)..(4)

```
<223> OTHER INFORMATION: Leu or Met
<220> FEATURE:
<221> NAME/KEY: MOD_RES
<222> LOCATION: (10)..(10)
<223> OTHER INFORMATION: Thr, Phe or Ile
<220> FEATURE:
<221> NAME/KEY: MOD_RES
<222> LOCATION: (11)..(11)
<223> OTHER INFORMATION: Leu or Met
<220> FEATURE:
<221> NAME/KEY: MOD_RES
<222> LOCATION: (13)..(13)
<223> OTHER INFORMATION: Leu, Ala or Val
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (18)..(18)
<223> OTHER INFORMATION: Arg or Lys
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (21)..(21)
<223> OTHER INFORMATION: Leu, Met or Ile
<220> FEATURE:
<221> NAME/KEY: MOD_RES
<222> LOCATION: (22)..(22)
<223> OTHER INFORMATION: Ser, Thr or Asn
<220> FEATURE:
<221> NAME/KEY: MOD_RES
<222> LOCATION: (39)..(39)
<223> OTHER INFORMATION: Ser or Pro
<220> FEATURE:
<221> NAME/KEY: MOD_RES
<222> LOCATION: (40)..(40)
<223> OTHER INFORMATION: Gly or Asp
<220> FEATURE:
<221> NAME/KEY: MOD_RES
<222> LOCATION: (41)..(41)
<223> OTHER INFORMATION: Gln or Ala
<220> FEATURE:
<221> NAME/KEY: MOD_RES
<222> LOCATION: (42)..(42)
<223> OTHER INFORMATION: Ala or Ser
<220> FEATURE:
<221> NAME/KEY: MOD_RES
<222> LOCATION: (44)..(44)
<223> OTHER INFORMATION: Arg or Lys
<220> FEATURE:
<221> NAME/KEY: MOD_RES
<222> LOCATION: (46)..(46)
<223> OTHER INFORMATION: Leu or Trp
<220> FEATURE:
<221> NAME/KEY: MOD_RES
<222> LOCATION: (48)..(48)
<223> OTHER INFORMATION: Tyr or Lys
<220> FEATURE:
<221> NAME/KEY: MOD_RES
<222> LOCATION: (57)..(57)
<223> OTHER INFORMATION: Ile or Val
<220> FEATURE:
<221> NAME/KEY: MOD_RES
<222> LOCATION: (59)..(59)
<223> OTHER INFORMATION: Ala or Ser
<220> FEATURE:
<221> NAME/KEY: MOD_RES
<222> LOCATION: (68)..(68)
<223> OTHER INFORMATION: Thr or Asn
<220> FEATURE:
<221> NAME/KEY: MOD_RES
<222> LOCATION: (69)..(69)
```

```
<223> OTHER INFORMATION: Asp or Ser
<220> FEATURE:
<221> NAME/KEY: MOD_RES
<222> LOCATION: (70)..(70)
<223> OTHER INFORMATION: Phe or Tyr
<220> FEATURE:
<221> NAME/KEY: MOD_RES
<222> LOCATION: (71)..(71)
<223> OTHER INFORMATION: Thr or Ser
<220> FEATURE:
<221> NAME/KEY: MOD_RES
<222> LOCATION: (72)..(72)
<223> OTHER INFORMATION: Leu or Phe
<220> FEATURE:
<221> NAME/KEY: MOD_RES
<222> LOCATION: (77)..(77)
<223> OTHER INFORMATION: Met or Leu
<220> FEATURE:
<221> NAME/KEY: MOD_RES
<222> LOCATION: (79)..(79)
<223> OTHER INFORMATION: Ala, Gly or Pro
<220> FEATURE:
<221> NAME/KEY: MOD_RES
<222> LOCATION: (82)..(82)
<223> OTHER INFORMATION: Phe or Ala
<220> FEATURE:
<221> NAME/KEY: MOD_RES
<222> LOCATION: (84)..(84)
<223> OTHER INFORMATION: Val or Thr
<220> FEATURE:
<221> NAME/KEY: MOD_RES
<222> LOCATION: (88)..(88)
<223> OTHER INFORMATION: Gln or Tyr
<220> FEATURE:
<221> NAME/KEY: MOD_RES
<222> LOCATION: (93)..(93)
<223> OTHER INFORMATION: Ser or Tyr

<400> SEQUENCE: 8

Xaa Xaa Val Xaa Thr Gln Ser Pro Ala Xaa Xaa Ser Xaa Xaa Xaa Gly
1               5                   10                  15

Glu Xaa Xaa Thr Xaa Xaa Cys Arg Ala Ser Ser Ser Val Lys Tyr Met
            20                  25                  30

Tyr Trp Tyr Gln Gln Lys Xaa Xaa Xaa Xaa Pro Xaa Leu Xaa Ile Xaa
        35                  40                  45

Tyr Thr Ser Asn Leu Ala Pro Gly Xaa Pro Xaa Arg Phe Ser Gly Ser
    50                  55                  60

Gly Ser Gly Xaa Xaa Xaa Xaa Thr Ile Ser Ser Xaa Glu Xaa Glu
65                  70                  75                  80

Asp Xaa Ala Xaa Tyr Tyr Cys Xaa Gln Phe Thr Thr Xaa Pro Tyr Thr
                85                  90                  95

Phe Gly Gly Gly Thr Lys Leu Glu Ile Lys Arg
                100                 105

<210> SEQ ID NO 9
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Lys Gly Leu Glu Trp Val Ser
        35                  40                  45
```

Thr Ile Ser Ser Gly Gly Gly Tyr Thr Tyr Tyr Pro Asp Ser Leu Lys
            50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys His Gly Ala Pro Met Thr Thr Val Ile Thr Tyr Ala Pro Tyr Tyr
                100                 105                 110

Phe Tyr Tyr Trp Gly Gln Gly Thr Thr Val Thr Val Ser Ser
            115                 120                 125

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ile or Asn
<220> FEATURE:
<221> NAME/KEY: MOD_RES
<222> LOCATION: (10)..(10)
<223> OTHER INFORMATION: Thr, Phe or Ile
<220> FEATURE:
<221> NAME/KEY: MOD_RES
<222> LOCATION: (11)..(11)
<223> OTHER INFORMATION: Leu or Met
<220> FEATURE:
<221> NAME/KEY: MOD_RES
<222> LOCATION: (13)..(13)
<223> OTHER INFORMATION: Leu, Ala or Val
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (18)..(18)
<223> OTHER INFORMATION: Arg or Lys
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (21)..(21)
<223> OTHER INFORMATION: Leu, Met or Ile
<220> FEATURE:
<221> NAME/KEY: MOD_RES
<222> LOCATION: (22)..(22)
<223> OTHER INFORMATION: Ser, Thr or Asn
<220> FEATURE:
<221> NAME/KEY: MOD_RES
<222> LOCATION: (39)..(39)
<223> OTHER INFORMATION: Ser or Pro
<220> FEATURE:
<221> NAME/KEY: MOD_RES
<222> LOCATION: (40)..(40)
<223> OTHER INFORMATION: Gly or Asp
<220> FEATURE:
<221> NAME/KEY: MOD_RES
<222> LOCATION: (41)..(41)
<223> OTHER INFORMATION: Gln or Ala
<220> FEATURE:
<221> NAME/KEY: MOD_RES
<222> LOCATION: (42)..(42)
<223> OTHER INFORMATION: Ala or Ser

```
<220> FEATURE:
<221> NAME/KEY: MOD_RES
<222> LOCATION: (44)..(44)
<223> OTHER INFORMATION: Arg or Lys
<220> FEATURE:
<221> NAME/KEY: MOD_RES
<222> LOCATION: (46)..(46)
<223> OTHER INFORMATION: Leu or Trp
<220> FEATURE:
<221> NAME/KEY: MOD_RES
<222> LOCATION: (57)..(57)
<223> OTHER INFORMATION: Ile or Val
<220> FEATURE:
<221> NAME/KEY: MOD_RES
<222> LOCATION: (59)..(59)
<223> OTHER INFORMATION: Ala or Ser
<220> FEATURE:
<221> NAME/KEY: MOD_RES
<222> LOCATION: (68)..(68)
<223> OTHER INFORMATION: Thr or Asn
<220> FEATURE:
<221> NAME/KEY: MOD_RES
<222> LOCATION: (69)..(69)
<223> OTHER INFORMATION: Asp or Ser
<220> FEATURE:
<221> NAME/KEY: MOD_RES
<222> LOCATION: (70)..(70)
<223> OTHER INFORMATION: Phe or Tyr
<220> FEATURE:
<221> NAME/KEY: MOD_RES
<222> LOCATION: (71)..(71)
<223> OTHER INFORMATION: Thr or Ser
<220> FEATURE:
<221> NAME/KEY: MOD_RES
<222> LOCATION: (72)..(72)
<223> OTHER INFORMATION: Leu or Phe
<220> FEATURE:
<221> NAME/KEY: MOD_RES
<222> LOCATION: (77)..(77)
<223> OTHER INFORMATION: Met or Leu
<220> FEATURE:
<221> NAME/KEY: MOD_RES
<222> LOCATION: (79)..(79)
<223> OTHER INFORMATION: Ala or Gly
<220> FEATURE:
<221> NAME/KEY: MOD_RES
<222> LOCATION: (82)..(82)
<223> OTHER INFORMATION: Phe or Ala
<220> FEATURE:
<221> NAME/KEY: MOD_RES
<222> LOCATION: (84)..(84)
<223> OTHER INFORMATION: Val or Thr

<400> SEQUENCE: 10

Glu Xaa Val Leu Thr Gln Ser Pro Ala Xaa Xaa Ser Xaa Xaa Xaa Gly
1               5                   10                  15

Glu Xaa Xaa Thr Xaa Xaa Cys Arg Ala Ser Ser Ser Val Lys Tyr Met
            20                  25                  30

Tyr Trp Tyr Gln Gln Lys Xaa Xaa Xaa Xaa Pro Xaa Leu Xaa Ile Tyr
        35                  40                  45

Tyr Thr Ser Asn Leu Ala Pro Gly Xaa Pro Xaa Arg Phe Ser Gly Ser
    50                  55                  60

Gly Ser Gly Xaa Xaa Xaa Xaa Xaa Thr Ile Ser Ser Xaa Glu Xaa Glu
65                  70                  75                  80

Asp Xaa Ala Xaa Tyr Tyr Cys Gln Gln Phe Thr Ser Pro Tyr Thr
            85                  90                  95

Phe Gly Gly Gly Thr Lys Leu Glu Ile Lys Arg
            100                 105

<210> SEQ ID NO 11
<211> LENGTH: 107
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 11

Glu Ile Val Leu Thr Gln Ser Pro Ala Thr Leu Ser Leu Ser Leu Gly
1               5                   10                  15

Glu Arg Ala Thr Leu Ser Cys Arg Ala Ser Ser Val Lys Tyr Met
            20                  25                  30

Tyr Trp Tyr Gln Gln Lys Ser Gly Gln Ala Pro Arg Leu Leu Ile Tyr
        35                  40                  45

Tyr Thr Ser Asn Leu Ala Pro Gly Ile Pro Ala Arg Phe Ser Gly Ser
    50                  55                  60

Gly Ser Gly Thr Asp Phe Thr Leu Thr Ile Ser Ser Met Glu Ala Glu
65                  70                  75                  80

Asp Phe Ala Val Tyr Tyr Cys Gln Gln Phe Thr Ser Pro Tyr Thr
                85                  90                  95

Phe Gly Gly Gly Thr Lys Leu Glu Ile Lys Arg
            100                 105

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Asn Val Leu Thr Gln Ser Pro Ala Phe Leu Ser Val Thr Pro Gly
1               5                   10                  15

Glu Lys Val Thr Ile Thr Cys Arg Ala Ser Ser Ser Val Lys Tyr Met
            20                  25                  30

Tyr Trp Tyr Gln Gln Lys Pro Asp Gln Ala Pro Lys Leu Trp Ile Tyr
        35                  40                  45

Tyr Thr Ser Asn Leu Ala Pro Gly Val Pro Ser Arg Phe Ser Gly Ser
    50                  55                  60

Gly Ser Gly Asn Asp Tyr Thr Phe Thr Ile Ser Ser Leu Glu Ala Glu
65                  70                  75                  80

Asp Ala Ala Thr Tyr Tyr Cys Gln Gln Phe Thr Ser Pro Tyr Thr
                85                  90                  95

Phe Gly Gly Gly Thr Lys Leu Glu Ile Lys Arg
            100                 105

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Ser or Tyr

<400> SEQUENCE: 13

Xaa Tyr Ala Met Ser
1               5

<210> SEQ ID NO 14
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr, Ala or Tyr
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Ser, Gly, Thr or Tyr
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Gly or Tyr
<220> FEATURE:
<221> NAME/KEY: MOD_RES
<222> LOCATION: (8)..(8)
<223> OTHER INFORMATION: Phe, Ser or Tyr
<220> FEATURE:
<221> NAME/KEY: MOD_RES
<222> LOCATION: (12)..(12)
<223> OTHER INFORMATION: Pro or Ala
<220> FEATURE:
<221> NAME/KEY: MOD_RES
<222> LOCATION: (15)..(15)
<223> OTHER INFORMATION: Leu, Tyr or Val

<400> SEQUENCE: 14

Xaa Ile Xaa Xaa Xaa Xaa Gly Xaa Thr Tyr Tyr Xaa Asp Ser Xaa Lys
1               5                   10                  15

Gly

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His or Tyr
<220> FEATURE:
<221> NAME/KEY: MOD_RES
<222> LOCATION: (2)..(2)
<223> OTHER INFORMATION: Gly or Tyr
<220> FEATURE:
<221> NAME/KEY: MOD_RES
<222> LOCATION: (3)..(3)
<223> OTHER INFORMATION: Ala or Tyr
<220> FEATURE:
<221> NAME/KEY: MOD_RES
<222> LOCATION: (6)..(6)
<223> OTHER INFORMATION: Thr or Tyr
<220> FEATURE:
<221> NAME/KEY: MOD_RES
<222> LOCATION: (8)..(8)
<223> OTHER INFORMATION: Val or Tyr
<220> FEATURE:
<221> NAME/KEY: MOD_RES
<222> LOCATION: (12)..(12)
<223> OTHER INFORMATION: Ala or Tyr

<400> SEQUENCE: 15
```

```
Xaa Xaa Xaa Pro Met Xaa Thr Xaa Ile Thr Tyr Xaa Pro Tyr Tyr Phe
1               5                   10                  15

Tyr Tyr

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Asn, Ser or Tyr
<220> FEATURE:
<221> NAME/KEY: MOD_RES
<222> LOCATION: (50)..(50)
<223> OTHER INFORMATION: Thr, Ala or Tyr
<220> FEATURE:
<221> NAME/KEY: MOD_RES
<222> LOCATION: (52)..(52)
<223> OTHER INFORMATION: Ser or Tyr
<220> FEATURE:
<221> NAME/KEY: MOD_RES
<222> LOCATION: (53)..(53)
<223> OTHER INFORMATION: Ser, Gly, Thr or Tyr
<220> FEATURE:
<221> NAME/KEY: MOD_RES
<222> LOCATION: (54)..(54)
<223> OTHER INFORMATION: Gly or Ser
<220> FEATURE:
<221> NAME/KEY: MOD_RES
<222> LOCATION: (55)..(55)
<223> OTHER INFORMATION: Gly or Tyr
<220> FEATURE:
<221> NAME/KEY: MOD_RES
<222> LOCATION: (57)..(57)
<223> OTHER INFORMATION: Phe, Ser or Tyr
<220> FEATURE:
<221> NAME/KEY: MOD_RES
<222> LOCATION: (61)..(61)
<223> OTHER INFORMATION: Pro or Ala
<220> FEATURE:
<221> NAME/KEY: MOD_RES
<222> LOCATION: (64)..(64)
<223> OTHER INFORMATION: Leu, Tyr or Val
<220> FEATURE:
<221> NAME/KEY: MOD_RES
<222> LOCATION: (99)..(99)
<223> OTHER INFORMATION: His or Tyr
<220> FEATURE:
<221> NAME/KEY: MOD_RES
<222> LOCATION: (100)..(100)
<223> OTHER INFORMATION: Gly or Tyr
<220> FEATURE:
<221> NAME/KEY: MOD_RES
<222> LOCATION: (101)..(101)
<223> OTHER INFORMATION: Ala or Tyr
<220> FEATURE:
<221> NAME/KEY: MOD_RES
<222> LOCATION: (104)..(104)
<223> OTHER INFORMATION: Thr or Tyr
<220> FEATURE:
<221> NAME/KEY: MOD_RES
<222> LOCATION: (106)..(106)
<223> OTHER INFORMATION: Val or Tyr
<220> FEATURE:
<221> NAME/KEY: MOD_RES
<222> LOCATION: (110)..(110)
<223> OTHER INFORMATION: Ala or Tyr

<400> SEQUENCE: 16

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Xaa Tyr
        20                  25                  30

Ala Met Ser Trp Val Arg Gln Ala Pro Gly Lys Gly Leu Glu Trp Val
            35                  40                  45

Ser Xaa Ile Xaa Xaa Xaa Xaa Gly Xaa Thr Tyr Tyr Xaa Asp Ser Xaa
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Xaa Xaa Xaa Pro Met Xaa Thr Xaa Ile Thr Tyr Xaa Pro Tyr
            100                 105                 110

Tyr Phe Tyr Tyr Trp Gly Gln Gly Thr Thr Val Thr Val Ser Ser
        115                 120                 125

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Tyr Ala Ile Ser
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Tyr Ser Ser Gly Gly Val Tyr Thr Tyr Tyr Arg Asp Ser Leu Lys
1               5                   10                  15

Gly

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Gly Ala Ala Met Thr Thr Val Ile Thr Tyr Ala Pro Phe Tyr Phe
1               5                   10                  15

Tyr Tyr

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Ala Ile Ser Trp Val Arg Gln Ala Pro Gly Lys Gly Leu Glu Trp Val
        35                  40                  45

Ser Thr Tyr Ser Ser Gly Gly Val Tyr Thr Tyr Tyr Arg Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Ala Ala Met Thr Thr Val Ile Thr Tyr Ala Pro Phe
            100                 105                 110

Tyr Phe Tyr Tyr Trp Gly Gln Gly Thr Thr Val Thr Val Ser Ser
            115                 120                 125

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Tyr Ala Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Ile Tyr Ser Gly Gly Ser Tyr Thr Phe Tyr Pro Asp Ser Leu Glu
1               5                   10                  15

Gly

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Gly Ala Pro Met Ser Thr Glu Ile Thr Tyr Ala Pro Tyr Tyr Phe
1               5                   10                  15

Tyr Tyr

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Gln Pro Gly Gly
```

```
                1               5                   10                  15
Ser Leu Arg Leu Ser Cys Ala Ala Ser Gly Phe Thr Phe Ser Tyr Tyr
                    20                  25                  30

Ala Met Ser Trp Val Arg Gln Ala Pro Gly Lys Gly Leu Glu Trp Val
                    35                  40                  45

Ser Thr Ile Tyr Ser Gly Gly Ser Tyr Thr Phe Tyr Pro Asp Ser Leu
                    50                  55                  60

Glu Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
                    85                  90                  95

Ala Lys His Gly Ala Pro Met Ser Thr Glu Ile Thr Tyr Ala Pro Tyr
                    100                 105                 110

Tyr Phe Tyr Tyr Trp Gly Gln Gly Thr Thr Val Thr Val Ser Ser
                    115                 120                 125
```

```
<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Tyr Ala Met Ser
 1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Ile Tyr Ser Gly Gly Gly Tyr Thr Phe Tyr Leu Asp Ser Leu Lys
 1               5                   10                  15

Gly

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Ser Tyr Pro Met Thr Thr Val Ile Thr Tyr Ala Pro Tyr Tyr Phe
 1               5                   10                  15

Tyr Tyr

<210> SEQ ID NO 28
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Thr Ile Tyr Ser Gly Gly Tyr Thr Phe Tyr Leu Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys His Ser Tyr Pro Met Thr Thr Val Ile Thr Tyr Ala Pro Tyr
            100                 105                 110

Tyr Phe Tyr Tyr Trp Gly Gln Gly Thr Thr Val Thr Val Ser Ser
            115                 120                 125

<210> SEQ ID NO 29
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Tyr Thr Tyr Tyr Pro Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys His Gly Ala Pro Met Thr Thr Val Ile Thr Tyr Ala Pro Tyr
            100                 105                 110

Tyr Phe Tyr Tyr Trp Gly Gln Gly Thr Thr Val Thr Val Ser Ser
            115                 120                 125

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Lys Tyr Met
            20                  25                  30

Tyr Trp Tyr Gln Gln Lys Pro Gly Gln Ala Pro Arg Leu Leu Ile Tyr
        35                  40                  45

Tyr Thr Ser Asn Leu Ala Pro Gly Ile Pro Ala Arg Phe Ser Gly Ser
```

```
                    50                  55                  60
Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Phe Thr Ser Pro Tyr Thr
                 85                  90                  95

Phe Gly Gly Gly Thr Lys Leu Glu Ile Lys Arg
                100                 105
```

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Tyr Gln Phe Thr Thr Ser Pro Tyr Thr
 1               5
```

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Lys Tyr Met
                 20                  25                  30

Tyr Trp Tyr Gln Gln Lys Pro Gly Gln Ala Pro Arg Leu Leu Ile Tyr
             35                  40                  45

Tyr Thr Ser Asn Leu Ala Pro Gly Ile Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Tyr Gln Phe Thr Thr Ser Pro Tyr Thr
                 85                  90                  95

Phe Gly Gly Gly Thr Lys Leu Glu Ile Lys Arg
                100                 105
```

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Gln Gln Tyr Thr Thr Ser Pro Tyr Thr
 1               5
```

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

| Glu | Ile | Val | Leu | Thr | Gln | Ser | Pro | Ala | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Ser | Ser | Val | Lys | Tyr | Met |
|---|---|---|---|---|---|---|---|---|---|---|---|---|---|---|---|
| | | | 20 | | | | | 25 | | | | | 30 | | |

| Tyr | Trp | Tyr | Gln | Gln | Lys | Pro | Gly | Gln | Ala | Pro | Arg | Leu | Leu | Ile | Tyr |
|---|---|---|---|---|---|---|---|---|---|---|---|---|---|---|---|
| | | 35 | | | | | 40 | | | | | 45 | | | |

| Tyr | Thr | Ser | Asn | Leu | Ala | Pro | Gly | Ile | Pro | Ala | Arg | Phe | Ser | Gly | Ser |
|---|---|---|---|---|---|---|---|---|---|---|---|---|---|---|---|
| | 50 | | | | | 55 | | | | | 60 | | | | |

| Gly | Ser | Gly | Thr | Asp | Phe | Thr | Leu | Thr | Ile | Ser | Ser | Leu | Glu | Pro | Glu |
|---|---|---|---|---|---|---|---|---|---|---|---|---|---|---|---|
| 65 | | | | | 70 | | | | | 75 | | | | | 80 |

| Asp | Phe | Ala | Val | Tyr | Tyr | Cys | Gln | Gln | Tyr | Thr | Thr | Ser | Pro | Tyr | Thr |
|---|---|---|---|---|---|---|---|---|---|---|---|---|---|---|---|
| | | | | 85 | | | | | 90 | | | | | 95 | |

| Phe | Gly | Gly | Gly | Thr | Lys | Leu | Glu | Ile | Lys | Arg |
|---|---|---|---|---|---|---|---|---|---|---|
| | | | 100 | | | | | 105 | | |

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

| Gln | Gln | Phe | Thr | Thr | Tyr | Pro | Tyr | Thr |
|---|---|---|---|---|---|---|---|---|
| 1 | | | | 5 | | | | |

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

| Glu | Ile | Val | Leu | Thr | Gln | Ser | Pro | Ala | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Ser | Ser | Val | Lys | Tyr | Met |
|---|---|---|---|---|---|---|---|---|---|---|---|---|---|---|---|
| | | | 20 | | | | | 25 | | | | | 30 | | |

| Tyr | Trp | Tyr | Gln | Gln | Lys | Pro | Gly | Gln | Ala | Pro | Arg | Leu | Leu | Ile | Tyr |
|---|---|---|---|---|---|---|---|---|---|---|---|---|---|---|---|
| | | 35 | | | | | 40 | | | | | 45 | | | |

| Tyr | Thr | Ser | Asn | Leu | Ala | Pro | Gly | Ile | Pro | Ala | Arg | Phe | Ser | Gly | Ser |
|---|---|---|---|---|---|---|---|---|---|---|---|---|---|---|---|
| | 50 | | | | | 55 | | | | | 60 | | | | |

| Gly | Ser | Gly | Thr | Asp | Phe | Thr | Leu | Thr | Ile | Ser | Ser | Leu | Glu | Pro | Glu |
|---|---|---|---|---|---|---|---|---|---|---|---|---|---|---|---|
| 65 | | | | | 70 | | | | | 75 | | | | | 80 |

| Asp | Phe | Ala | Val | Tyr | Tyr | Cys | Gln | Gln | Phe | Thr | Thr | Tyr | Pro | Tyr | Thr |
|---|---|---|---|---|---|---|---|---|---|---|---|---|---|---|---|
| | | | | 85 | | | | | 90 | | | | | 95 | |

| Phe | Gly | Gly | Gly | Thr | Lys | Leu | Glu | Ile | Lys | Arg |
|---|---|---|---|---|---|---|---|---|---|---|
| | | | 100 | | | | | 105 | | |

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)

```
<223> OTHER INFORMATION: Ser or Gln
<220> FEATURE:
<221> NAME/KEY: MOD_RES
<222> LOCATION: (7)..(7)
<223> OTHER INFORMATION: Lys or Ser
<220> FEATURE:
<221> NAME/KEY: MOD_RES
<222> LOCATION: (10)..(10)
<223> OTHER INFORMATION: Met or Leu
<220> FEATURE:
<221> NAME/KEY: MOD_RES
<222> LOCATION: (11)..(11)
<223> OTHER INFORMATION: Tyr or Ala

<400> SEQUENCE: 37

Arg Ala Ser Xaa Ser Val Xaa Ser Tyr Xaa Xaa
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Tyr
<220> FEATURE:
<221> NAME/KEY: MOD_RES
<222> LOCATION: (3)..(3)
<223> OTHER INFORMATION: Phe or Tyr
<220> FEATURE:
<221> NAME/KEY: MOD_RES
<222> LOCATION: (6)..(6)
<223> OTHER INFORMATION: Ser or Tyr

<400> SEQUENCE: 38

Xaa Gln Xaa Thr Thr Xaa Pro Tyr Thr
1               5

<210> SEQ ID NO 39
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Ser or Gln
<220> FEATURE:
<221> NAME/KEY: MOD_RES
<222> LOCATION: (30)..(30)
<223> OTHER INFORMATION: Lys or Ser
<220> FEATURE:
<221> NAME/KEY: MOD_RES
<222> LOCATION: (33)..(33)
<223> OTHER INFORMATION: Met or Leu
<220> FEATURE:
<221> NAME/KEY: MOD_RES
<222> LOCATION: (34)..(34)
<223> OTHER INFORMATION: Tyr or Ala
<220> FEATURE:
<221> NAME/KEY: MOD_RES
<222> LOCATION: (50)..(50)
<223> OTHER INFORMATION: Tyr or Asp
<220> FEATURE:
<221> NAME/KEY: MOD_RES
<222> LOCATION: (51)..(51)
<223> OTHER INFORMATION: Thr or Ala
<220> FEATURE:
<221> NAME/KEY: MOD_RES
<222> LOCATION: (54)..(54)
```

```
<223> OTHER INFORMATION: Leu or Arg
<220> FEATURE:
<221> NAME/KEY: MOD_RES
<222> LOCATION: (56)..(56)
<223> OTHER INFORMATION: Pro or Thr
<220> FEATURE:
<221> NAME/KEY: MOD_RES
<222> LOCATION: (89)..(89)
<223> OTHER INFORMATION: Gln or Tyr
<220> FEATURE:
<221> NAME/KEY: MOD_RES
<222> LOCATION: (91)..(91)
<223> OTHER INFORMATION: Phe or Tyr
<220> FEATURE:
<221> NAME/KEY: MOD_RES
<222> LOCATION: (94)..(94)
<223> OTHER INFORMATION: Ser or Tyr

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Xaa Ser Val Xaa Ser Tyr
            20                  25                  30

Xaa Xaa Trp Tyr Gln Gln Lys Pro Gly Gln Ala Pro Arg Leu Leu Ile
        35                  40                  45

Tyr Xaa Xaa Ser Asn Xaa Ala Xaa Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Xaa Gln Xaa Thr Thr Xaa Pro Tyr
                85                  90                  95

Thr Phe Gly Gly Gly Thr Lys Leu Glu Ile Lys Arg
            100                 105

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Asp
<220> FEATURE:
<221> NAME/KEY: MOD_RES
<222> LOCATION: (2)..(2)
<223> OTHER INFORMATION: Thr or Ala
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (7)..(7)
<223> OTHER INFORMATION: Pro or Thr

<400> SEQUENCE: 40

Xaa Xaa Ser Asn Xaa Ala Xaa
1               5

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Asn or Val
<220> FEATURE:
<221> NAME/KEY: MOD_RES
<222> LOCATION: (4)..(4)
<223> OTHER INFORMATION: Leu or Met
<220> FEATURE:
<221> NAME/KEY: MOD_RES
<222> LOCATION: (46)..(46)
<223> OTHER INFORMATION: Trp or Leu
<220> FEATURE:
<221> NAME/KEY: MOD_RES
<222> LOCATION: (48)..(48)
<223> OTHER INFORMATION: Tyr or Lys
<220> FEATURE:
<221> NAME/KEY: MOD_RES
<222> LOCATION: (68)..(68)
<223> OTHER INFORMATION: Asn or Thr
<220> FEATURE:
<221> NAME/KEY: MOD_RES
<222> LOCATION: (70)..(70)
<223> OTHER INFORMATION: Tyr or Phe
<220> FEATURE:
<221> NAME/KEY: MOD_RES
<222> LOCATION: (88)..(88)
<223> OTHER INFORMATION: Gln or Tyr
<220> FEATURE:
<221> NAME/KEY: MOD_RES
<222> LOCATION: (90)..(90)
<223> OTHER INFORMATION: Phe or Tyr
<220> FEATURE:
<221> NAME/KEY: MOD_RES
<222> LOCATION: (93)..(93)
<223> OTHER INFORMATION: Ser or Tyr

<400> SEQUENCE: 41

Xaa Xaa Val Xaa Thr Gln Ser Pro Ala Phe Leu Ser Val Thr Pro Gly
1               5                   10                  15

Glu Lys Val Thr Ile Thr Cys Arg Ala Ser Ser Ser Val Lys Tyr Met
            20                  25                  30

Tyr Trp Tyr Gln Gln Lys Pro Asp Gln Ala Pro Lys Leu Xaa Ile Xaa
        35                  40                  45

Tyr Thr Ser Asn Leu Ala Pro Gly Val Pro Ser Arg Phe Ser Gly Ser
    50                  55                  60

Gly Ser Gly Xaa Asp Xaa Thr Phe Thr Ile Ser Ser Leu Glu Ala Glu
65                  70                  75                  80

Asp Ala Ala Thr Tyr Tyr Cys Xaa Gln Xaa Thr Thr Xaa Pro Tyr Thr
                85                  90                  95

Phe Gly Gly Gly Thr Lys Leu Glu Ile Lys Arg
            100                 105

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Ser or Tyr

<400> SEQUENCE: 42

Xaa Met Ala Ser
1
```

```
<210> SEQ ID NO 43
<211> LENGTH: 98
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Gln Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 44
<211> LENGTH: 95
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 45
<211> LENGTH: 95
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45
```

```
Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Gly Ala Pro Met Thr Thr Val Ile Thr Tyr Ala Pro Tyr Tyr Phe
1               5                   10                  15

Asp Tyr

<210> SEQ ID NO 47
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Met or Gln
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (13)..(13)
<223> OTHER INFORMATION: Lys or Gln
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (40)..(40)
<223> OTHER INFORMATION: Thr or Ala
<220> FEATURE:
<221> NAME/KEY: MOD_RES
<222> LOCATION: (42)..(42)
<223> OTHER INFORMATION: Glu or Gly
<220> FEATURE:
<221> NAME/KEY: MOD_RES
<222> LOCATION: (44)..(44)
<223> OTHER INFORMATION: Arg or Gly
<220> FEATURE:
<221> NAME/KEY: MOD_RES
<222> LOCATION: (49)..(49)
<223> OTHER INFORMATION: Ala or Ser
<220> FEATURE:
<221> NAME/KEY: MOD_RES
<222> LOCATION: (75)..(75)
<223> OTHER INFORMATION: Ala or Ser
<220> FEATURE:
<221> NAME/KEY: MOD_RES
<222> LOCATION: (80)..(80)
<223> OTHER INFORMATION: Phe or Tyr
<220> FEATURE:
<221> NAME/KEY: MOD_RES
<222> LOCATION: (84)..(84)
<223> OTHER INFORMATION: Ser or Asn
<220> FEATURE:
<221> NAME/KEY: MOD_RES
```

```
<222> LOCATION: (88)..(88)
<223> OTHER INFORMATION: Ser or Ala
<220> FEATURE:
<221> NAME/KEY: MOD_RES
<222> LOCATION: (97)..(97)
<223> OTHER INFORMATION: Val or Ala
<220> FEATURE:
<221> NAME/KEY: MOD_RES
<222> LOCATION: (98)..(98)
<223> OTHER INFORMATION: Arg or Lys
<220> FEATURE:
<221> NAME/KEY: MOD_RES
<222> LOCATION: (115)..(115)
<223> OTHER INFORMATION: Asp or Tyr
<220> FEATURE:
<221> NAME/KEY: MOD_RES
<222> LOCATION: (123)..(123)
<223> OTHER INFORMATION: Leu or Val

<400> SEQUENCE: 47

Glu Val Xaa Leu Xaa Glu Ser Gly Gly Gly Leu Val Xaa Pro Gly Gly
1               5                   10                  15

Ser Leu Xaa Leu Ser Cys Ala Ala Ser Gly Phe Thr Phe Ser Asn Tyr
            20                  25                  30

Ala Met Ser Trp Val Arg Gln Xaa Pro Xaa Lys Xaa Leu Glu Trp Val
        35                  40                  45

Xaa Thr Ile Ser Ser Gly Gly Gly Tyr Thr Tyr Tyr Pro Asp Ser Leu
    50                  55                  60

Lys Gly Arg Phe Thr Ile Ser Arg Asp Asn Xaa Lys Asn Thr Leu Xaa
65                  70                  75                  80

Leu Gln Met Xaa Ser Leu Arg Xaa Glu Asp Thr Ala Val Tyr Tyr Cys
                85                  90                  95

Xaa Xaa His Gly Ala Pro Met Thr Thr Val Ile Thr Tyr Ala Pro Tyr
            100                 105                 110

Tyr Phe Xaa Tyr Trp Gly Gln Gly Thr Thr Xaa Thr Val Ser Ser
        115                 120                 125

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Asn Val Leu Thr Gln Ser Pro Ala Thr Leu Ser Leu Ser Leu
1               5                   10                  15

Gly Glu Arg Ala Thr Leu Ser Cys Arg Ala Ser Ser Ser Val Lys Tyr
            20                  25                  30

Met Tyr Trp Tyr Gln Gln Lys Ser Gly Gln Ala Pro Arg Leu Leu Ile
        35                  40                  45

Tyr Tyr Thr Ser Asn Leu Ala Pro Gly Ile Pro Ala Arg Phe Ser Gly
    50                  55                  60

Ser Gly Ser Gly Thr Asp Phe Thr Leu Thr Ile Ser Ser Met Glu Ala
65                  70                  75                  80

Glu Asp Phe Ala Val Tyr Tyr Cys Gln Gln Phe Thr Thr Ser Pro Tyr
                85                  90                  95

Thr Phe Gly Gly Gly Thr Lys Leu Glu Ile Lys Arg
            100                 105

<210> SEQ ID NO 49
<211> LENGTH: 108
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Asn or Val
<220> FEATURE:
<221> NAME/KEY: MOD_RES
<222> LOCATION: (4)..(4)
<223> OTHER INFORMATION: Leu or Met
<220> FEATURE:
<221> NAME/KEY: MOD_RES
<222> LOCATION: (27)..(27)
<223> OTHER INFORMATION: Ser or Gln
<220> FEATURE:
<221> NAME/KEY: MOD_RES
<222> LOCATION: (30)..(30)
<223> OTHER INFORMATION: Lys or Ser
<220> FEATURE:
<221> NAME/KEY: MOD_RES
<222> LOCATION: (33)..(33)
<223> OTHER INFORMATION: Met or Leu
<220> FEATURE:
<221> NAME/KEY: MOD_RES
<222> LOCATION: (34)..(34)
<223> OTHER INFORMATION: Tyr or Ala
<220> FEATURE:
<221> NAME/KEY: MOD_RES
<222> LOCATION: (47)..(47)
<223> OTHER INFORMATION: Trp or Leu
<220> FEATURE:
<221> NAME/KEY: MOD_RES
<222> LOCATION: (49)..(49)
<223> OTHER INFORMATION: Tyr or Lys
<220> FEATURE:
<221> NAME/KEY: MOD_RES
<222> LOCATION: (50)..(50)
<223> OTHER INFORMATION: Tyr or Asp
<220> FEATURE:
<221> NAME/KEY: MOD_RES
<222> LOCATION: (51)..(51)
<223> OTHER INFORMATION: Thr or Ala
<220> FEATURE:
<221> NAME/KEY: MOD_RES
<222> LOCATION: (54)..(54)
<223> OTHER INFORMATION: Leu or Arg
<220> FEATURE:
<221> NAME/KEY: MOD_RES
<222> LOCATION: (56)..(56)
<223> OTHER INFORMATION: Pro or Thr
<220> FEATURE:
<221> NAME/KEY: MOD_RES
<222> LOCATION: (69)..(69)
<223> OTHER INFORMATION: Asn or Thr
<220> FEATURE:
<221> NAME/KEY: MOD_RES
<222> LOCATION: (71)..(71)
<223> OTHER INFORMATION: Tyr or Phe
<220> FEATURE:
<221> NAME/KEY: MOD_RES
<222> LOCATION: (89)..(89)
<223> OTHER INFORMATION: Gln or Tyr
<220> FEATURE:
<221> NAME/KEY: MOD_RES
<222> LOCATION: (91)..(91)
<223> OTHER INFORMATION: Phe or Tyr
<220> FEATURE:
<221> NAME/KEY: MOD_RES
<222> LOCATION: (94)..(94)
<223> OTHER INFORMATION: Ser or Tyr

<400> SEQUENCE: 49
```

Xaa Xaa Val Xaa Thr Gln Ser Pro Ala Phe Leu Ser Val Thr Pro Gly
1               5                   10                  15

Glu Lys Val Thr Ile Thr Cys Arg Ala Ser Xaa Ser Val Xaa Ser Tyr
                20                  25                  30

Xaa Xaa Trp Tyr Gln Gln Lys Pro Asp Gln Ala Pro Lys Leu Xaa Ile
            35                  40                  45

Xaa Xaa Xaa Ser Asn Xaa Ala Xaa Gly Val Pro Ser Arg Phe Ser Gly
        50                  55                  60

Ser Gly Ser Gly Xaa Asp Xaa Thr Phe Thr Ile Ser Ser Leu Glu Ala
65                  70                  75                  80

Glu Asp Ala Ala Thr Tyr Tyr Cys Xaa Gln Xaa Thr Xaa Pro Tyr
                85                  90                  95

Thr Phe Gly Gly Gly Thr Lys Leu Glu Ile Lys Arg
            100                 105

<210> SEQ ID NO 50
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gaagtgatgc tggtggagtc tgggggaggc ttagtgaagc ctggagggtc cctgaaactc      60
tcctgtgcag cctctggatt cactttcagt aactatgcca tgtcttgggt tcgtcagact     120
ccggagaaga ggctggagtg ggtcgcaacc ataagtagtg gtggaggtta cacctattat     180
ccagacagtt tgaaggggcg attcaccatc tccagagaca atgccaagaa caccctgttc     240
ctgcaaatga gcagtctgag gtctgaggac acggccgtgt attattgtgt aagacatggg     300
gcccccatga ctacggtgat aacttacgct ccttactatt ttgactactg gggccagggc     360
accactctca cagtctcctc a                                                381

<210> SEQ ID NO 51
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Gly Tyr Thr Tyr Tyr Pro Asp Ser Leu
        50                  55                  60

Lys Gly Arg Phe Thr Ile Ser Arg Asp Asn Ala Lys Asn Thr Leu Phe
65                  70                  75                  80

Leu Gln Met Ser Ser Leu Arg Ser Glu Asp Thr Ala Val Tyr Tyr Cys
                85                  90                  95

Val Arg His Gly Ala Pro Met Thr Thr Val Ile Thr Tyr Ala Pro Tyr
            100                 105                 110

Tyr Phe Asp Tyr Trp Gly Gln Gly Thr Thr Leu Thr Val Ser Ser
        115                 120                 125

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gaaaatgtgc tcacccagtc tccagcaatc atgtctgcat ctctggggga gaaggtcacc      60
atgaactgca gggccagctc aagtgtaaaa tacatgtact ggtaccagca gaagtcagat     120
gcctccccca aactatggat ttattacaca tccaacctgg ctcctggagt cccagctcgc     180
ttcagtggca gtgggtctgg gaactcttat tctctcacaa tcagcagcat ggagggtgaa     240
gatgctgcca cttattactg ccagcagttt actacttccc cgtacacgtt cggagggggg     300
accaagctgg aaataaaacg g                                               321

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Asn Val Leu Thr Gln Ser Pro Ala Ile Met Ser Ala Ser Leu Gly
1               5                   10                  15

Glu Lys Val Thr Met Asn Cys Arg Ala Ser Ser Ser Val Lys Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Thr Ser Pro Tyr Thr
                85                  90                  95

Phe Gly Gly Gly Thr Lys Leu Glu Ile Lys Arg
            100                 105

<210> SEQ ID NO 54
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (91)..(93)
<223> OTHER INFORMATION: This region may encompass 'TAC' or 'TCA'
<220> FEATURE:
<221> NAME/KEY: modified_base
<222> LOCATION: (148)..(150)
<223> OTHER INFORMATION: This region may encompass 'TAC' or 'GCC'
<220> FEATURE:
<221> NAME/KEY: modified_base
<222> LOCATION: (154)..(156)
<223> OTHER INFORMATION: This region may encompass 'TCC' or 'TAC'
<220> FEATURE:
<221> NAME/KEY: modified_base
<222> LOCATION: (157)..(159)
<223> OTHER INFORMATION: This region may encompass 'GGT' or 'ACC'

-continued

```
<220> FEATURE:
<221> NAME/KEY: modified_base
<222> LOCATION: (169)..(171)
<223> OTHER INFORMATION: This region may encompass 'TTC' or 'TCC'
<220> FEATURE:
<221> NAME/KEY: modified_base
<222> LOCATION: (181)..(183)
<223> OTHER INFORMATION: This region may encompass 'CCC' or 'GCC'
<220> FEATURE:
<221> NAME/KEY: modified_base
<222> LOCATION: (190)..(192)
<223> OTHER INFORMATION: This region may encompass 'CTG' or 'TAC'

<400> SEQUENCE: 54
gaggtgcagc tgctggagtc cggcggaggc ctggtgcagc cggcggctc cctgcggctg      60 tcctgcgccg cctccggctt caccttctcc nnntacgcca tgtcctgggt gcggcaggcc    120
cccggcaagg gcctggagtg ggtgtccnnn atcnnnnnnt ccggaggcnn nacctactat    180
nnngactccn nnaagggccg gttcaccatc tcccggaca actccaagaa caccctgtac     240
ctgcagatga actccctgcg ggccgaagac accgccgtgt actattgcgc caagcatgac    300
gccctcatga ccactgtgat cacctacgcc ccctcttact tctactactg ggccagggc     360 accacggtca ccgtctcctc a                                              381

<210> SEQ ID NO 55
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Tyr or Ser
<220> FEATURE:
<221> NAME/KEY: MOD_RES
<222> LOCATION: (50)..(50)
<223> OTHER INFORMATION: Tyr or Ala
<220> FEATURE:
<221> NAME/KEY: MOD_RES
<222> LOCATION: (52)..(52)
<223> OTHER INFORMATION: Ser or Tyr
<220> FEATURE:
<221> NAME/KEY: MOD_RES
<222> LOCATION: (53)..(53)
<223> OTHER INFORMATION: Gly or Thr
<220> FEATURE:
<221> NAME/KEY: MOD_RES
<222> LOCATION: (57)..(57)
<223> OTHER INFORMATION: Phe or Ser
<220> FEATURE:
<221> NAME/KEY: MOD_RES
<222> LOCATION: (61)..(61)
<223> OTHER INFORMATION: Pro or Ala
<220> FEATURE:
<221> NAME/KEY: MOD_RES
<222> LOCATION: (64)..(64)
<223> OTHER INFORMATION: Leu or Tyr

<400> SEQUENCE: 55

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Xaa Tyr
             20                  25                  30

Ala Met Ser Trp Val Arg Gln Ala Pro Gly Lys Gly Leu Glu Trp Val
         35                  40                  45

Ser Xaa Ile Xaa Xaa Ser Gly Gly Xaa Thr Tyr Tyr Xaa Asp Ser Xaa
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Asp Ala Leu Met Thr Thr Val Ile Thr Tyr Ala Pro Ser
            100                 105                 110

Tyr Phe Tyr Tyr Trp Gly Gln Gly Thr Thr Val Thr Val Ser Ser
        115                 120                 125

<210> SEQ ID NO 56
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gaggtgcagc tgctggagtc cggcggaggc ctggtgcagc ccggcggctc cctgcggctg     60
tcctgcgccg cctccggctt caccttctcc aactacgcca tttcctgggt gcggcaggcc    120
cccggcaagg gcctggagtg ggtgtccacc tactcctccg gcggagtcta cacctactat    180
cgcgactccc tgaagggccg gttcaccatc tcccgggaca actccaagaa caccctgtac    240
ctgcagatga actccctgcg ggccgaagac accgccgtgt actattgcgc aagcacggc     300 gccgccatga ccactgtgat cacctatgcc ccttttact tctactactg gggccagggc    360
accacggtca ccgtctcctc a                                              381

<210> SEQ ID NO 57
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gaggtgcagc tgctggagtc cggcggaggc ctggtgcagc ccggcggctc cctgcggctg     60
tcctgcgccg cctccggctt caccttctcc tactacgcca tgtcctgggt gcggcaggcc    120
cccggcaagg gcctggagtg ggtgtccacc atctactccg gcggaagcta cacctcctat    180
cccgactccc tggagggccg gttcaccatc tcccgggaca actccaagaa caccctgtac    240
ctgcagatga actccctgcg ggccgaagac accgccgtgt actattgcgc aagcacggc     300 gcccccatga gcactgagat cacctacgcc ccctattact tctactactg gggccagggc    360
accacggtca ccgtctcctc a                                              381

<210> SEQ ID NO 58
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gaggtgcagc tgctggagtc cggcggaggc ctggtgcagc ccggcggctc cctgcggctg     60
tcctgcgccg cctccggctt caccttctcc aactactaca tgtcctgggt gcggcaggcc    120
cccggcaagg gcctggagtg ggtgtccacc atctactccg gcggaggcta cacctcctat    180
ctcgactccc tgaagggccg gttcaccatc tcccgggaca actccaagaa caccctgtac    240
```

```
ctgcagatga actccctgcg ggccgaagac accgccgtgt actattgcgc caagcacagc    300
taccccatga ccactgtgat cacctacgcc cctattact tctactactg gggccagggc    360
accacggtca ccgtctcctc a                                              381
```

<210> SEQ ID NO 59
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gaggtgcagc tgctggagtc cggcggaggc ctggtgcagc ccggcggctc cctgcggctg    60
tcctgcgccg cctccggctt caccttctcc aactacgcca tgtcctgggt gcggcaggcc    120
cccggcaagg gcctggagtg ggtgtccacc atctcctccg gcggaggcta cacctactat    180
cccgactccc tgaagggccg gttcaccatc tcccgggaca actccaagaa caccctgtac    240
ctgcagatga actccctgcg ggccgaagac accgccgtgt actattgcgc caagcacggc    300
gcccccatga ccactgtgat cacctacgcc cctattact tctactactg gggccagggc    360
accacggtca ccgtctcctc a                                              381
```

<210> SEQ ID NO 60
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (91)..(93)
<223> OTHER INFORMATION: This region may encompass 'AAC' or 'TCC'
<220> FEATURE:
<221> NAME/KEY: modified_base
<222> LOCATION: (148)..(150)
<223> OTHER INFORMATION: This region may encompass 'ACC' or 'GCC'
<220> FEATURE:
<221> NAME/KEY: modified_base
<222> LOCATION: (157)..(159)
<223> OTHER INFORMATION: This region may encompass 'TCC' or 'GGA'
<220> FEATURE:
<221> NAME/KEY: modified_base
<222> LOCATION: (160)..(162)
<223> OTHER INFORMATION: This region may encompass 'GGC' or 'TCC'
<220> FEATURE:
<221> NAME/KEY: modified_base
<222> LOCATION: (169)..(171)
<223> OTHER INFORMATION: This region may encompass 'TAC' or 'TCC'
<220> FEATURE:
<221> NAME/KEY: modified_base
<222> LOCATION: (181)..(183)
<223> OTHER INFORMATION: This region may encompass 'CCC' or 'GCC'
<220> FEATURE:
<221> NAME/KEY: modified_base
<222> LOCATION: (190)..(192)
<223> OTHER INFORMATION: This region may encompass 'CTG' or 'GTC'

<400> SEQUENCE: 60

```
gaggtgcagc tgctggagtc cggcggaggc ctggtgcagc ccggcggctc cctgcggctg    60
tcctgcgccg cctccggctt caccttctcc nnntacgcca tgtcctgggt gcggcaggcc    120
cccggcaagg gcctggagtg ggtgtccnnn atctccnnnn nnggaggcnn nacctactat    180
nnngactccn nnaagggccg gttcaccatc tcccgggaca actccaagaa caccctgtac    240
ctgcagatga actccctgcg ggccgaagac accgccgtgt actattgcgc caagcacggc    300
```

```
gcccccatga ccactgtgat cacctacgcc ccctattact tctactactg gggccagggc    360
accacggtca ccgtctcctc a                                              381
```

<210> SEQ ID NO 61
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Asn or Ser
<220> FEATURE:
<221> NAME/KEY: MOD_RES
<222> LOCATION: (50)..(50)
<223> OTHER INFORMATION: Thr or Ala
<220> FEATURE:
<221> NAME/KEY: MOD_RES
<222> LOCATION: (53)..(54)
<223> OTHER INFORMATION: Ser or Gly
<220> FEATURE:
<221> NAME/KEY: MOD_RES
<222> LOCATION: (57)..(57)
<223> OTHER INFORMATION: Tyr or Ser
<220> FEATURE:
<221> NAME/KEY: MOD_RES
<222> LOCATION: (61)..(61)
<223> OTHER INFORMATION: Pro or Ala
<220> FEATURE:
<221> NAME/KEY: MOD_RES
<222> LOCATION: (64)..(64)
<223> OTHER INFORMATION: Leu or Val

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Tyr
            20                  25                  30

Ala Met Ser Trp Val Arg Gln Ala Pro Gly Lys Gly Leu Glu Trp Val
        35                  40                  45

Ser Xaa Ile Ser Xaa Xaa Gly Gly Xaa Thr Tyr Tyr Xaa Asp Ser Xaa
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Ala Pro Met Thr Thr Val Ile Thr Tyr Ala Pro Tyr
            100                 105                 110

Tyr Phe Tyr Tyr Trp Gly Gln Gly Thr Thr Val Thr Val Ser Ser
        115                 120                 125

<210> SEQ ID NO 62
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gagatcgtgc tgacccagtc ccccgccacc ctgtccctgt ccctgggcga gcgggccacc    60
ctgtcctgcc gggcctccag ctccgtgaag tacatgtact ggtaccagca gaagtccggc   120
caggcccccc ggctgctgat ctactacacc tccaacctgg cccccggcat cccgcccgg    180
```

```
ttctccggct ccggctccgg caccgacttc accctgacca tctccagcat ggaggccgag    240
gacttcgccg tgtactactg ccagcagttc accacctccc cctacacctt cggcggaggc    300
accaagctcg agatcaaacg t                                              321
```

<210> SEQ ID NO 63
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gagatcgtgc tgacccagtc ccccgccacc ctgtccctgt ccccggcga gcgggccacc     60 ctgtcctgcc gggcctccag ctccgtgaag tacatgtact ggtaccagca gaagcccggc    120
caggcccccc ggctgctgat ctactacacc tccaacctgg ccccggcat ccccgcccgg     180 ttctccggct ccggctccgg caccgacttc accctgacca tctcctccct ggagcccgag    240
gacttcgccg tgtactactg ccagcagttc accacctccc cctacacctt cggcggaggc    300
accaagctcg agatcaagcg g                                              321
```

<210> SEQ ID NO 64
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
gagatcgtgc tgacccagtc ccccgccacc ctgtccctgt ccccggcga gcgggccacc     60 ctgtcctgcc gggcctccag ctccgtgaag tacatgtact ggtaccagca gaagcccggc    120
caggcccccc ggctgctgat ctactacacc tccaacctgg ccccggcat ccccgcccgg     180 ttctccggct ccggctccgg caccgacttc accctgacca tctcctccct ggagcccgag    240
gacttcgccg tgtactactg ctaccagttc accacctccc cctacacctt cggcggaggc    300
accaagctcg agatcaagcg g                                              321
```

<210> SEQ ID NO 65
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gagatcgtgc tgacccagtc ccccgccacc ctgtccctgt ccccggcga gcgggccacc     60 ctgtcctgcc gggcctccag ctccgtgaag tacatgtact ggtaccagca gaagcccggc    120
caggcccccc ggctgctgat ctactacacc tccaacctgg ccccggcat ccccgcccgg     180 ttctccggct ccggctccgg caccgacttc accctgacca tctcctccct ggagcccgag    240
gacttcgccg tgtactactg ccagcagtac accacctccc cctacacctt cggcggaggc    300
accaagctcg agatcaagcg g                                              321
```

<210> SEQ ID NO 66
<211> LENGTH: 321
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 66

```
gagatcgtgc tgacccagtc ccccgccacc ctgtccctgt ccccggcga gcgggccacc      60
ctgtcctgcc gggcctccag ctccgtgaag tacatgtact ggtaccagca gaagcccggc    120
caggccccc  ggctgctgat ctactacacc tccaacctgg ccccggcat  ccccgcccgg    180
ttctccggct ccggctccgg caccgacttc accctgacca tctcctccct ggagcccgag    240
gacttcgccg tgtactactg ccagcagttc accacctacc cctacacctt cggcggaggc    300
accaagctcg agatcaagcg g                                              321
```

<210> SEQ ID NO 67
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (79)..(81)
<223> OTHER INFORMATION: This region may encompass 'AGC' or 'CAG'
<220> FEATURE:
<221> NAME/KEY: modified_base
<222> LOCATION: (88)..(90)
<223> OTHER INFORMATION: This region may encompass 'AGG' or 'TCC'
<220> FEATURE:
<221> NAME/KEY: modified_base
<222> LOCATION: (97)..(99)
<223> OTHER INFORMATION: This region may encompass 'ATG' or 'CTG'
<220> FEATURE:
<221> NAME/KEY: modified_base
<222> LOCATION: (100)..(102)
<223> OTHER INFORMATION: This region may encompass 'TAC' or 'GCC'
<220> FEATURE:
<221> NAME/KEY: modified_base
<222> LOCATION: (148)..(150)
<223> OTHER INFORMATION: This region may encompass 'TAC' or 'GAC'
<220> FEATURE:
<221> NAME/KEY: modified_base
<222> LOCATION: (151)..(153)
<223> OTHER INFORMATION: This region may encompass 'ACC' or 'GCC'
<220> FEATURE:
<221> NAME/KEY: modified_base
<222> LOCATION: (160)..(162)
<223> OTHER INFORMATION: This region may encompass 'CTG' or 'CGG'
<220> FEATURE:
<221> NAME/KEY: modified_base
<222> LOCATION: (166)..(168)
<223> OTHER INFORMATION: This region may encompass 'CCC' or 'ACC'
<220> FEATURE:
<221> NAME/KEY: modified_base
<222> LOCATION: (265)..(267)
<223> OTHER INFORMATION: This region may encompass 'CAG' or 'TAC'
<220> FEATURE:
<221> NAME/KEY: modified_base
<222> LOCATION: (271)..(273)
<223> OTHER INFORMATION: This region may encompass 'TTC' or 'TAC'
<220> FEATURE:
<221> NAME/KEY: modified_base
<222> LOCATION: (280)..(282)
<223> OTHER INFORMATION: This region may encompass 'TCC' or 'TAC'

<400> SEQUENCE: 67

```
gagatcgtgc tgacccagtc ccccgccacc ctgtccctgt ccccggcga gcgggccacc      60
ctgtcctgcc gggcctccnn ntccgtgnnn tcctacnnnn nntggtacca gcagaagccc    120
ggccaggccc ccggctgct  gatctacnnn nnntccaacn ngccnnngg  catccccgcc    180
```

```
cggttctccg gctccggctc cggcaccgac ttcaccctga ccatctcctc cctggagccc      240
gaggacttcg ccgtgtacta ctgcnnncag nnnaccaccn nncctacac cttcggcgga       300 ggcaccaagc tcgagatcaa gcgg                                             324
```

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gagaacgtgc tgacccagtc ccccgccttc ctgtccgtga ccccggcga gaaggtgacc      60 atcacctgcc gggcctccag ctccgtgaag tacatgtact ggtaccagca gaagcccgac     120 caggcccca agctgtggat ctattacacc tccaacctgg ccccggcgt gccctcccgg       180 ttctccggct ccggctccgg caacgactac accttcacca tctccagcct ggaggccgag    240
gacgccgcca cctattactg ccagcagttc accacctcac cctacacctt cggaggcggg   300
accaagctcg agatcaaacg t                                              321
```

<210> SEQ ID NO 69
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(3)
<223> OTHER INFORMATION: This region may encompass 'GAG' or 'GAC'
<220> FEATURE:
<221> NAME/KEY: modified_base
<222> LOCATION: (4)..(6)
<223> OTHER INFORMATION: This region may encompass 'AAC' or 'GTG'
<220> FEATURE:
<221> NAME/KEY: modified_base
<222> LOCATION: (10)..(12)
<223> OTHER INFORMATION: This region may encompass 'CTG' or 'ATG'
<220> FEATURE:
<221> NAME/KEY: modified_base
<222> LOCATION: (136)..(138)
<223> OTHER INFORMATION: This region may encompass 'TGG' or 'CTG'
<220> FEATURE:
<221> NAME/KEY: modified_base
<222> LOCATION: (142)..(144)
<223> OTHER INFORMATION: This region may encompass 'TAT' or 'AAG'
<220> FEATURE:
<221> NAME/KEY: modified_base
<222> LOCATION: (202)..(204)
<223> OTHER INFORMATION: This region may encompass 'AAC' or 'ACC'
<220> FEATURE:
<221> NAME/KEY: modified_base
<222> LOCATION: (208)..(210)
<223> OTHER INFORMATION: This region may encompass 'TAC' or 'TTC'
<220> FEATURE:
<221> NAME/KEY: modified_base
<222> LOCATION: (262)..(264)
<223> OTHER INFORMATION: This region may encompass 'CAG' or 'TAC'
<220> FEATURE:
<221> NAME/KEY: modified_base
<222> LOCATION: (268)..(270)
<223> OTHER INFORMATION: This region may encompass 'TTC' or 'TAC'
<220> FEATURE:
<221> NAME/KEY: modified_base
<222> LOCATION: (277)..(279)
<223> OTHER INFORMATION: This region may encompass 'TCC' or 'TAC'

<400> SEQUENCE: 69

```
nnnnnngtgn nnacccagtc ccccgccttc ctgtccgtga ccccggcga gaaggtgacc      60 atcacctgcc gggcctccag ctccgtgaag tacatgtact ggtaccagca gaagcccgac    120 caggcccca agctgnnnat cnnntacacc tccaacctgg ccccggcgt gccctcccgg      180 ttctccggct ccggctccgg cnnngacnnn accttcacca tctccagcct ggaggccgag    240
gacgccgcca cctattactg cnnncagnnn accaccnnnc cctacacctt cggcggaggc    300
accaagctcg agatcaagcg g                                              321
```

```
<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Met Leu Val Glu Ser Gly Gly Gly Val Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Ile Arg Gln Thr Pro Glu Lys Arg Leu Glu Trp Val
        35                  40                  45

Ala Thr Ile Ser Asn Gly Gly Ser Tyr Thr Tyr Tyr Pro Asp Ser Val
    50                  55                  60

Lys Gly Arg Phe Thr Ile Ser Arg Asp Asn Val Lys Asn Ile Leu Tyr
65                  70                  75                  80

Leu Gln Met Arg Ser Leu Arg Ser Glu Asp Thr Ala Met Tyr Tyr Cys
                85                  90                  95

Ala Arg Arg Ser Ser Asp Tyr Asp Ser Trp Phe Ala Tyr Trp Gly Gln
            100                 105                 110

Gly Thr Leu Val Thr Val Ser Ser
        115                 120
```

```
<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Met Leu Val Glu Ser Gly Gly Gly Phe Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Val Arg Gln Thr Pro Glu Lys Arg Leu Glu Trp Val
        35                  40                  45

Ala Thr Ile Ser Asn Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Ser Ser Asp Tyr Asp Ser Trp Phe Ala Tyr Trp Gly Gln
            100                 105                 110

Gly Thr Leu Val Thr Val Ser Ser
```

115                 120

<210> SEQ ID NO 72
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Met Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Gly Tyr Thr Tyr Tyr Pro Asp Ser Leu
    50                  55                  60

Lys Gly Arg Phe Thr Ile Ser Arg Asp Asn Ala Lys Asn Thr Leu Phe
65                  70                  75                  80

Leu Gln Met Ser Ser Leu Arg Ser Glu Asp Thr Ala Val Tyr Tyr Cys
                85                  90                  95

Val Arg His Gly Ala Pro Met Thr Thr Val Ile Thr Tyr Ala Pro Tyr
            100                 105                 110

Tyr Phe Asp Tyr Trp Gly Gln Gly Thr Thr Leu Thr Val Ser Ser
        115                 120                 125

<210> SEQ ID NO 73
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Met Leu Val Glu Ser Gly Gly Gly Val Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Gly Tyr Thr Tyr Tyr Pro Asp Ser Leu
    50                  55                  60

Lys Gly Arg Phe Thr Ile Ser Arg Asp Asn Ala Lys Asn Ile Leu Phe
65                  70                  75                  80

Leu Gln Met Ser Ser Leu Arg Ser Glu Asp Thr Ala Val Tyr Tyr Cys
                85                  90                  95

Val Arg His Gly Ala Pro Met Thr Thr Val Ile Thr Tyr Ala Pro Tyr
            100                 105                 110

Tyr Phe Asp Tyr Trp Gly Gln Gly Thr Thr Leu Thr Val Ser Ser
        115                 120                 125

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 74

Gln Ile Val Leu Thr Gln Ser Pro Ala Ile Met Ser Ala Ser Pro Gly
1               5                   10                  15

Glu Lys Val Thr Ile Ser Cys Ser Ala Thr Ser Ser Val Ile Phe Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Tyr Gln Ser Tyr Pro Leu Thr
                85                  90                  95

Phe Gly Gly Gly Thr Lys Leu Glu Leu Lys Arg
            100                 105

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ile Val Leu Thr Gln Ser Pro Ala Ile Met Ser Ala Ser Pro Gly
1               5                   10                  15

Glu Arg Val Thr Ile Ser Cys Ser Ala Ser Ser Ser Val Ile Phe Leu
            20                  25                  30

Tyr Trp Tyr Gln Gln Lys Pro Gly Ser Ser Pro Lys Pro Arg Ile Tyr
        35                  40                  45

Arg Thr Ser Asn Leu Ala Ser Gly Val Pro Asp Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Leu Lys Arg
            100                 105

<210> SEQ ID NO 76
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Lys Asp Val Leu Val Val Pro Ala Ala Pro Tyr Tyr Tyr Gly
                100                 105                 110

Met Asp Val Trp Gly Gln Gly Thr Thr Val Thr Val Ser Ser
            115                 120                 125

<210> SEQ ID NO 77
<211> LENGTH: 98
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 78
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (99)..(108)
<223> OTHER INFORMATION: Any amino acid
<220> FEATURE:
<221> NAME/KEY: MOD_RES
<222> LOCATION: (110)..(111)
<223> OTHER INFORMATION: Any amino acid
<220> FEATURE:
<221> NAME/KEY: MOD_RES
<222> LOCATION: (113)..(114)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (123)..(123)
<223> OTHER INFORMATION: Any amino acid

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Xaa Xaa Xaa Xaa Xaa Xaa Xaa Xaa Tyr Xaa Xaa Tyr
            100                 105                 110

Xaa Xaa Asp Xaa Trp Gly Gln Gly Thr Thr Xaa Thr Val Ser Ser
        115                 120                 125

<210> SEQ ID NO 79
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Met or Gln
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (13)..(13)
<223> OTHER INFORMATION: Lys or Gln
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (40)..(40)
<223> OTHER INFORMATION: Thr or Ala
<220> FEATURE:
<221> NAME/KEY: MOD_RES
<222> LOCATION: (42)..(42)
<223> OTHER INFORMATION: Glu or Gly
<220> FEATURE:
<221> NAME/KEY: MOD_RES
<222> LOCATION: (44)..(44)
<223> OTHER INFORMATION: Arg or Gly
<220> FEATURE:
<221> NAME/KEY: MOD_RES
<222> LOCATION: (49)..(49)
<223> OTHER INFORMATION: Ala or Ser
<220> FEATURE:
<221> NAME/KEY: MOD_RES
<222> LOCATION: (75)..(75)
<223> OTHER INFORMATION: Ala or Ser
<220> FEATURE:
<221> NAME/KEY: MOD_RES
<222> LOCATION: (80)..(80)
<223> OTHER INFORMATION: Phe or Tyr
<220> FEATURE:
<221> NAME/KEY: MOD_RES
<222> LOCATION: (84)..(84)
<223> OTHER INFORMATION: Ser or Asn
<220> FEATURE:
<221> NAME/KEY: MOD_RES
<222> LOCATION: (88)..(88)
<223> OTHER INFORMATION: Ser or Ala
<220> FEATURE:
<221> NAME/KEY: MOD_RES
<222> LOCATION: (97)..(97)
<223> OTHER INFORMATION: Val or Ala
<220> FEATURE:
<221> NAME/KEY: MOD_RES
<222> LOCATION: (98)..(98)
```

```
<223> OTHER INFORMATION: Arg or Lys
<220> FEATURE:
<221> NAME/KEY: MOD_RES
<222> LOCATION: (123)..(123)
<223> OTHER INFORMATION: Leu or Val

<400> SEQUENCE: 79

Glu Val Xaa Leu Xaa Glu Ser Gly Gly Gly Leu Val Xaa Pro Gly Gly
1               5                   10                  15

Ser Leu Xaa Leu Ser Cys Ala Ala Ser Gly Phe Thr Phe Ser Asn Tyr
            20                  25                  30

Ala Met Ser Trp Val Arg Gln Xaa Pro Xaa Lys Xaa Leu Glu Trp Val
        35                  40                  45

Xaa Thr Ile Ser Ser Gly Gly Tyr Thr Tyr Tyr Pro Asp Ser Leu
    50                  55                  60

Lys Gly Arg Phe Thr Ile Ser Arg Asp Asn Xaa Lys Asn Thr Leu Xaa
65                  70                  75                  80

Leu Gln Met Xaa Ser Leu Arg Xaa Glu Asp Thr Ala Val Tyr Tyr Cys
                85                  90                  95

Xaa Xaa His Gly Ala Pro Met Thr Thr Val Ile Thr Tyr Ala Pro Tyr
            100                 105                 110

Tyr Phe Asp Tyr Trp Gly Gln Gly Thr Thr Xaa Thr Val Ser Ser
        115                 120                 125

<210> SEQ ID NO 80
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Asn Val Leu Thr Gln Ser Pro Ala Ile Met Ser Ala Ser Leu Gly
1               5                   10                  15

Glu Lys Val Thr Met Asn Cys Arg Ala Ser Ser Ser Val Lys Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Thr Ser Pro Tyr Thr
                85                  90                  95

Phe Gly Gly Gly Thr Lys Leu Glu Ile Lys
            100                 105

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30
```

```
Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Tyr Thr Phe Gly Gly Gly Thr Lys Leu Glu Ile Lys
                100                 105
```

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (30)..(31)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (91)..(94)
<223> OTHER INFORMATION: Any amino acid

<400> SEQUENCE: 82

```
Asp Xaa Val Leu Thr Gln Ser Pro Ala Ile Met Ser Ala Ser Pro Gly
 1               5                  10                  15

Glu Lys Val Thr Met Thr Cys Arg Ala Ser Ser Ser Val Xaa Xaa Tyr
                 20                  25                  30

Leu Tyr Trp Tyr Gln Gln Lys Ser Asp Ala Ser Pro Lys Leu Trp Ile
             35                  40                  45

Tyr Tyr Thr Ser Asn Leu Ala Ser Gly Val Pro Ala Arg Phe Ser Gly
 50                  55                  60

Ser Gly Ser Gly Thr Ser Tyr Ser Leu Thr Ile Ser Ser Xaa Glu Ala
 65                  70                  75                  80

Glu Asp Ala Ala Thr Tyr Tyr Cys Gln Gln Xaa Xaa Xaa Xaa Pro Tyr
                 85                  90                  95

Thr Phe Gly Gly Gly Thr Lys Leu Glu Ile Lys
                100                 105
```

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Asn, Val or Ile

```
<220> FEATURE:
<221> NAME/KEY: MOD_RES
<222> LOCATION: (4)..(4)
<223> OTHER INFORMATION: Leu or Met
<220> FEATURE:
<221> NAME/KEY: MOD_RES
<222> LOCATION: (10)..(10)
<223> OTHER INFORMATION: Ile or Phe
<220> FEATURE:
<221> NAME/KEY: MOD_RES
<222> LOCATION: (11)..(11)
<223> OTHER INFORMATION: Met or Leu
<220> FEATURE:
<221> NAME/KEY: MOD_RES
<222> LOCATION: (13)..(13)
<223> OTHER INFORMATION: Ala or Val
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (21)..(21)
<223> OTHER INFORMATION: Met or Ile
<220> FEATURE:
<221> NAME/KEY: MOD_RES
<222> LOCATION: (22)..(22)
<223> OTHER INFORMATION: Asn or Thr
<220> FEATURE:
<221> NAME/KEY: MOD_RES
<222> LOCATION: (39)..(39)
<223> OTHER INFORMATION: Ser or Pro
<220> FEATURE:
<221> NAME/KEY: MOD_RES
<222> LOCATION: (40)..(40)
<223> OTHER INFORMATION: Asp or Gly
<220> FEATURE:
<221> NAME/KEY: MOD_RES
<222> LOCATION: (41)..(41)
<223> OTHER INFORMATION: Ala or Gln
<220> FEATURE:
<221> NAME/KEY: MOD_RES
<222> LOCATION: (42)..(42)
<223> OTHER INFORMATION: Ser or Ala
<220> FEATURE:
<221> NAME/KEY: MOD_RES
<222> LOCATION: (59)..(59)
<223> OTHER INFORMATION: Ala or Ser
<220> FEATURE:
<221> NAME/KEY: MOD_RES
<222> LOCATION: (69)..(69)
<223> OTHER INFORMATION: Ser or Asp
<220> FEATURE:
<221> NAME/KEY: MOD_RES
<222> LOCATION: (71)..(71)
<223> OTHER INFORMATION: Ser or Thr
<220> FEATURE:
<221> NAME/KEY: MOD_RES
<222> LOCATION: (72)..(72)
<223> OTHER INFORMATION: Leu or Phe
<220> FEATURE:
<221> NAME/KEY: MOD_RES
<222> LOCATION: (77)..(77)
<223> OTHER INFORMATION: Met, Leu or Val
<220> FEATURE:
<221> NAME/KEY: MOD_RES
<222> LOCATION: (79)..(79)
<223> OTHER INFORMATION: Gly or Ala

<400> SEQUENCE: 83

Xaa Xaa Val Xaa Thr Gln Ser Pro Ala Xaa Xaa Ser Xaa Xaa Xaa Gly
1               5                   10                  15

Glu Lys Val Thr Xaa Xaa Cys Arg Ala Ser Ser Ser Val Lys Tyr Met
                20                  25                  30
```

```
Tyr Trp Tyr Gln Gln Lys Xaa Xaa Xaa Xaa Pro Lys Leu Trp Ile Tyr
            35              40                  45

Tyr Thr Ser Asn Leu Ala Pro Gly Val Pro Xaa Arg Phe Ser Gly Ser
    50              55              60

Gly Ser Gly Asn Xaa Tyr Xaa Xaa Thr Ile Ser Ser Xaa Glu Xaa Glu
65              70              75              80

Asp Ala Ala Thr Tyr Tyr Cys Gln Gln Phe Thr Thr Ser Pro Tyr Thr
            85              90                  95

Phe Gly Gly Gly Thr Lys Leu Glu Ile Lys Arg
            100             105
```

US 8,435,522 B2

HUMANIZED ANTIBODIES AGAINST CXCR3

CROSS-REFERENCE TO RELATED APPLICATIONS

This application is a National Phase of International Patent Application Ser. No. PCT/US2008/052356, filed on Jan. 29, 2008, which claims priority to U.S. Provisional Patent Application No. 60/898,709, filed Feb. 1, 2007. The contents of these applications are incorporated herein by reference in their entirety.

BACKGROUND

The interaction between chemokines and their receptors is an important step in the control of leukocyte migration. Chemokines also mediate a variety of effects independent of chemotaxis, including induction and enhancement of cell-associated cytokine responses.

The human cell surface protein CD183 is a G protein-coupled receptor with selectivity for three chemokines including IP10 (interferon-g-inducible 10 kDa protein), Mig (monokine induced by interferon-g) and I-TAC (interferon-inducible T cell a-chemoattractant). These three chemokines belong to the structural subfamily of "CXC" chemokines, in which a single amino acid residue separates the first two of four highly conserved Cys residues. Historically, CD183 is the third CXC chemokine receptor discovered and, therefore, CD183 is commonly designated as "CXCR3." Binding of chemokines to CXCR3 induces cellular responses that are involved in leukocyte traffic, most notably integrin activation, cytoskeletal changes and chemotactic migration. CXCR3 is expressed on effector/memory T cells and/or in T cells present in many types of inflamed tissues (e.g., T-helper 1 cells or Th1 cells and CD8+ Tc1 cells). In addition, IP10, Mig and I-TAC are commonly produced by local cells in inflammatory lesions, suggesting that CXCR3 and its chemokines participate in the recruitment of white blood cells to sites of inflammation. Therefore, CXCR3 is a target for the development of antibodies and antagonists, which may be used in the treatment and diagnosis of diverse inflammatory and immune diseases and disorders, such as rheumatoid arthritis, multiple schlerosis, Crohn's disease, inflammatory bowel disease, chronic obstructive pulmonary disease, psoriasis, type 1 diabetes and transplant rejection. Because CXCR3 is expressed on a subset of B-cell lymphomas, CXCR3 may also be a target for treating and diagnosing lymphomas and leukemias.

SUMMARY

Disclosed are antigen-binding polypeptide molecules that bind specifically to the chemokine receptor CXCR3 (see GenBank gi:4504099). The polypeptides include a humanized heavy chain variable region and a humanized light chain variable region. For example, the polypeptides may include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 90% humanized (preferably at least about 95% humanized, more preferably at least about 98% humanized, and even more preferably at least about 100% humanized), excluding the CDRs. The antigen-binding polypeptides molecules may be derived from monoclonal antibody donors (e.g., mouse monoclonal antibody donors) and may include CDRs from the monoclonal antibodies (e.g., mouse monoclonal CDRs). The polypeptides may function as antagonists for the CXCR3 receptor.

In some embodiments, the antigen-binding polypeptide binds specifically to CXCR3, and includes: (a) a humanized antibody heavy chain variable region comprising: (1) a CDR-H1 comprising an amino acid sequence of (NYMAS (SEQ ID NO: 1)); (2) a CDR-H2 comprising an amino acid sequence of (TISSGGGYTYYPDSLKG (SEQ ID NO: 2)); and (3) a CDR-H3 comprising an amino acid sequence of (HGAPMTTVITYAPYYF{D,Y}Y (SEQ ID NO: 3)); and (b) a humanized antibody light chain variable region comprising: (1) a CDR-L1 comprising an amino acid sequence of (RASSSVKYMY (SEQ ID NO: 4)); (2) a CDR-L2 comprising an amino acid sequence of (YTSNLAP (SEQ ID NO: 5)); and (3) a CDR-L3 comprising an amino acid sequence of (QQFTTSPYT (SEQ ID NO: 6)). The polypeptide may include a CDR-H3 comprising an amino acid sequence of (HGAPMTTVITYAPYYFYY (SEQ ID NO: 7)).

In some embodiments of the polypeptides, (1) the CDR-H1 consists of the amino acid sequence of (NYMAS (SEQ ID NO: 1)); (2) the CDR-H2 consists of the amino acid sequence of (TISSGGGYTYYPDSLKG (SEQ ID NO: 2)); (3) the CDR-H3 consists of the amino acid sequence of (HGAPMTTVITYAPYYF{D,Y}Y (SEQ ID NO: 3)); (4) the CDR-L1 consists of the amino acid sequence of (RASSSVKYMY (SEQ ID NO: 4)); (5) the CDR-L2 consists of the amino acid sequence of (YTSNLAP (SEQ ID NO: 5)); and (6) the CDR-L3 consists of the amino acid sequence of (QQFTTSPYT (SEQ ID NO: 6)). For example, the CDR-H3 may consist of the amino acid sequence of (HGAPMTTVITYAPYYFYY (SEQ ID NO: 7)).

In some embodiments, the polypeptide comprises a humanized antibody heavy chain variable region of ({E,D}{I,N,V}V{L,M}TQSPA{T,F,I}{L,M}S{L,A,V}{S,T}{L,P}GE{R,K}{A,V}T{L,M,I}{S,T, N}CRASSSVKYMY WYQQK{S,P}{G,D}{Q,A}{A,S}P{R,K}L{L,W}I{Y,K} YTSNLAPG {I,V}P{A,S}RFSGSGSG{T, N}{D,S}{F, Y}{T,S}{L,F}TISS{M,L}E{A,G,P}ED{F,A}A{V, T}YYC{Q,Y}QFTT{S,Y}PYTFGGGTKLEI KR (SEQ ID NO: 8)). For example, the polypeptide may comprise a humanized antibody heavy chain variable region of (EVQLLESGGGLVQPGGSLRLSCAASGFTFSNYAMS WVRQAPKGLEWVVSTISSGGGYTYYPDSLKG RFTISRDNSKNTLYLQMNSLRAEDTAVYYCAK HGAPMTTVITYAPYYFYYWGQGTTVTV SS (SEQ ID NO: 9)). In some embodiments, the polypeptide comprises a humanized antibody light chain variable region of (E{I,N}VLTQSPA{T,F,I}{L,M}S{L,A,V}{S,T}{L,P}GE{R,K}{A,V}T{L,M,I}{S,T,N}CRASSSVKYMYW YQQK{S,P}{G,D}{Q,A}{A,S}P{R,K}L{L,W}IYYTSNLAP G{I,V}P{A,S}RFSGSGSG{T,N}{D,S}{F,Y}{T,S}{L,F}TISS{M,L}E{A,G}ED{F,A}A{V,T}YYC QQFTTSPYTFGGGTKLEIKR (SEQ ID NO: 10)). For example, the polypeptide may comprise a humanized antibody light chain variable region of (EIVLTQS-PATLSLSLGERATLSCRASSSVKYMYWYQQKSGQ APRLLIYYTSNLAPGIPARFSGS GSGTDFTLTISSME-AEDFAVYYCQQFTTSPYTFGGGTKLEIKR (SEQ ID NO: 11)); or (ENVLTQSPAFLSVTPGEKVTITC RASSSVKYMYWVYQQKPDQAPKLWIY YTSNLAPGVPSRFS GSGSGNDYTFTISSLE-AEDAATYYCQQFTTSPYTFGGGTKLEIKR (SEQ ID NO: 12)).

Also disclosed are humanized antibody heavy chain variable regions. The humanized antibody heavy chain region may comprise: (1) a CDR-H1 comprising an amino acid sequence of ({N,S,Y}YAMS (SEQ ID NO: 13)); (2) a CDR-H2 comprising an amino acid sequence of ({T,A,Y}I{S,Y}{S,G,T,Y}{G,Y}G,S}{G,Y}G{F,S,Y}TYY{P,A}DS{L,Y,V}KG (SEQ ID NO: 14)); and (3) a CDR-H3 comprising an amino acid sequence of {H,Y}{G,Y}{A,Y}PM{T,Y}T{V,Y}ITY{A,Y}PYYFYY (SEQ ID NO: 15)). For example, the humanized antibody heavy chain variable region may comprise an amino acid sequence of (EVQLLESGGG LVQPGGSLRLSCAASGFTFS{N,S,Y}YAMSWVVRQ APGKGLEWVS{T,A,Y}I{S,Y }{S,G,T,Y}{G,S}{G,Y} G{F,S,Y}TYY{P,A}DS{L,Y,V}KGRFTISRDNSKNTLYLQMNSLRAEDTAVY YCAK{H,Y}{G,Y}{A,Y}PM{T,Y}T{V,Y}ITY{A,Y}PYYFYY WGQGTTVTVSS (SEQ ID NO: 16)).

In another example, a humanized antibody heavy chain variable region comprises: (1)a CDR-H1 comprising an amino acid sequence of (NYAIS (SEQ ID NO: 17)); (2) a CDR-H2comprising an amino acid sequence of (TYSSGGVYTYYRDSLKG (SEQ ID NO: 18)); and (3) a CDR-H3 comprising an amino acid sequence of (HGAAMTTVITYAPFYFYY (SEQ ID NO: 19)). For example, the humanized antibody heavy chain variable region may comprise an amino acid sequence of (EVQLLESGGGLVQPGGSLRLSCAASGFTFSNYAIS WVRQAPGKGLEWVSTYSSGGVYTYYRDSLKGR FTISRDNSKNTLYLQMNSLRAEDTAVYYCAK HGAAMTTVITYAPFYFYYWGQGTTVT VSS (SEQ ID NO: 20)).

In another example, a humanized antibody heavy chain variable region comprises: (1)a CDR-H1 comprising an amino acid sequence of (YYAMS (SEQ ID NO: 21)); (2) a CDR-H2comprising an amino acid sequence of (TIYSGGSYTFYPDSLEG (SEQ ID NO: 22)); and (3) a CDR-H3 comprising an amino acid sequence of (HGAPMSTEITYAPYYFYY (SEQ ID NO: 23)).

For example, the humanized antibody heavy chain variable region may comprise an amino acid sequence of (EVQLLESGGGLVQPGGSLRLSCAASGFTFS YYAMSWVRQAPGKGLEWVSTIYSGGSYTFYPD SLEGRFTISRDNSKNTLYLQMNSLRAEDTAVYYCAK HGAPMSTEITYAPYYFYYWGQGTTVT VSS (SEQ ID NO: 24)).

In another example, a humanized antibody heavy chain variable region comprises: (1) a CDR-H1 comprising an amino acid sequence of (NYAMS (SEQ ID NO: 25)); (2) a CDR-H2comprising an amino acid sequence of (TIYSGGGYTFYLDSLKG (SEQ ID NO: 26)); and (3) a CDR-H3 comprising an amino acid sequence of (HSYPMTTVITYAPYYFYY (SEQ ID NO: 27)). For example, the humanized antibody heavy chain variable region may comprise an amino acid sequence of (EVQLLESGGGLVQPGGSLRLSCAASGFTFSNYYMS WVRQAPGKGLEWVSTIYSGGGYTFYLDSLKG RFTISRDNSKNTLYLQMNSLRAEDTAVYYCAK HSYPMTTVITYAPYYFYYWGQGTTVT VSS (SEQ ID NO: 28)).

In another example, a humanized antibody heavy chain variable region comprises: (1)a CDR-H1 comprising an amino acid sequence of (NYAMS (SEQ ID NO: 25)); (2) a CDR-H2comprising an amino acid sequence of (TISSGGGYTYYPDSLKG (SEQ ID NO: 2)); and (3) a CDR-H3 comprising an amino acid sequence of (HGAPMTTVITYAPYYFYY (SEQ ID NO: 7)). For example, thehumanized antibody heavy chain variable region may comprise an amino acid sequence of (EVQLLESGGGLVQPGGSL-RLSCAASGFTFSNYAMSWVRQAPGKGLEWVS TISSGGGYTYYPDSLKGRFTISRDNSKNTLYLQMNS LRAEDTAVYYCAKHGAPMTTVITYAPYYFYY WGQGTTVT VSS (SEQ ID NO: 29)).

In another example, a humanized antibody heavy chain variable region comprises:(1) a CDR-H1 comprising an amino acid sequence of (NYAMS (SEQ ID NO: 25)); (2) a CDR-H2comprising an amino acid sequence of (TISSGGGYTYYPDSLKG (SEQ ID NO: 2)); and (3) a CDR-H3 comprising an amino acid sequence of (HGAPMTTVITYAPYYFYY (SEQ ID NO: 7)). For example, the humanized antibody heavy chain variable region may comprise an amino acid sequence (EVQLLESGGGLVQPGGSL-RLSCAASGFTFSNYAMSWVRQAPGKGLEWVS TISSGGGYTYYPDSLKGRFTISRDNSKNTLYLQMNSL RAEDTAVYYCAKHGAPMTTVITYAPYYFYY WGQGTTVT VSS (SEQ ID NO: 29)).

Also disclosed are humanized antibody light chain variable regions. The humanized antibody light chain region may comprise: (1) a CDR-L1 comprising an amino acid sequence of (RASSSVKYMY (SEQ ID NO: 4)); (2) a CDR-L2 comprising an amino acid sequence of (YTSNLAP (SEQ ID NO: 5)); and (3) a CDR-L3 comprising an amino acid sequence of (QQFTTSPYT (SEQ ID NO: 6)). For example, the humanized antibody light chain variable region may comprise an amino acid sequence of (EIVLTQSPATLSLSLGERATLSC RASSSVKYMYWYQQKSGQAPRLLIY YTSNLAPGIPARFSGS GSGTDFTLTISSMEAED-FAVYYCQQFTTSPYTFGGGTKLEIKR (SEQ ID NO: 11)).

In another example, a humanized antibody light chain variable region comprises: (1) a CDR-L1 comprising an amino acid sequence of (RASSSVKYMY (SEQ ID NO: 4)); (2) a CDRL2 comprising an amino acid sequence of (YTSNLAP (SEQ ID NO: 5)); and (3) a CDR-L3comprising an amino acid sequence of (QQFTTSPYT (SEQ ID NO: 6)). For example, the humanized antibody light chain variable region may comprise an amino acid sequence of (EIVLTQS-PATLSLSPGERATLSC RASSSVKYMYWVYQQKPGQAPRLLIY YTSNLAPGIPARFSGS GSGTDFTLTISSLEPED-FAVYYCQQFTTSPYTFGGGTKLEIKR (SEQ ID NO: 30)).

In another example, a humanized antibody light chain variable region comprises: (1) a CDR-L1 comprising an amino acid sequence of (RASSSVKYMY (SEQ ID NO: 4)); (2) a CDRL2 comprising an amino acid sequence of (YTSNLAP (SEQ ID NO: 5)); and (3) a CDR-L3comprising an amino acid sequence of (YQFTTSPYT (SEQ ID NO: 31)). For example, the humanized antibody light chain variable region may comprise an amino acid sequence of (EIVLTQS-PATLSLSPGERATLSC RASSSVKYMYWYQQKPGQAPRLLIY YTSNLAPGIPARFSGS GSGTDFTLTISSLEPED-FAVYYCYQFTTSPYTFGGGTKLEIKR (SEQ ID NO: 32)).

In another example, the humanized antibody light chain variable region comprises: (1) a CDR-L1 comprising an amino acid sequence of (RASSSVKYMY (SEQ ID NO: 4)); (2) a CDR-L2 comprising an amino acid sequence of (YTSN-LAP (SEQ ID NO: 5)); and (3) a CDR-L3comprising an amino acid sequence of (QQYTTSPYT (SEQ ID NO: 33)). For example, the humanized antibody light chain variable region may comprise an amino acid sequence of (EIVLTQS-PATLSLSPGERATLSC RASSSVKYMYWYQQKPGQAPRLLIY YTSNLAPGIPARFSGS GSGTDFTLTISSLEPEDFAVYY-CQQYTTSPYTFGGGTKLEIKR (SEQ ID NO: 34)).

In another example, the humanized antibody light chain variable region comprises: (1)a CDR-L1 comprising an amino acid sequence of (RASSSVKYMY (SEQ ID NO: 4)); (2) a CDR-L2 comprising an amino acid sequence of (YTSNLAP (SEQ ID NO: 5)); and (3) a CDR-L3comprising an amino acid sequence of ((QQFTTYPYT (SEQ ID NO: 35)). For example, the humanized antibody light chain variable region may comprise an amino acid sequence of (EIVLTQSPATLSLSPGERATLSC RASSSVKYMYWYQQKPGQAPRLLIY YTSNLAPGIPARFSGS GSGTDFTLTISSLEPED-FAVYYCQQFTTYPYTFGGGTKLEIKR (SEQ ID NO: 36)).

In another example, the humanized antibody light chain variable region comprises: (1) a CDR-L1 comprising an amino acid sequence of (RAS{S,Q}SV{K,S}SY{M,L}{Y,A} (SEQ ID NO: 37); (2) a CDR-L2 comprising an amino acid sequence of ({Y,D}{T,A}SN{L,R}A{P,T}); and (3) a CDR-L3 comprising an amino acid sequence of (Q,Y}Q{F,Y}TT{S,Y}PYT (SEQ ID NO: 38)). For example, the humanized antibody light chain variable region may comprise an amino acid sequence of (EIVLTQSPATLSLSPGERATLSC RAS{S,Q}SV{K,S}SY{M,L}{Y,A}WYQQKPGQAP RLLIY{Y,D}{T,A}SN{L,R}A{P,T}GIPARFSGSGSGTD FTLTISSLEPEDFAVYYC{Q,Y}Q{F,Y}TT{S,Y}PYT FGGG TKLEIKR (SEQ ID NO: 39)).

In another example, the humanized antibody light chain variable region comprises: (1)a CDR-L1 comprising an amino acid sequence of (RASSSVKYMY (SEQ ID NO: 4)); (2) a CDR-L2 comprising an amino acid sequence of (YTSNLAP (SEQ ID NO: 5)); and (3) a CDR-L3comprising an amino acid sequence of (QQFTTSPYT (SEQ ID NO: 6)). For example, the humanized antibody light chain variable region may comprise an amino acid sequence of (ENVLTQS-PAFLSVTPGEKVTIT CRASSSVKYMYWYQQKPDQAPKLWIY YTSNLAPGVPSRFS GSGSGNDYTFTISSLE-AEDAATYYCQQFTTSPYTFGGGTKLEIKR (SEQ ID NO: 12)).

In another example, the humanized antibody light chain variable region comprises: (1)a CDR-L1 comprising an amino acid sequence of (RAS{S,Q}SV{K,S}SY{M,L}{Y,A} (SEQ ID NO: 37); (2) a CDR-L2 comprising an amino acid sequence of ({Y,D}{T,A}SN{L,R}A{P,T} (SEQ ID NO: 40)); and (3) a CDR-L3 comprising an amino acid sequence of (Q,Y}Q{F,Y}TT{S,Y}PYT (SEQ ID NO: 38)). For example, the humanized antibody light chain variable region may comprise an amino acid sequence of ((E,D)(N,V)V(L,M)TQSPAFLSVTPGEKVTITCRASSSVKYMYWYQQK PDQAPKL(W,L)I(Y,K)YTSNLAPGVPSRFSGSGSG(N,T) D(Y,F)TFTISSLEAEDAATYYC(Q,Y)Q(F,Y)TT(S,Y)PYT FGGGT KLEIKR (SEQ ID NO: 41)).

The aforementioned humanized heavy chains and humanized light chains may be present in the antigen binding polypeptides that binds specifically to CXCR3.

The antigen-binding polypeptide may be selected from the group consisting of an antibody molecule, a Fab fragment, a Fab' fragment, a F(ab')$_2$ fragment, and an scFv molecule. In some embodiments, polypeptide is an antibody molecule. Antibody molecules may include chimeric antibodies that include a human heavy chain constant region and a human light chain constant region. For example, the antibody molecule may be an IgG molecule (e.g., a IgG1 or an IgG4 molecule), where the polypeptide includes the heavy chain and light chain constant domains of an IgG molecule. The polypeptide may be an scFv molecule. For example, the scFv may have a formula selected from the group consisting of NH$_2$-L-VH-X-VK-COOH and NH$_2$-L-VK-X-VH-COOH; wherein L is a leader sequence; VH is the humanized antibody heavy chain variable region; X is a linking polypeptide; and VK is the humanized antibody light chain variable region.

The antigen-binding polypeptide further may be conjugated or fused to a therapeutic or diagnostic agent. For example, therapeutic agents may be selected from the group consisting of a cytotoxic agent, a radioactive label, an immunomodulator, a hormone, an enzyme, an oligonucleotide, a photoactive therapeutic agent or a combination thereof. Examples of diagnostic agents may include a radioactive label, a photoactive diagnostic agent, an ultrasound-enhancing agent or a non-radioactive label.

The antigen-binding polypeptide may be an antagonist of CXCR3. Typically, the polypeptide is not an agonist of CXCR3.

The antigen-binding polypeptide binds to the CXCR3 receptor with specificity and high affinity. Typically, the polypeptide binds to CXCR3 with an affinity constant of at least about $10^6 M^{-1}$ (preferably at least about $10^7 M^{-1}$, more preferably at least about $10^8 M^{-1}$, even more preferably at least about $10^9 M^{-1}$).

Also disclosed are pharmaceutical compositions comprising the aforementioned antigen-binding polypeptides and a carrier (e.g., a diluent or excipient). The pharmaceutical may further comprise an additional therapeutic or diagnostic agent as disclosed herein.

Also disclosed are methods of treating or diagnosing a disease or condition that comprise administering the disclosed pharmaceutical compositions to a patient in need thereof. For example, the pharmaceutical compositions may be administered to treat or diagnose an inflammatory, immune, and/or malignant disease or condition. Examples of diseases and conditions may include autoimmune disease (e.g., lupus), inflammatory bowel disease (IBD), chronic obstructive pulmonary disease (COPD), arthritis (e.g., rheumatoid arthritis), multiple sclerosis, transplant rejection, central nervous system injury, Crohn's disease, psoriasis, type 1 diabetes and leukemia or lymphoma (e.g., chronic lymphocytic leukemia (CLL)).

Also disclosed are polynucleotides that encode the aforementioned polypeptides. The polynucleotides may be operably linked to a promoter for expressing the encoded polypeptides in a suitable host cell. As such, methods of producing the polypeptide encoded by the recombinant polynucleotide may include: a) culturing a cell transformed with the recombinant polynucleotide to express the encoded polypeptide; and b) recovering the polypeptide so expressed.

BRIEF DESCRIPTION OF THE DRAWINGS

Figure 7:
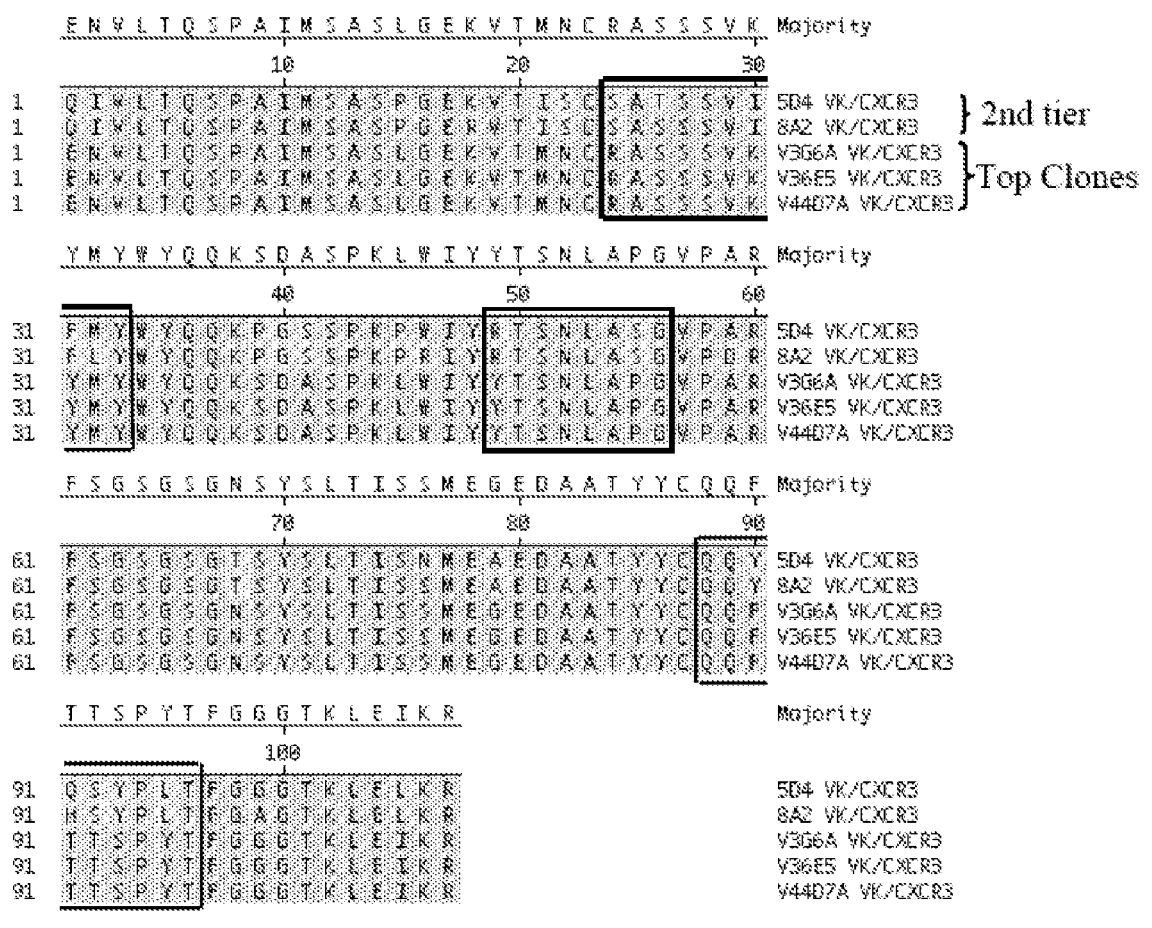

FIG. 7 illustrates an alignment of the VK Domains of 5 anti-CXCR3 Clones (SEQ ID NOS 74-75, 53, 53 and 53, respectively, in order of appearance. The Majority sequence is disclosed as SEQ ID NO: 53).

FIG. 8 illustrates an alignment of the VH Domain of anti-CXCR3 Clone V44D7 with the closest expressed human IgG and germline VH (SEQ ID NOS 51 and 76-77, respectively, in order of appearance. The Majority sequence is disclosed as SEQ ID NO: 78).

Figure 10:
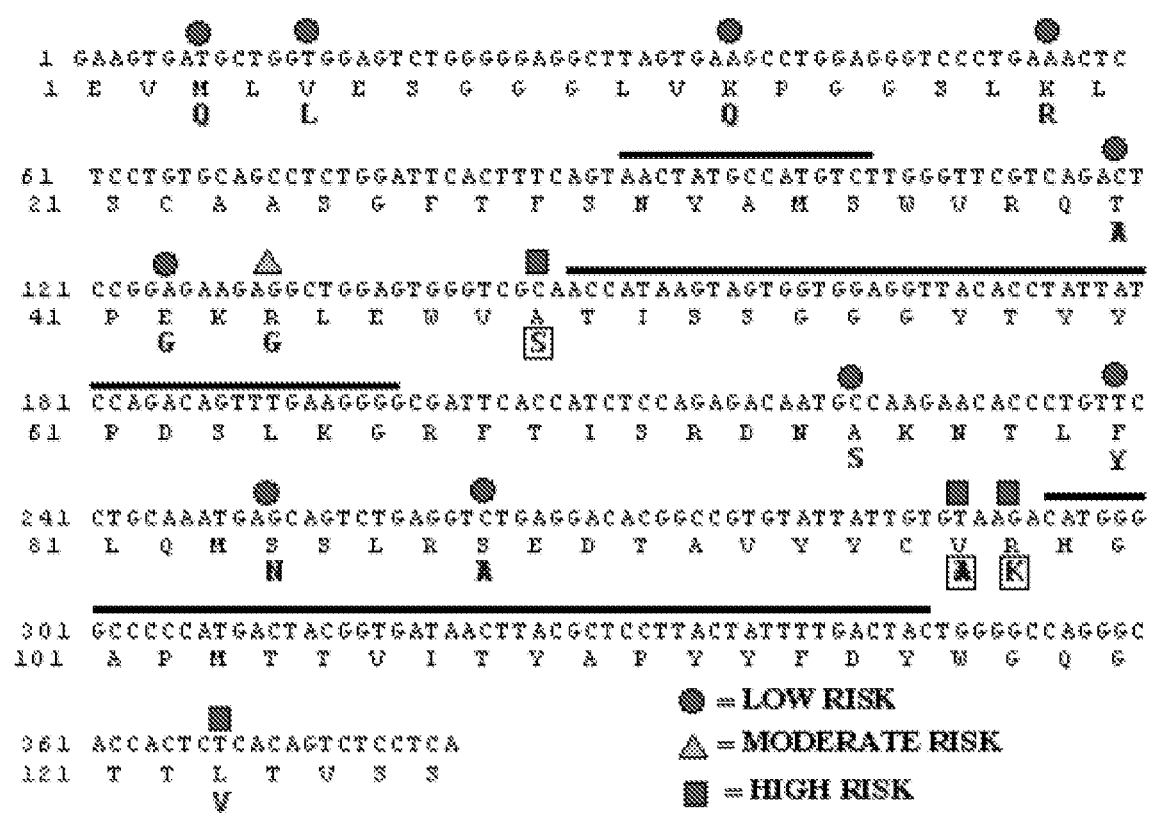

FIG. 10 illustrates the risk assessment of amino acid changes required for complete humanization of the VH domain of anti-CXCR3 clone V44D7. The required amino acid changes are indicated below the main sequence and were derived from an alignment to human VH3-23. The germline gene and an expressed antibody are described in GenBank accession no. AAD53829. The nucleotide sequence disclosed as SEQ ID NO: 50 and the amino acid sequence disclosed as SEQ ID NO: 79.

FIG. 11 illustrates an alignment of the VK domain of anti-CXCR3 clone V3G6 with the closest expressed human IgG and germiline VK (SEQ ID NOS 80-81 and 45, respectively, in order of appearance. The Majority sequence is disclosed as SEQ ID NO: 82).

DETAILED DESCRIPTION OF THE PREFERRED EMBODIMENTS

Definitions

Figure 1:
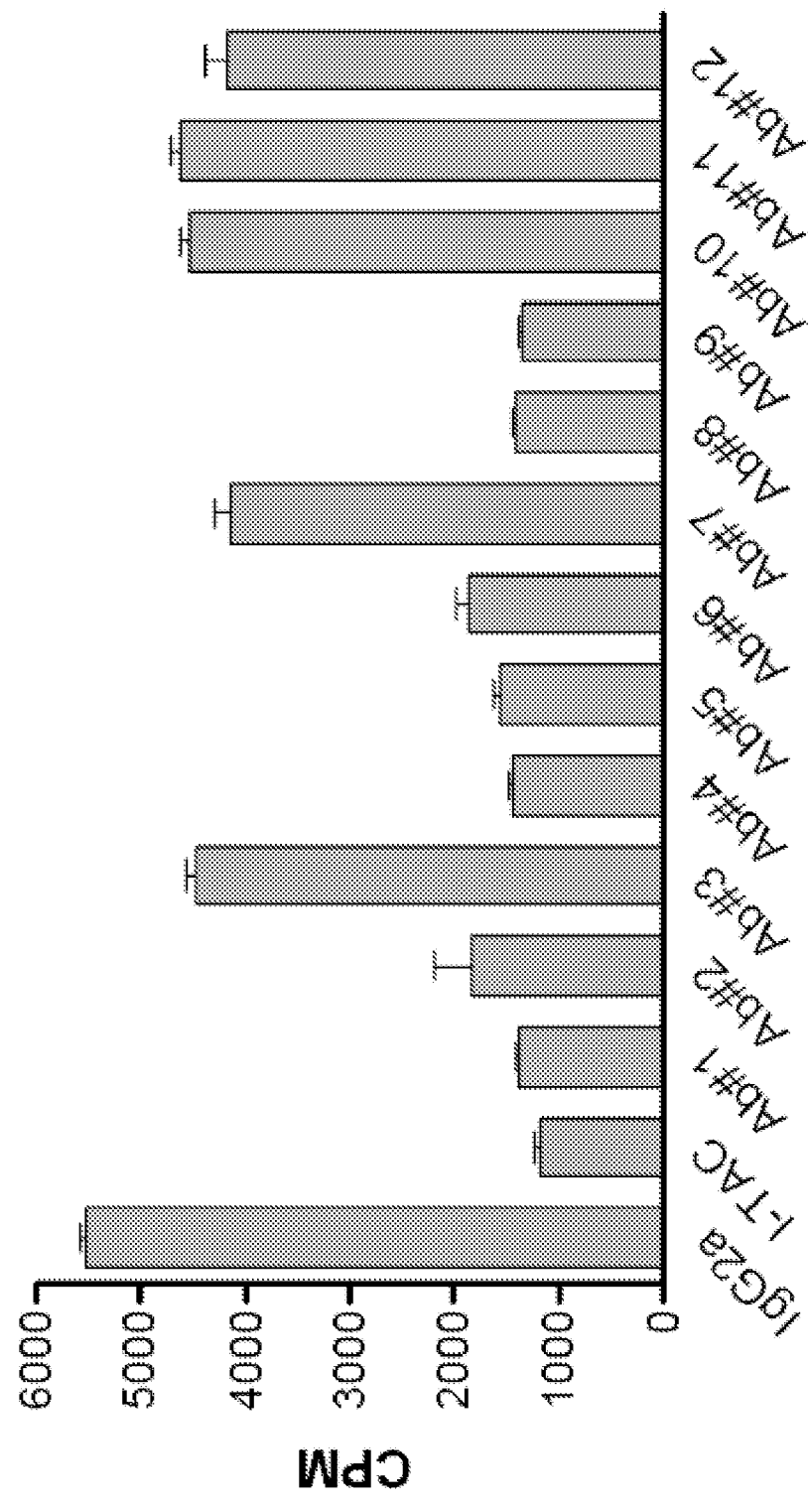
FIG. 1 illustrates inhibition of 125I-IP-10 binding to Th1 cells by murine anti-CXCR3mAb. Ab#1-5D4A; Ab#2-8A5A; Ab#3-19G2; Ab#4-V36E5A; Ab#5-V44D7A; Ab#6-37B5A; Ab#7-21A4A; Ab#8-V15F4A; Ab#9-V3G6A; Ab#10-23E12A; Ab#11-35C4; Ab#12-39E10.
Figure 2:
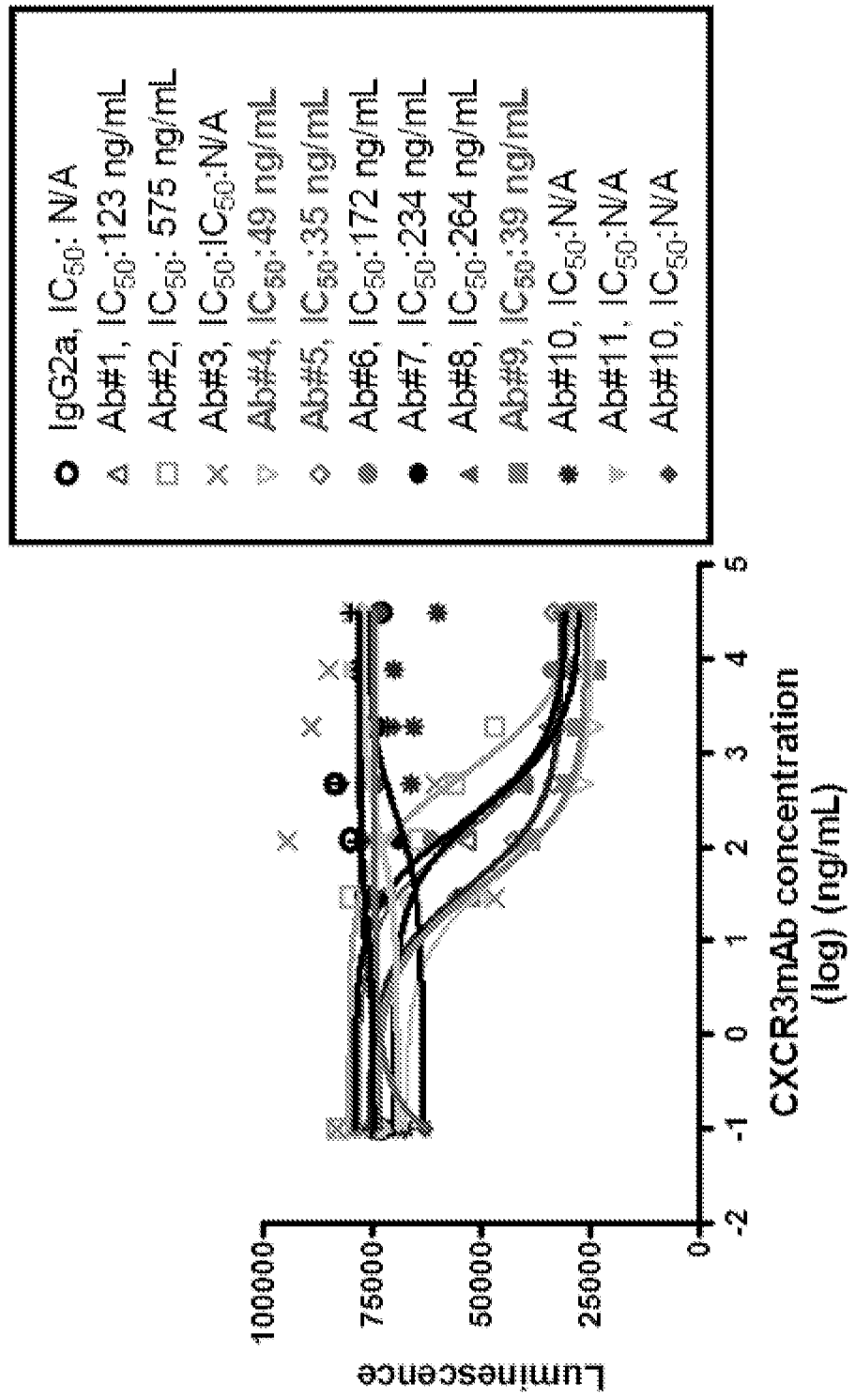
FIG. 2 illustrates inhibition of IP-10-induced Th1 cell migration by murine anti-CXCR3mAb. Ab#1-5D4A; Ab#2-8A5A; Ab#3-19G2; Ab#4-V36E5A; Ab#5-V44D7A; Ab#6-37B5A; Ab#7-21A4A; Ab#8-V15F4A; Ab#9-V3G6A; Ab#10-23E12A.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A humanized antibody is a recombinant protein in which the CDRs from an antibody from one species, e.g., a rodent antibody, are transferred from the heavy and light variable chains of the rodent antibody into human heavy and light variable domains or heavy and light variable domains that have been mutagenized to include at least a portion of the amino acid sequence of the human heavy and light variable domains (as represented by "percent humanization"). The constant domains of the antibody molecule may be derived from those of a human antibody.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

As used herein, "CDR" means a "complementarity determining region" that is present in a variable domain of an antibody heavy chain (VH) or a variable domain of an antibody light chain (VL or VK). Each variable domain includes three CDRs which are designated CDR-H1, CDR-H2, and CDR-H3, for those present in the heavy chain variable domain, and CDR-L1, CDR-L2, and CDR-L3 for those present in the light chain variable domain. The Kabat numbering system is used herein. As such, CDR-H1 begins at approximately amino acid 31 (i.e., approximately 9 residues after the first cysteine residue), includes approximately 5-7 amino acids, and ends at the next tyrosine residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tyrosine residue. CDR-L2 begins at approximately the sixteenth residue after the end of CDR-L1 and includes approximately 7 residues. CDR-L3 begins at approximately the thirty third residue after the end of CDR-L2; includes approximately 7-11 residues and ends at the sequence F-G-X-G, where X is any amino acid.

The antigen-binding polypeptides disclosed herein may be conjugated or fused to a therapeutic agent, which may include radioactive labels, an immunomodulator, a hormone, a photoactive therapeutic agent, a cytotoxic agent, which may be a drug or a toxin, and a combination thereof. Drugs may include those drugs that possess the pharmaceutical property selected from the group consisting of antimitotic, antikinase, alkylating, antimetabolite, antibiotic, alkaloid, antiangiogenic, apoptotic agents and combinations thereof. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, anthracyclines, taxanes, and their analogs, and a combination thereof. The toxins encompassed by the present invention may be selected from the group consisting of ricin, abrin, alpha toxin, saporin, ribonuclease (RNase), e.g., onconase, DNase I, Staphylococcal enterotoxin-A, pokeweed antiviral protein, gelonin, diphtherin toxin, Pseudomonas exotoxin, and Pseudomonas endotoxin.

Immunomodulators may be selected from the group consisting of a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF)), interferon, such as interferons-alpha, -beta, or -gamma, and stem cell growth factor, such as designated "S1 factor". More specifically, immunomodulators may include IL-1, IL-2, IL-3, IL-6, IL-10, IL-12, IL-18, IL-21 interferon-gamma, TNF-alpha or a combination thereof.

The antigen-binding polypeptides disclosed herein may be conjugated or fused to a diagnostic agent. Diagnostic agents may include photoactive diagnostic agents or radiolabels having an energy between 60 and 4,000 keV, or a non-radioactive label. The radioactive label is preferably a gamma-, beta-, and positron-emitting isotope and is selected from the group consisting of $^{125}I$, $^{131}I$, $^{123}I$, $^{124}I$, $^{86}Y$, $^{186}Re$, $^{188}Re$, $^{62}Cu$, $^{64}Cu$, $^{111}In$, $^{67}Ga$, $^{68}Ga$, $^{99m}Tc$, $^{94m}Tc$, $^{18}F$, $^{11}C$, $^{13}N$, $^{15}O$, $^{76}Br$ and combinations thereof. Diagnostic agents may include contrast agents, for example, such as manganese, iron or gadolinium.

EXAMPLES

Isolation of Murine IgG$_1$,k CXCR-3 Binding Antibody Using the Hybridoma Technology BALB/c mice were immunized with CXCR-3 expressing NSO cells. In a typical procedure 5×10$^6$ cells in 50 ul of RIBI adjuvant (Sigma) were injected into rear footpads (25 ul per pad). Two additional injections in RIBI adjuvant were given at 2 week intervals followed by a final boost in PBS. Three days later mice were sacrificed, their poplietal lymph nodes were harvested and lymphocytes isolated for fusion. Lymphocytes were fused with P3X63Ag8.653 plasmacytoma cells at 5:1 ratio using PEG/DMSO (Sigma) as a fusion agent. After fusion cells were resuspended in selective HAT media and seeded at 10$^6$ cells per well in 96 well plates. The supernatants from hybridomas that survived HAT selection were screened by ELISA for the presence of mouse IgG. The IgG producing hybridomas were identified and their supernatants were further screened by FACS analysis for antibodies binding to CXCR3 expressing NSO cells (CXCR3$^+$NSO). The hybridomas identified as positives for CXCR3$^+$NSO cell binding were then screened for differential binding to CXCR3$^+$NSO and PC-NSO (vector control) cells in order to identify CXCR3 specific clones. The CXCR3 specific hybridomas were subcloned twice by limiting dilutions. Hybridoma subclones were expanded in serum-free medium, the antibodies were purified on Protein-A column and further characterized in order to pick the lead candidate.

Humanization Strategy

One goal in humanizing the anti-CXCR3 antibodies was to obtain 60-80% humanized VH and VK domains that retain 90-100% of original binding affinity and specificity. Site-directed mutagenesis of individual high risk positions in VH and VK was used to further humanize the antibodies while maintaining binding affinity and specificity.

Humanization was performed by CDR grafting and structure based analysis and variable region resurfacing. (See Jones et al, NATURE (1986) May 29-June 4; 321(6069):522-5; Roguska et al., PROTEIN ENGINEERING, 1996, 9(10):895-904; and Xoma, Humanizing Mouse Antibody Frameworks While Preserving 3-D Structure. PROTEIN ENGINEERING, 1994, Vol. 7, pg 805). The primary antibody sequence and 3-D structure data were utilized to identify key framework residues required to maintain the binding affinity and specificity. The 3-D structures of nine (9) different Fab and IgG molecules were analyzed (human and mouse, with or without ligand). After aligning the mouse anti-CXCR3 V44 VH and VK to the nearest human germline genes, the amino acid at every position was evaluated for potential influence on binding and immunogenicity. This information was used to assign a low, moderate, or high risk value for mutation at each position. In general, only the low and moderate risk positions were mutated while avoiding the high risk positions.

The heavy chain was 98% humanized relative to the mouse heavy chain (excluding CDR's) after this process. An affinity maturation strategy was then performed by incorporating tyrosines pair wise at each position in CDR3, including a Y115D substitution, which gave on average a 2-fold increase in affinity. The heavy chain that was used in the 2 lead candidates included 2 additional mutations at positions 97 and 98 making it 100% human, excluding the CDR's. Following the same strategy for the light chain, the VK was aligned to the A14 germline gene and low and moderate risk positions were mutated. After determining that this germline gene appears to be rarely expressed in normal humans, the process was repeated using the L6 germline as template The "Blast for Ig sequences" website sponsored by the NCBI was used to identify the closest match to the mouse VH and VK region used in the study. The V-base website at the MRC was used to confirm the human germline sequences.

Human germline VH and VK genes were chosen as the best matches to the mouse sequence VH and VK sequences. For the mouse VH sequence, the human germline sequence VH3-23 (as designated in V-base) was identified as the best match: VH3-23 germline (EVQLLESGGGLVQPGGSL-RLSCAASGFTFSSYAMSWVRQAPGK-GLEQVSAISGSGGSTYYA DSVKGRFTISRDNSKNT-LYLQMNSLRAEDTAVYYCAK (SEQ ID NO: 43)). For the mouse VK sequence, the human germline sequence A14 and L6 (as designated in V-base) were identified as the best matches: L6 Germline (EIVLTQSPATLSLSPGER-ATLSCRASQSVSSYLAWYQQK-PGQAPRLLIYDASNRATGIPARFSG SGSGTD-FTLTISSLEPEDFAVYYCQQRSNWP (SEQ ID NO: 44)); and A14 Germline (DVVMTQSPAFLSVTPGEKVTITC-QASEGIGNYLYWYQQKPDQAPKLLIK-YASQSISGVPSRFS GSGSGTDFTFTISSLEAEDAATYY-CQQGNKHP (SEQ ID NO: 45)). Cloning and Sequencing of Murine anti-CXCR3 VH and VK domains from Hybridoma Cell Lines Hybridoma cells were pelleted, washed 3× with PBS and RNA extracted using Trizol reagent (Invitrogen, Cat. No. 15596-026) following the manufacturers protocol. Total RNA was converted to cDNA using a 5' RACE kit (Rapid Amplification of cDNA Ends, Invitrogen, Cat. No. 18374-058) following the manufacturers protocol. Briefly, RNA was ligated to random hexamer primer, Random N6, and 1$^{st}$ strand cDNA generated using superscript TI RNAase H negative reverse transcriptase. The cDNA was purified using a Glass-Max spin cartridge provided with the kit and then reacted with TdT (terminal deoxynucleotidyl transferase) in the presence of dCTP to append the cDNA with C basepairs at the 5' end. The dC-tailed cDNA was PCR amplified using an anchor primer specific for the dC tail and a gene specific primer that hybridizes to highly conserved DNA sequence in the mouse constant heavy 1 (CH1) for VH and constant kappa (CK) for VK. The resulting PCR product was analyzed by gel electrophoresis for correct size corresponding to intact VH or VK domain then purified and ligated in to a Topo TA vector (Invitrogen Cat. No. 45-0071) following manufacturers protocol. After transformation in to bacteria DNA was prepared from clones containing correct size insert and the DNA sequence determined using a Big Dye terminator sequencing reaction mix (Applied Biosystems, Part No. 4336699) and a 3700 ABI/Prism DNA analyzer following manufacturers protocol.

Humanizing Murine Anti-CXCR3 Antibodies

First, a single lead murine anti-CXCR3 antibody, V44D7, was identified based on binding data and sequence data generated as described above. The amino acid sequence of the VH and VK domains from this antibody were aligned to all known human germline VH and VK domains using currently available public databases (i.e., Blast for IgG at the NCBI and V-base at the MRC). By focusing on alignment within the framework regions a highly homologous human germline VH domain, VH3-23, and 2 different human germline VK domains, A14 and L6, were identified. At those positions in the framework where the mouse sequence differed from the human germline, an iterative process was used to convert or mutate the mouse framework so it matched the corresponding human germline framework. In addition, certain residues in CDR3 of both the VH and VK were mutated by replacement with tyrosine (i.e., affinity matured) to potentially help compensate for any losses in affinity due to the framework residues changes. The affinity matured and humanized mouse VH and VK domains were generated by a polymerase chain reaction process using a panel of overlapping synthetic DNA oligonucleotides. As part of the synthetic gene design process a codon optimization strategy was used, that is to say the triplet code for each amino acid that is preferentially utilized by mammalian cells for gene expression was incorporated at each position. The synthetic VH and VK domains were cloned in to specialized mammalian expression vectors that allowed the corresponding domains to be expressed in the context of a fully human IgG1, G4 or Kappa antibody backbone. Small-scale production of the humanized antibodies was achieved by co-tranfection of an IgG1 or G4 construct with the Kappa construct in to 293F cells with lipofectamine (Invitrogen) following manufactures protocol. Supernatants from the transient transfections were passed through Protein A or G resin and the IgG purified to homogeneity for testing in cell based assays.

Epitope Competition Studies

Figure 13:
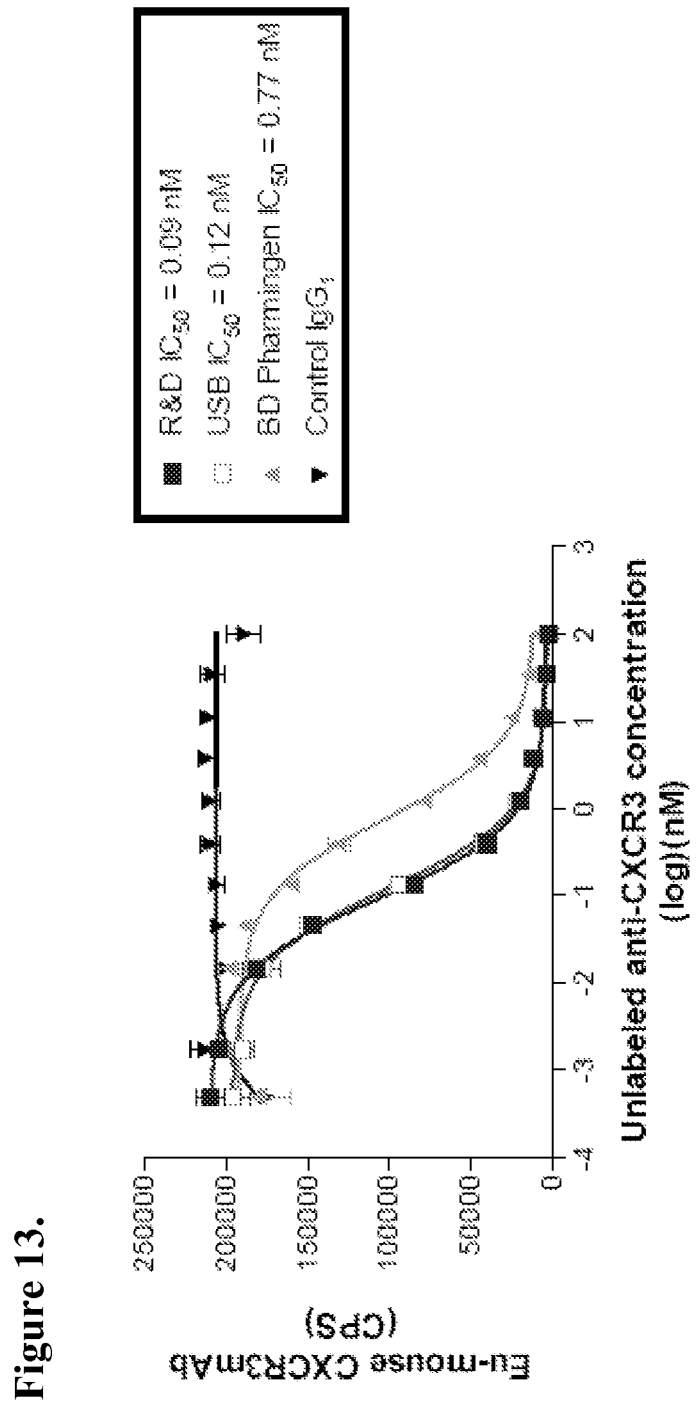
FIG. 13 illustrates inhibition of mouse CXCR3mAb binding to CXCR3+ NSO cells by commercial CXCR3mAbs. Approximately 0.5 nM Eu-CXCR3mAb was incubated with CXCR3 transfected NSO cells in the presence of various concentrations of unlabeled commercial CXCRmAbs. A dose-dependent inhibition of Eu-CXCR3mAb binding to CXCR3+ NSO cells was observed.

Various commercial CXR3mAbs were tested in a competitive binding assay using Europium (Eu) labeled -mouse CXCR3mAb. CXCR3mAbs from various commercial sources inhibited Eu-CXCR3mAb binding to CXCR3. This data indicated that mouse CXCR3mAb and commercial antibodies bind to overlapping epitopes on CXCR3 (FIG. 13).

Antibody Affinities

Binding affinity and activity of mouse and humanized CXCR3mAbs were determined by various competitive binding assays using $^{125}$I- and Eu-labeled chemokines and Eu-labeled CXCR3mAb and Th1 chemotaxis assays including: $^{125}$I-CXCL10 binding assay; $^{125}$I-CXCL11 binding assay; Eu-CXCL10 binding assay; Th1 chemotaxis assay; and Eu-mouse CXCR3mAb binding assay.

Th1 Cells

Figure 14:
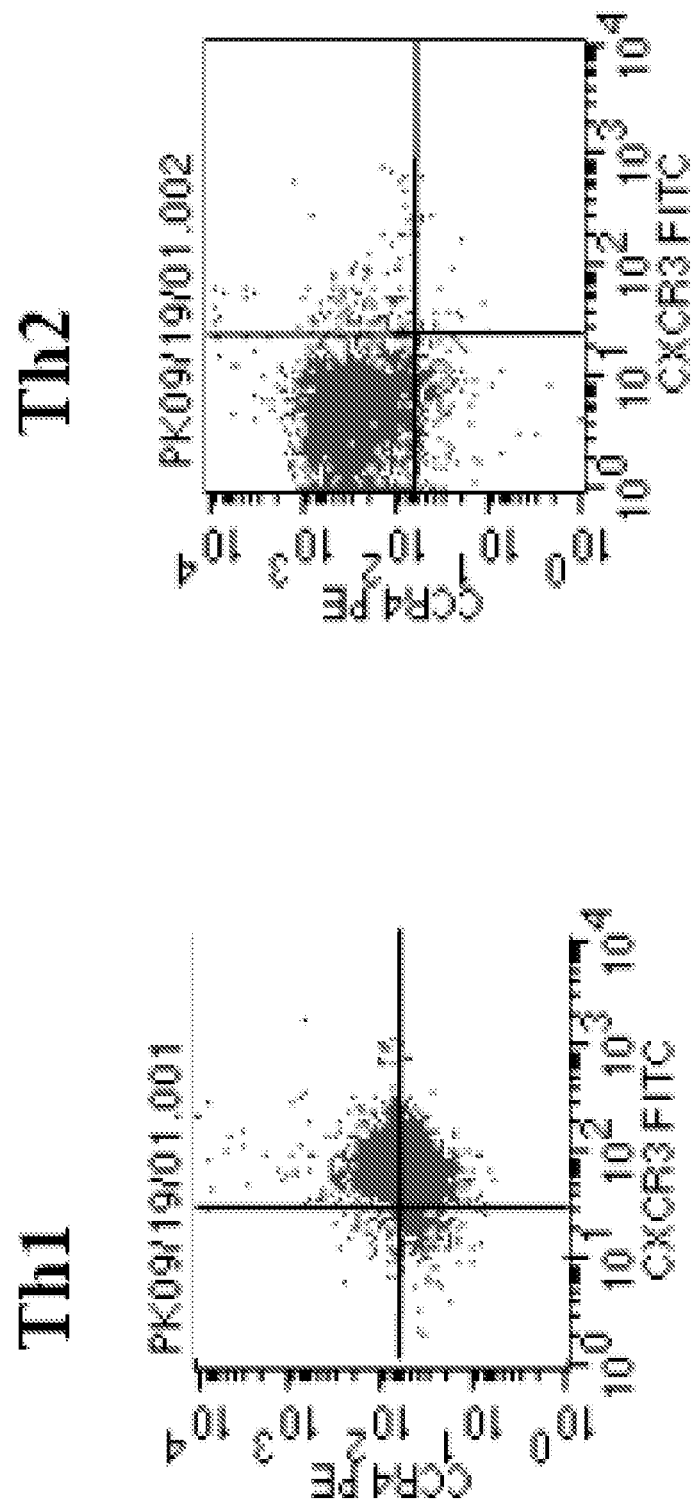
FIG. 14 illustrates expression of CXCR3 on Th1 cells. Th1 and Th2 cells were generated from cord blood and CXCR3 and CCR4 expression were determined by FACS. CXCR3 was present only Th1 cells.
Figure 15:
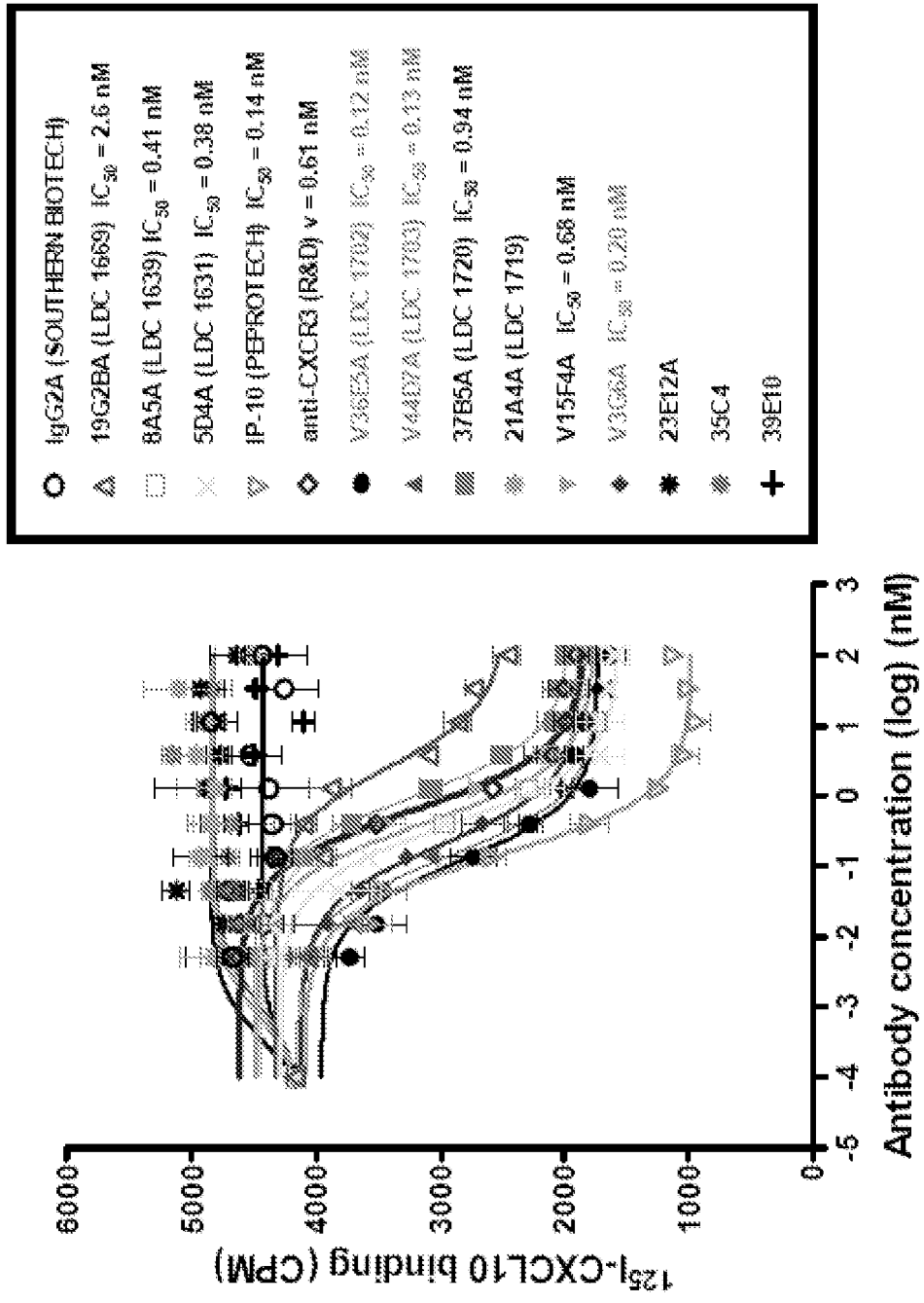
FIG. 15 illustrates an $^{125}$I-CXCL10 binding assay. Th1 cells were incubated in a 96 well plate with $^{125}$I-CXCL10 in the absence or presence of various concentrations CXCRm-Abs. Cell bound $^{125}$I-CXCL10 was separated from free radioactivity by an oil column and counted using a gamma counter. IC$_{50}$ values were calculated using Prizm software. Lead candidates were highlighted in green.
Figure 16:
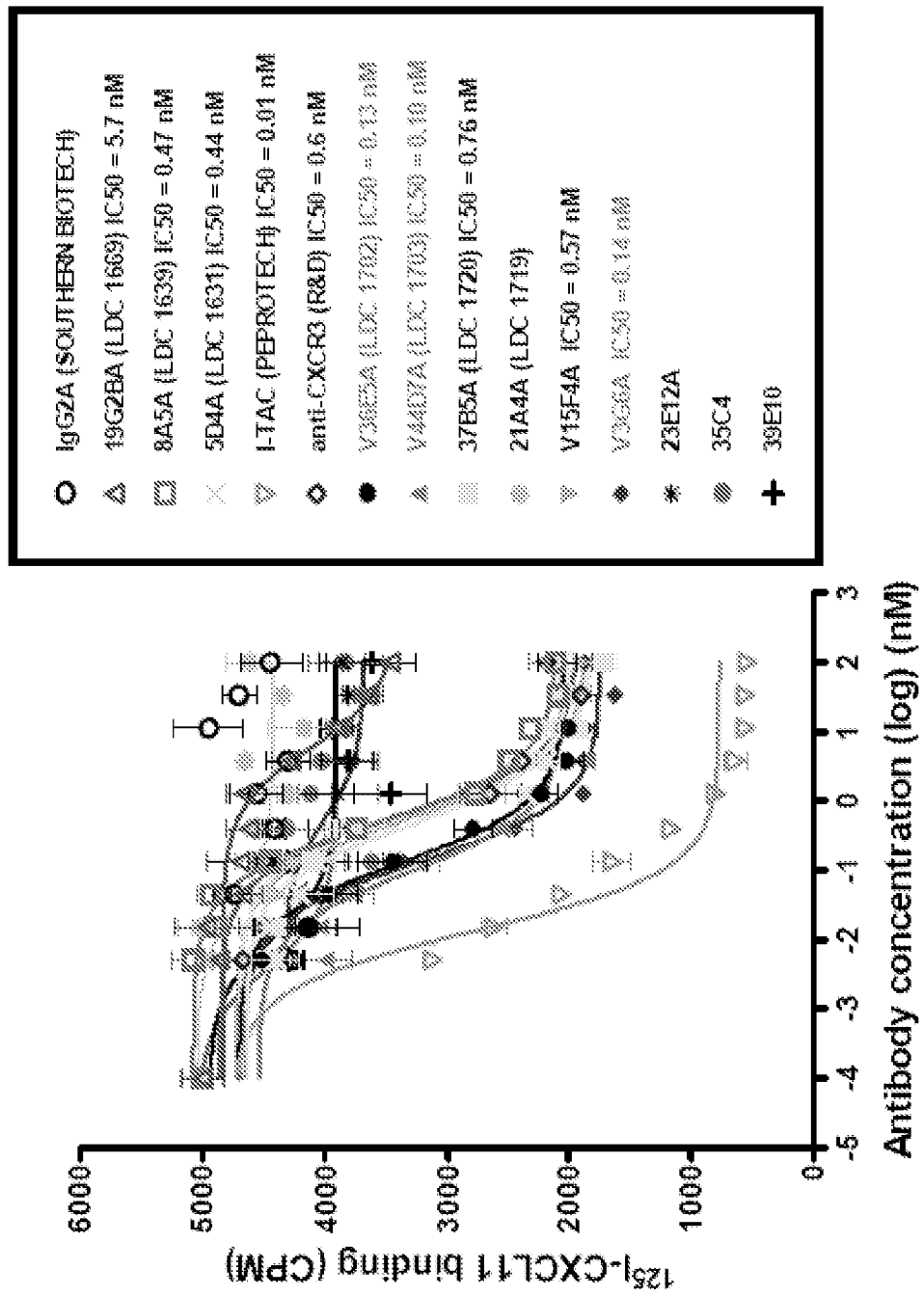
FIG. 16 illustrates an $^{125}$I-CXCL11 binding assay. Th1 cells were incubated in a 96 well plate with $^{125}$I-CXCL11 in the absence or presence of various concentrations CXCRm-Abs. Cell bound $^{125}$I-CXCL11 was separated from free radioactivity by an oil column and counted using a gamma counter. IC$_{50}$ values were calculated using Prizm software. Lead candidates were highlighted in green.

Primary Th1 cells generated from cord blood were used for all binding assays. As described in the literature, CXCR3 expression was observed only on Th1 cells but not on Th2 cells as determined by FACS analysis (FIG. 14). Th2 cells specifically expressed CCR4.

$^{125}$I-CXCL10 and $^{125}$I-CXCL11 Binding Assays

The binding affinity of mouse CXCR3mAb antibodies was determined based on their ability to inhibit radiolabeled CXCL10 and CXCL11 binding to Th1 cells (FIGS. 15, 16, 18, and 19 and Table 1). Based on these binding studies and the chemotaxis assay, three mouse CXCRmAbs were selected for further study.

TABLE 1

Characterization of Anti-CXCR3 mAbs

| | Binding to Th1 cells, FACS | Inhibition of IP-10-induced Th1 chemotaxis, IC$_{50}$ (ng/mL) | Displacement of $^{125}$I-IP-10 binding to Th1 cells (IC$_{50}$, nM) | Displacement of $^{125}$I-I-Tac binding to Th1 cells by (IC$_{50}$, nM) |
|---|---|---|---|---|
| IgG2 a | 4.02 | N/A | N/A | N/A |
| Ab#1 | 1498 | 123 | 0.38 | 0.44 |
| Ab#2 | 1215 | 575 | 0.41 | 0.47 |
| Ab#3 | 681 | N/A | 2.6 | 5.7 |
| Ab#4 | 1262 | 49 | 0.12 | 0.13 |
| Ab#5 | 1119 | 35 | 0.13 | 0.10 |
| Ab#6 | 831 | 172 | 0.94 | 0.76 |
| Ab#7 | 4.20 | N/A | N/A | — |
| Ab#8 | 1096 | 264 | 0.68 | 0.57 |
| Ab#9 | 1348 | 39 | 0.20 | 0.14 |
| Ab#10 | 66.84 | N/A | N/A | — |
| Ab#11 | 4.80 | N/A | — | — |
| Ab#12 | 5.77 | N/A | N/A | — |
| R&D mAb | N/D | 351 | 0.61 | 0.6 |

Ab#1 - 5D4A;
Ab#2 - 8A5A;
Ab#3 - 19G2;
Ab#4 - V36E5A;
Ab#5 - V44D7A;
Ab#6 - 37B5A;
Ab#7 - 21A4A;
Ab#8 - V15F4A;
Ab#9 - V3G6A;
Ab#10 - 23E12A;
Ab#11 - 35C4;
Ab#12 - 39E10.

Eu-CXCRmAb Saturation Binding Assay

Figure 17:
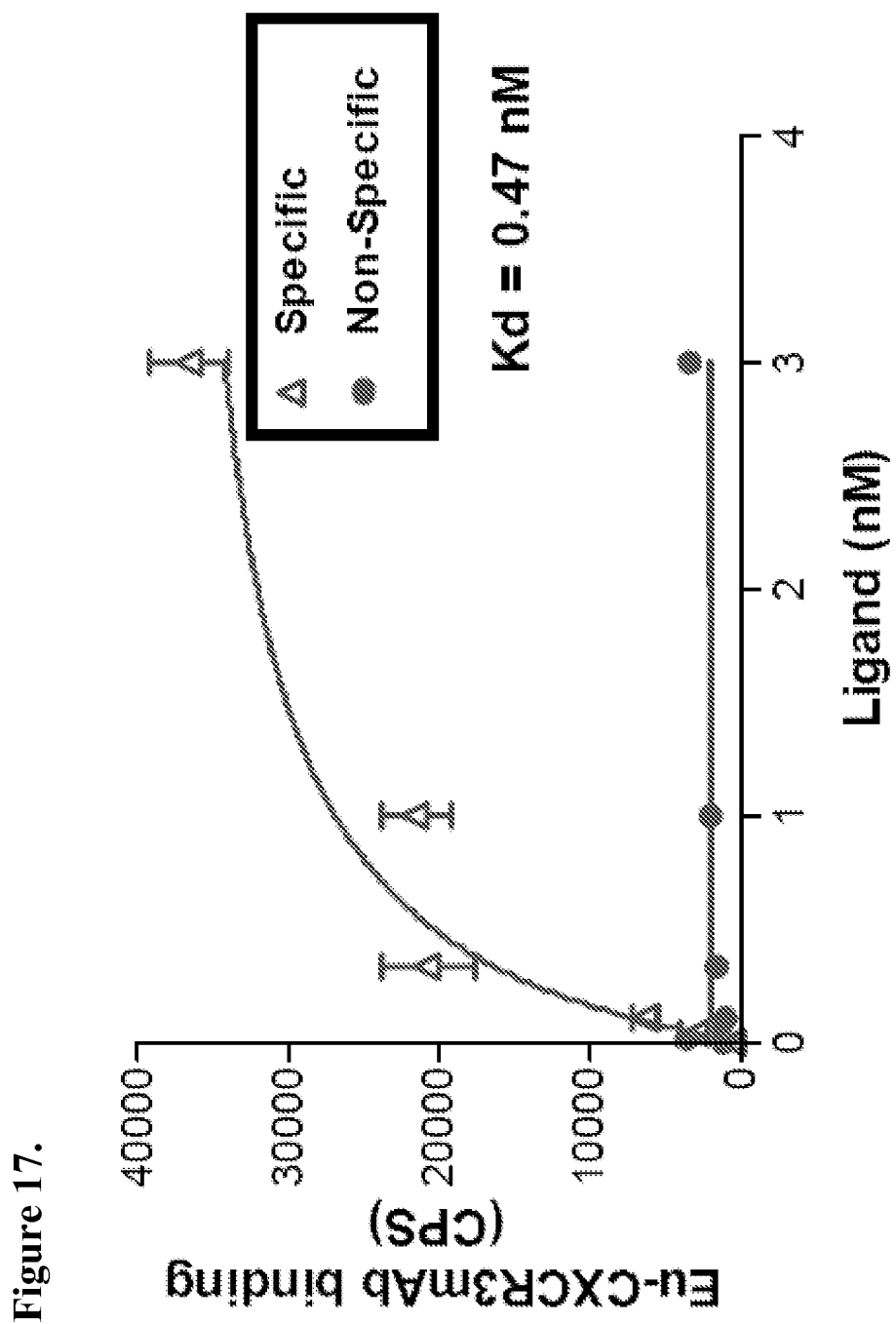
FIG. 17 illustrates Eu-CXCR3mAb binding to Th1 cells. Th1 cells were incubated with increasing concentrations of Eu-CXCR3mAb in the absence or presence 10-fold excess of unlabeled CXCR3mAb. After incubation (1 hr at RT), cell bound Eu-CXCR3mAb was separated from free Europium by washing three times and the plate was read using Vctor2 fluorometer.
Figure 18:
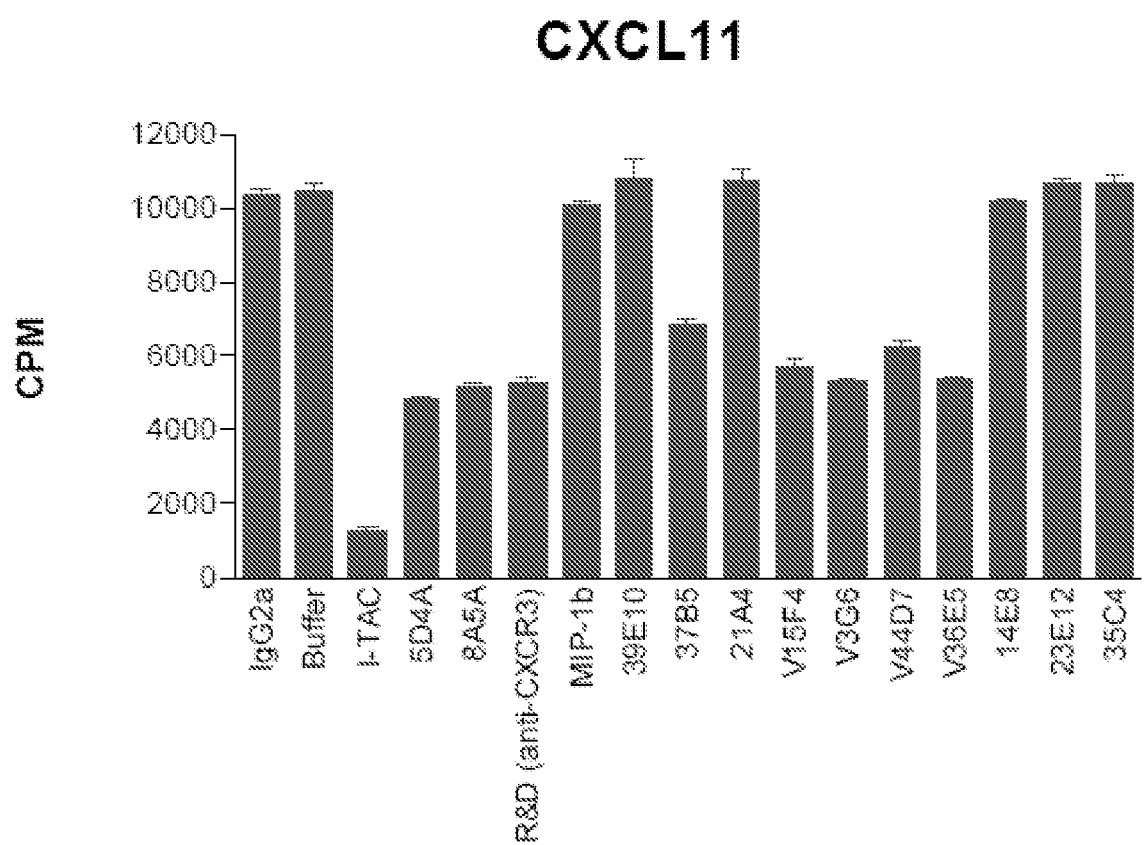
FIG. 18 illustrates inhibition of $^{125}$I-CXCL11 binding to Th1 by CXCR3mAb hybridoma supernatants. Th1 cells were incubated in a 96 well plate with $^{125}$I-CXCL11 in the absence or presence of various CXCRmAb hybridoma supernatants for 1 hr at RT. Cell bound $^{125}$I-ligands were separated from free radioactivity by an oil column and counted using a gamma counter. Seven hybridoma supernatants that inhibited CXCL11 binding to Th1 cells were selected for further development.
Figure 19:
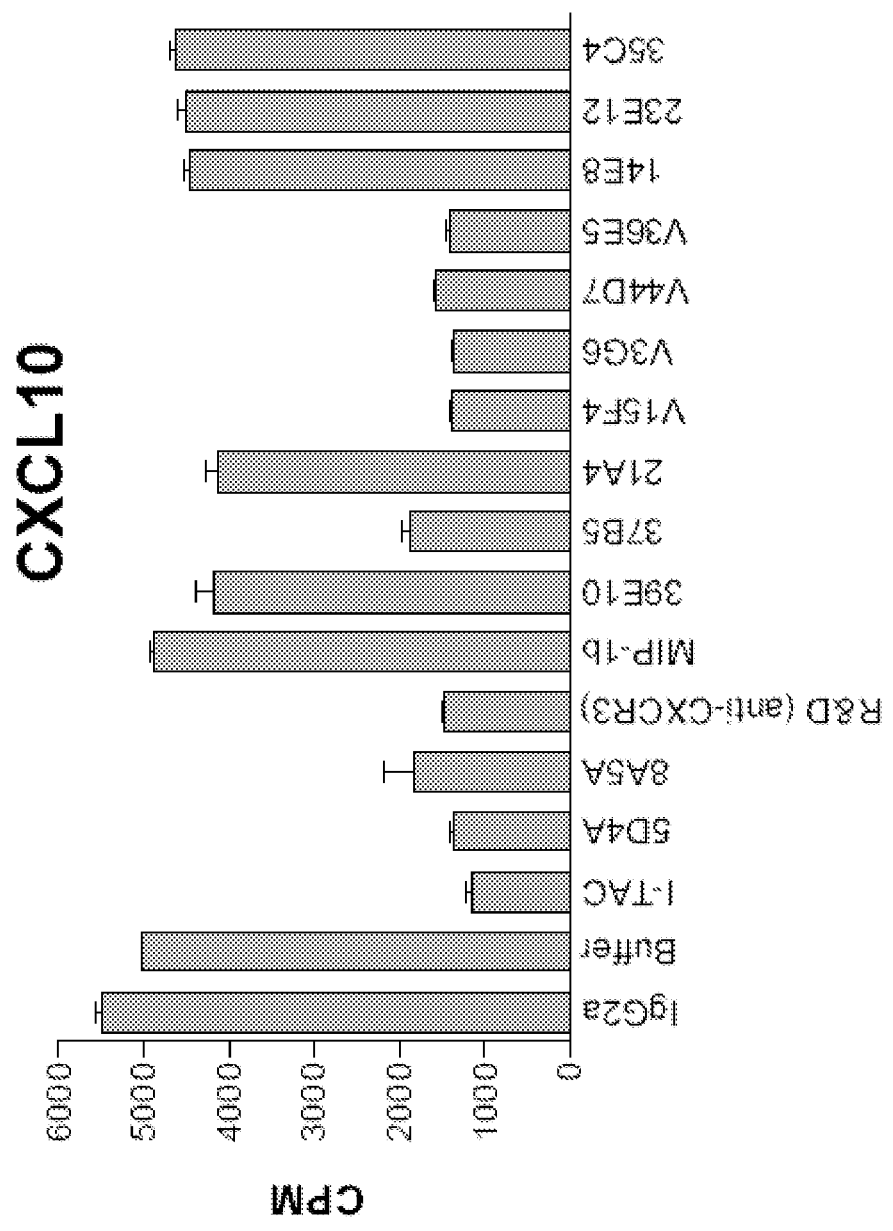
FIG. 19 illustrates inhibition of $^{125}$I-CXCL10 binding to Th1 by CXCR3mAb hybridoma supernatants. Th1 cells were incubated in a 96 well plate with $^{125}$I-CXCL10 in the absence or presence of various CXCRmAb hybridoma supernatants for 1 hr at RT. Cell bound $^{125}$I-ligands were separated from free radioactivity by an oil column and counted using a gamma counter. Seven hybridoma supernatants that inhibited CXCL10 binding to Th1 cells were selected for further development.

Binding affinity of mouse CXCR3 antibodies to CXCR3 was determined by direct saturation binding assay using Europium labeled mouse CXCR3 antibodies. An example of this assay using one mouse CXCR3mAb is shown in FIG. 17. Data from this study indicated that Eu-CXCR3mAb binding to CXCR3 was specific and saturable with binding affinity of subnanomolar Kd (0.47 nM).

Antibody Specificity

Figure 3:
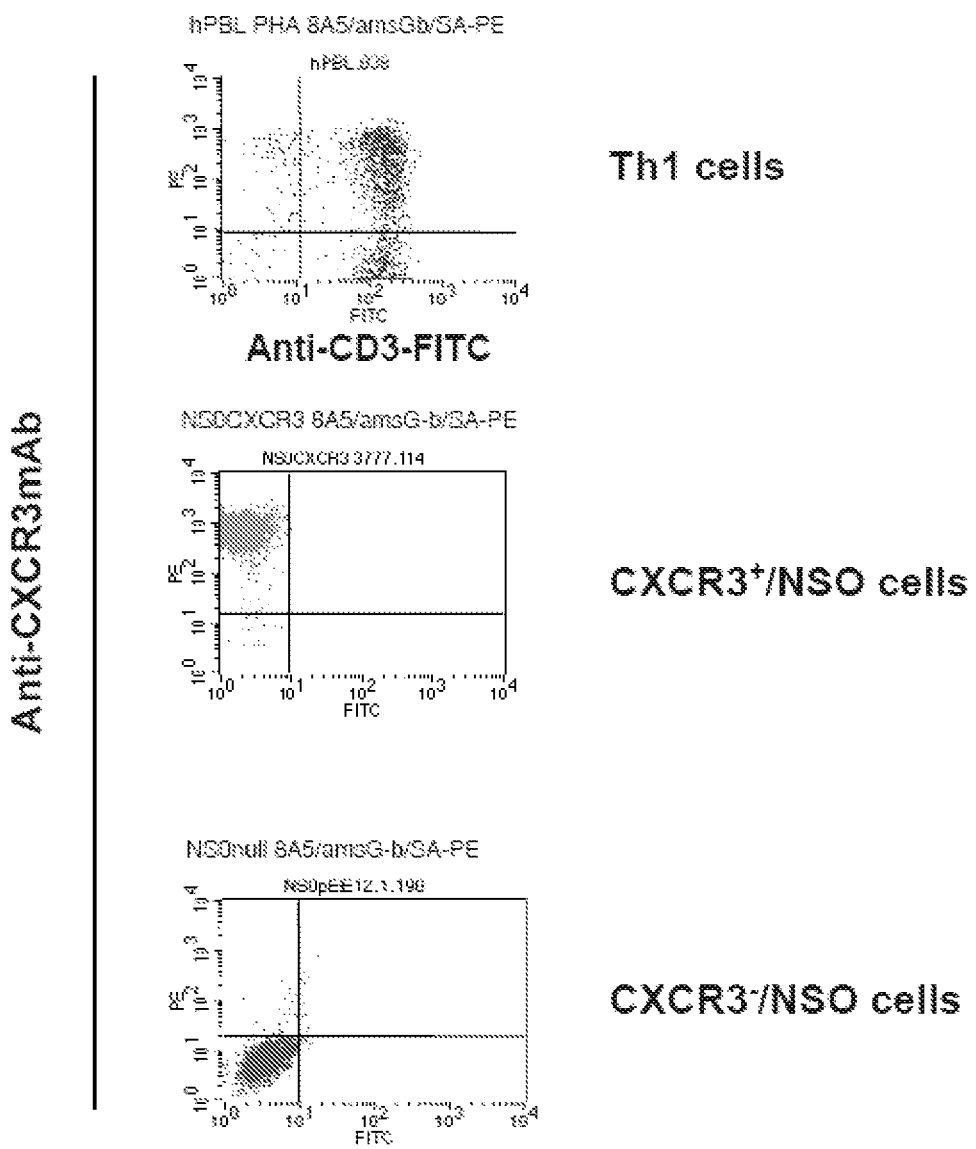
FIG. 3 illustrates a FACs analysis of murine anti-CXCR3mAb binding to Th1 cells (top panel), CXCR3+/NSO cells (middle panel), and CXCR-/NSO cells (bottom panel).
Figure 4:
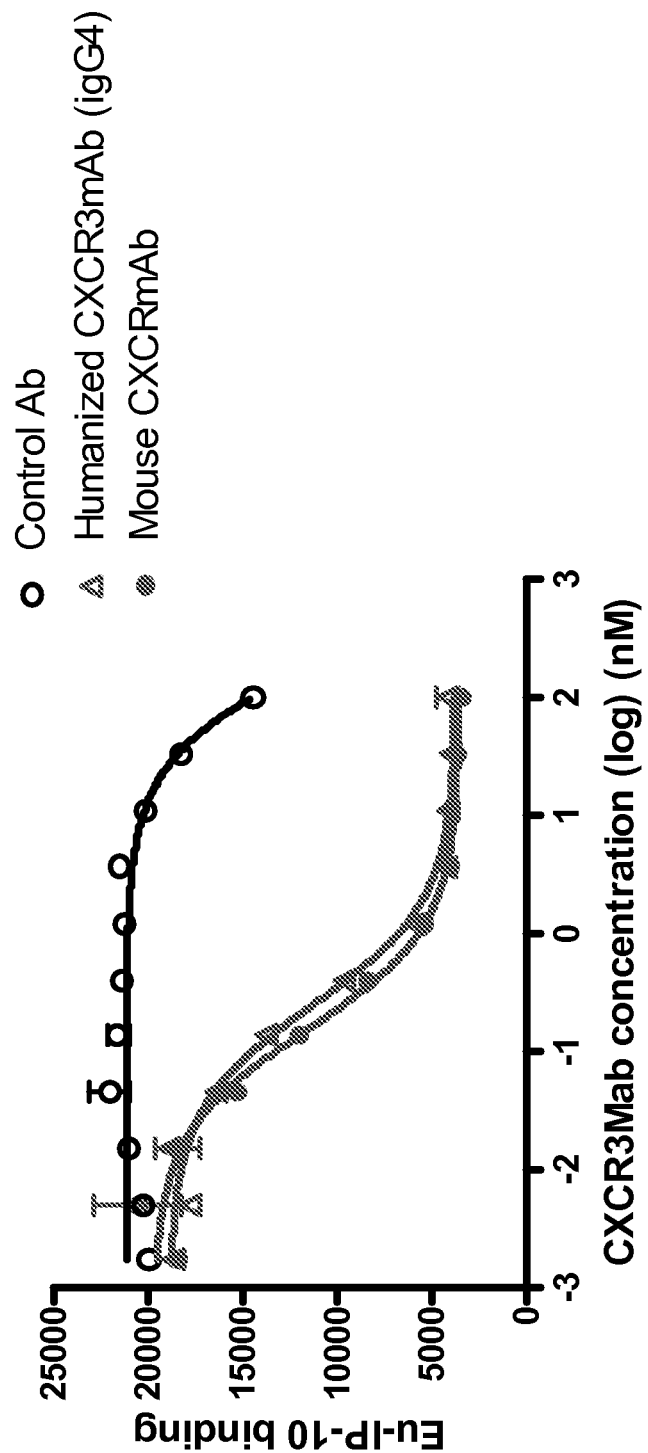
FIG. 4 illustrates inhibition of chemokine binding to CXCR3 by murine anti-CXCR3mAb and humanized anti-CXCR3mAb.
Figure 5:
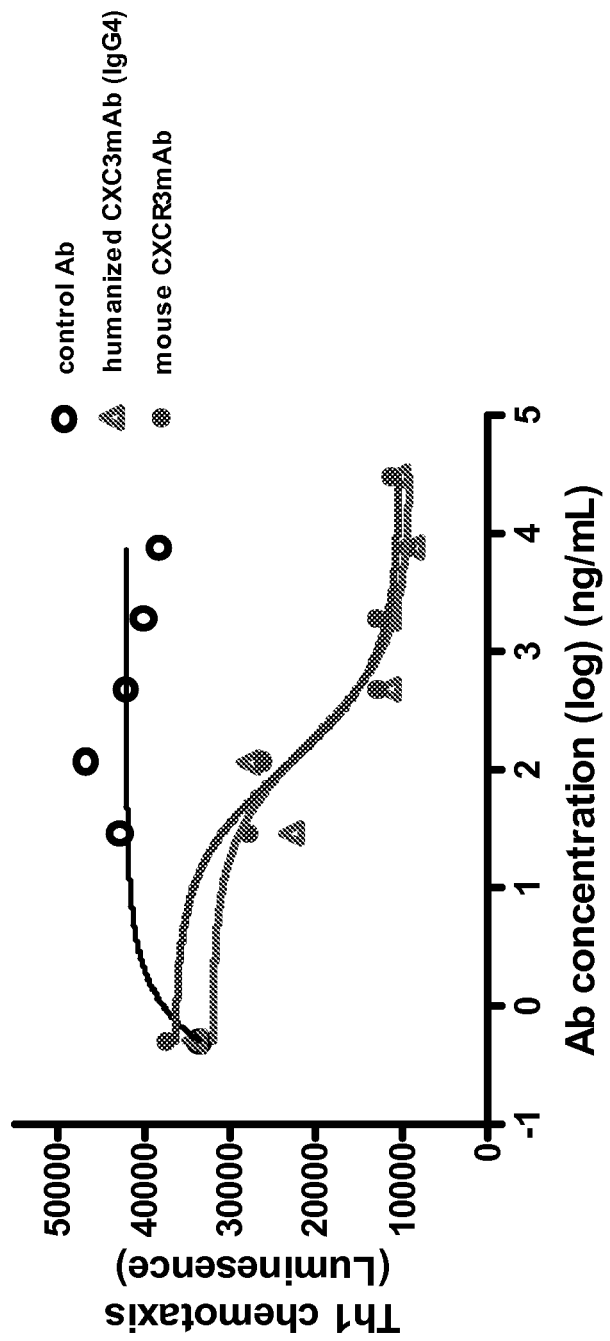
FIG. 5 illustrates inhibition of chemokine mediated chemotaxis by murine anti-CXCR3mAb and humanized anti-CXCR3mAb.
Figure 6:
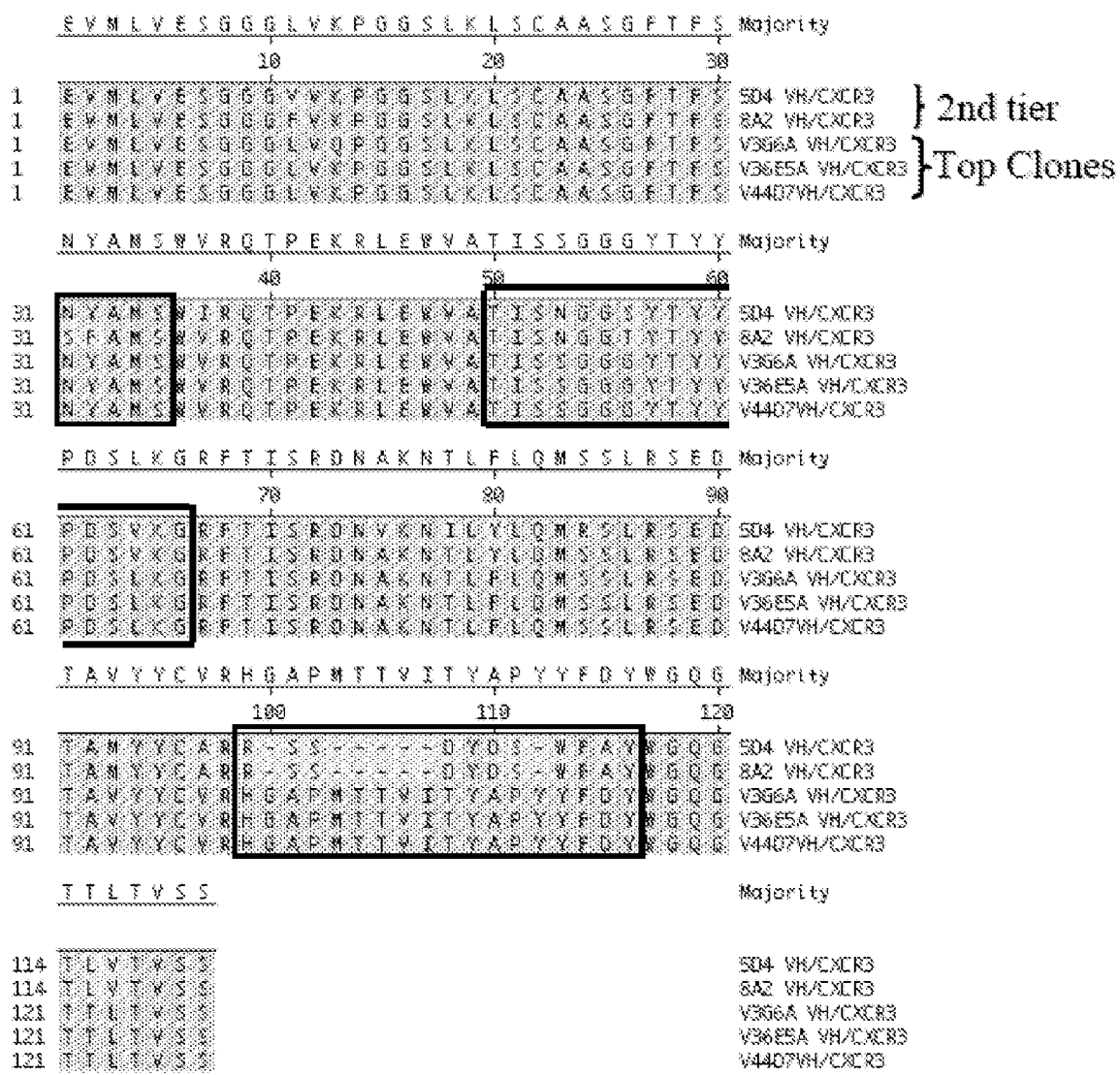
FIG. 6 illustrates an alignment of the VH Domains of 5 anti-CXCR3 Clones (SEQ ID NOS 70-72, 51 and 51, respectively, in order of appearance. The Majority sequence is disclosed as SEQ ID NO: 73).
Figure 9:
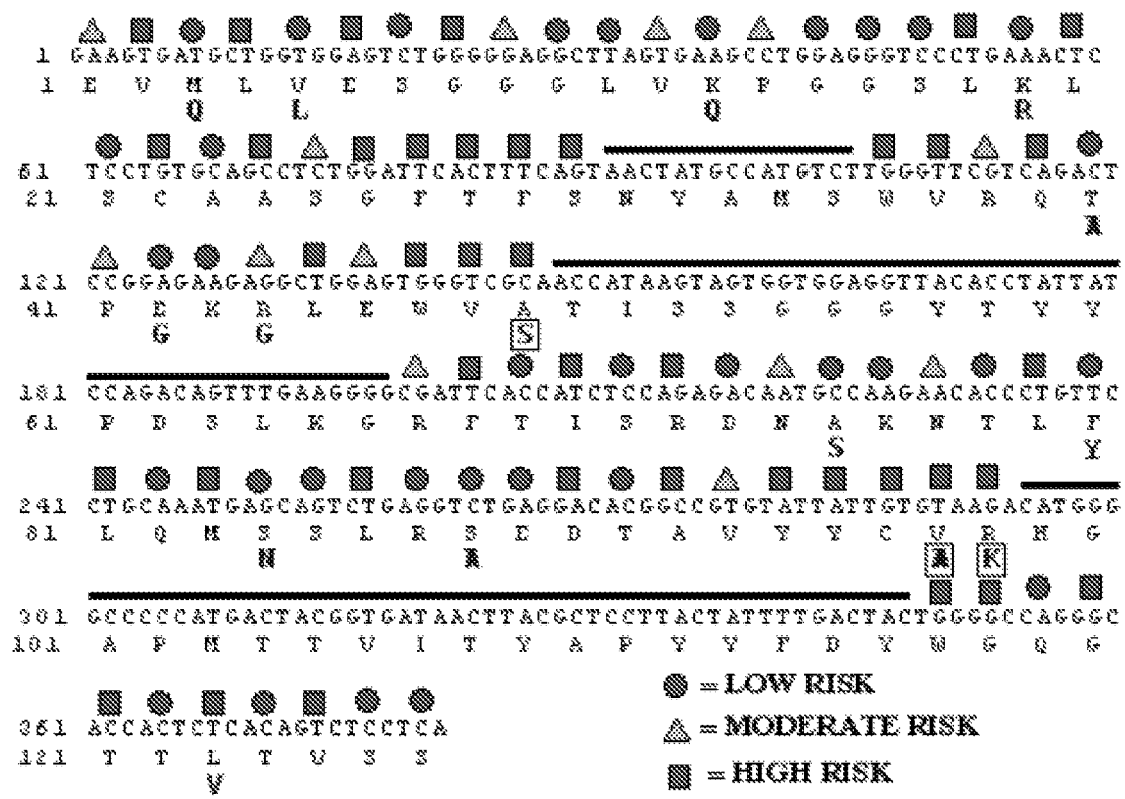
FIG. 9 illustrates the risk assessment of amino acid changes required for complete humanization of the VH domain of anti-CXCR3 clone V44D7. The required amino acid changes are indicated below the main sequence and were derived from an alignment to human VH3-23. The germline gene and an expressed antibody are described in GenBank accession no. AAD53829. The nucleotide sequence disclosed as SEQ ID NO: 50 and the amino acid sequence disclosed as SEQ ID NO: 79.
Figure 12:
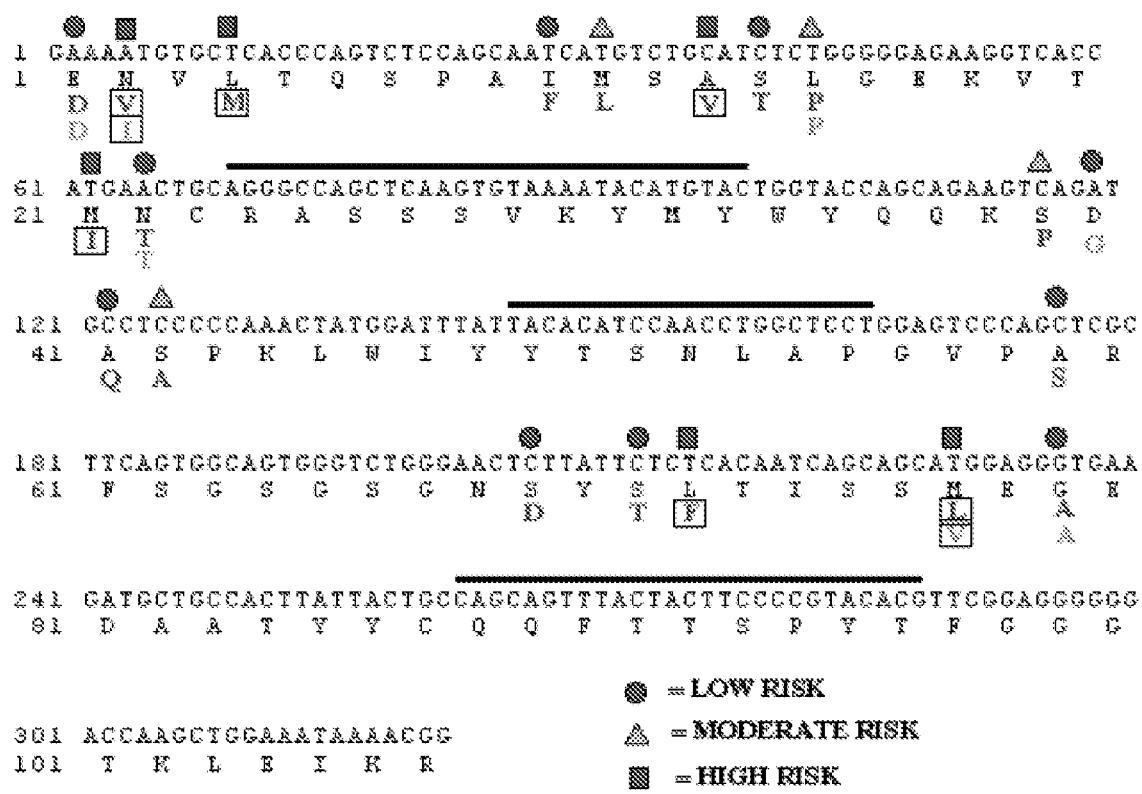
FIG. 12 illustrates the risk assessment of amino acid changes required for complete humanization of the VK domain of anti-CXCR3 clone V3G6. Nucleotide sequence disclosed as SEQ ID NO: 52 and amino acid sequence disclosed as SEQ ID NO: 83.

Mouse antibody hybridomas (20000) were screened by a differential screening assay with CXCR3$^+$ and CXCR3-NSO membranes using a Eu-secondary antibody (DELFIA). Antibodies (~2000) that bound to CXCR3$^+$ membranes were further tested by FACS using CXCR3$^+$/CXCR3$^-$ NSO and Th1 cells. An example for specific binding of CXCR3mAb to CXCR3 expressing cells is shown in FIG. 3.

Species Cross Reactivity

Figure 20:
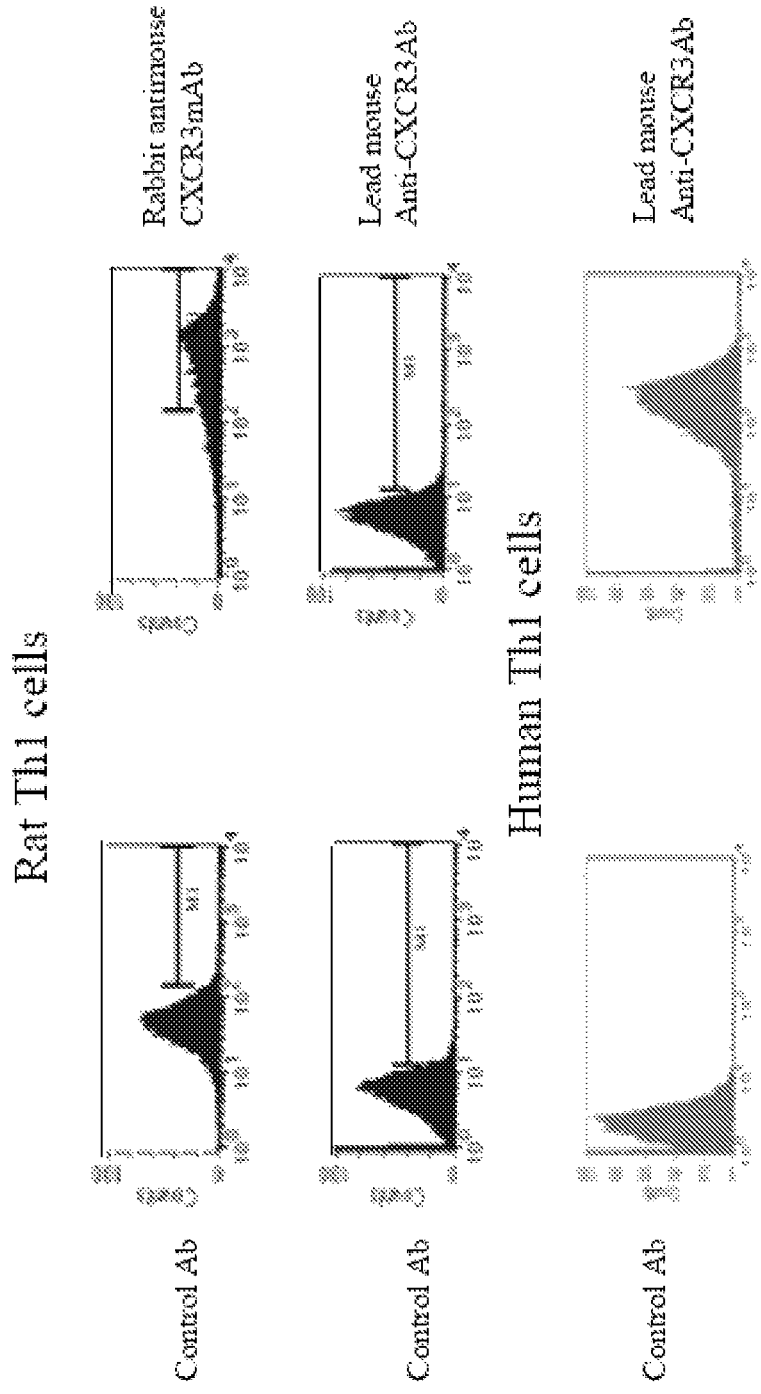
FIG. 20 illustrates that Mouse CXCR3mAb does not cross react with rat Th1 cells. FACS analysis was performed to determine reactivity of mouse CXCR3mAb to polarized rat Th1 cells. Only rabbit anti-mouse CXCR3 Ab bound to rat Th1 cells. Mouse anti-human CXCR3Ab did not bind to rat Th1 cells. As a control, mouse anti-CXCR3mAb binding to human Th1 cells is also shown (bottom panel).

The parental mouse CXCR3mAb was tested for binding to polarized rat Th1 cells by FACS. Only rabbit anti-mouse CXCR3 Ab (positive control) bound to rat Th1 cells. The mouse parental CXCR3mAb did not bind to rat Th1 cells as shown in FIG. 20.

Biological Activity

Binding assay: CXCR3mAb specifically inhibited 125I-labeled IP-10 and -I-Tac binding to primary Th1 cells. Due to unavailability of labeled Mig, it was not tested in binding assays. Chemotaxis assay: CXCR3mAb inhibited Th1 cell migration mediated by CXCR3 chemokines.

Figure 21:
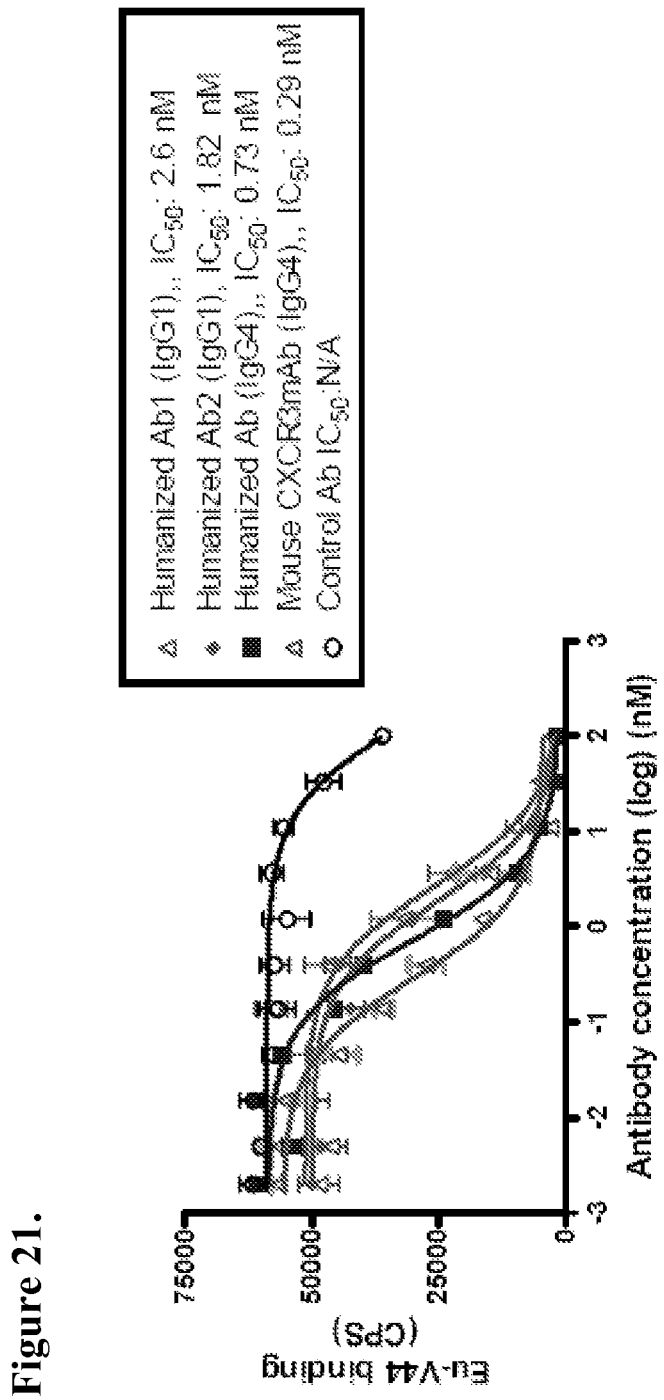
FIG. 21 illustrates inhibition Eu-CXCR3mAb by humanized CXCR3Abs. Th1 cells were incubated in a 96 well plate with Eu-CXCR3mAb in the absence or presence of various concentrations humanized CXCRmAbs. After incubation (1 hr at RT), cell bound Eu-CXCR3mAb was separated from free Europium by washing three times and the plate was read using Vctor2 fluorometer. IC$_{50}$ values were calculated using Prizm software. Ab1 has a heavy chain sequence of humanized anti-CXCR3 V44D7 VH Lead #5 amino acid and a light chain sequence of humanized anti-CXCR3 V44D7 VK Lead #1 (see Informal Sequence Listing) in an IgG1 backbone. Ab2 has a heavy chain sequence of humanized anti-CXCR3 V44D7 VH Lead #5 and a light chain sequence of humanized anti-CXCR3 V44D7 VK Lead #7 (see Informal Sequence Listing) in an IgG1 backbone. Humanized Ab (IgG4) has a heavy chain sequence of humanized anti-CXCR3 V44D7 VH Lead #5 and a light chain sequence of the original mouse anti-CXCR3 V44D7 VK in an IgG4 backbone.
Figure 22:
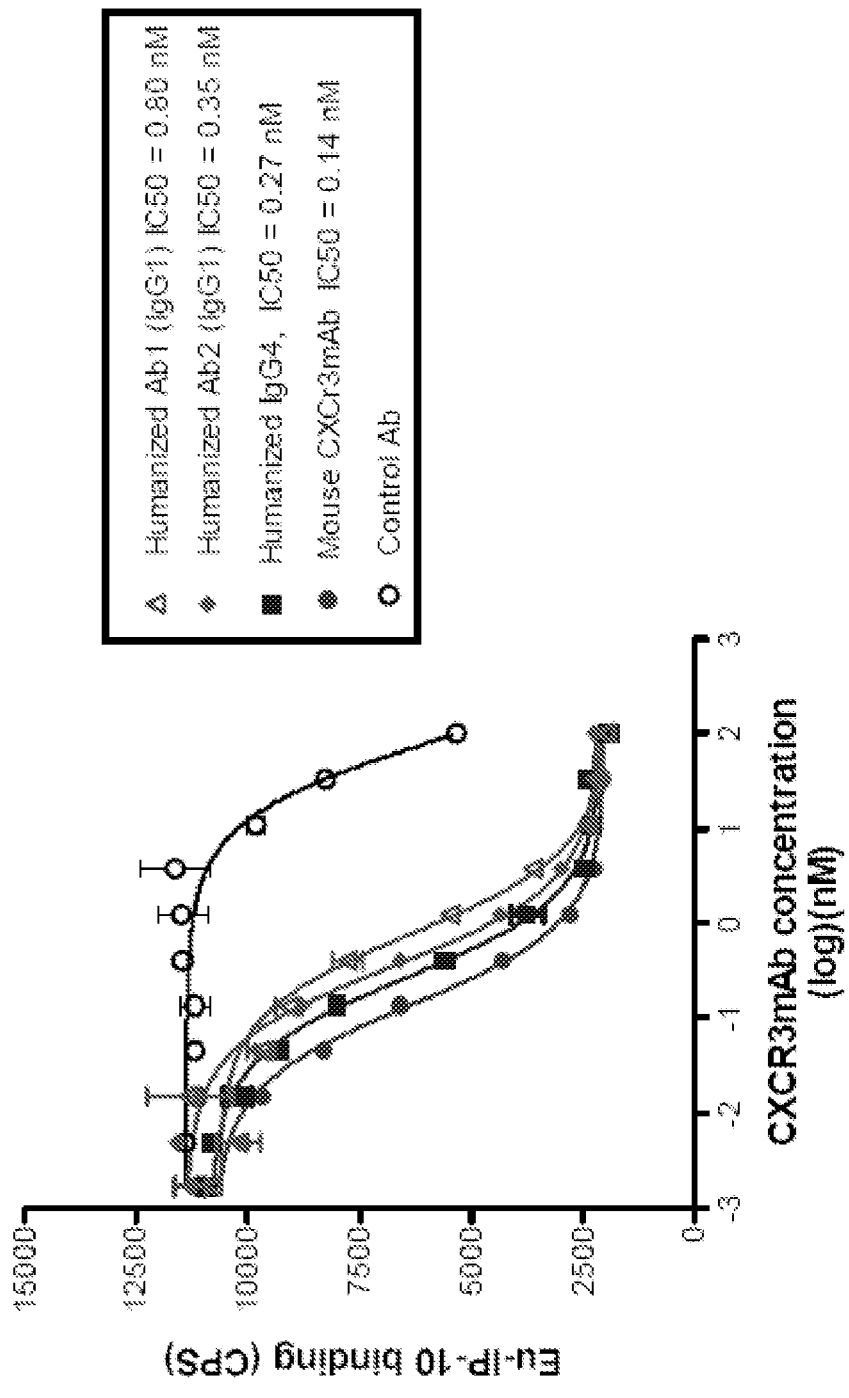
FIG. 22 illustrates inhibition Eu-CXC10 by humanized CXCR3Abs. Th1 cells were incubated in a 96 well plate with Eu-CXCL10 in the absence or presence of various concentrations humanized CXCRmAbs. After incubation (1 hr at RT), cell bound Eu-CXCL10 was separated from free Europium by washing three times and the plate was read using Vctor2 fluorometer. IC$_{50}$ values were calculated using Prizm software.
Figure 23:
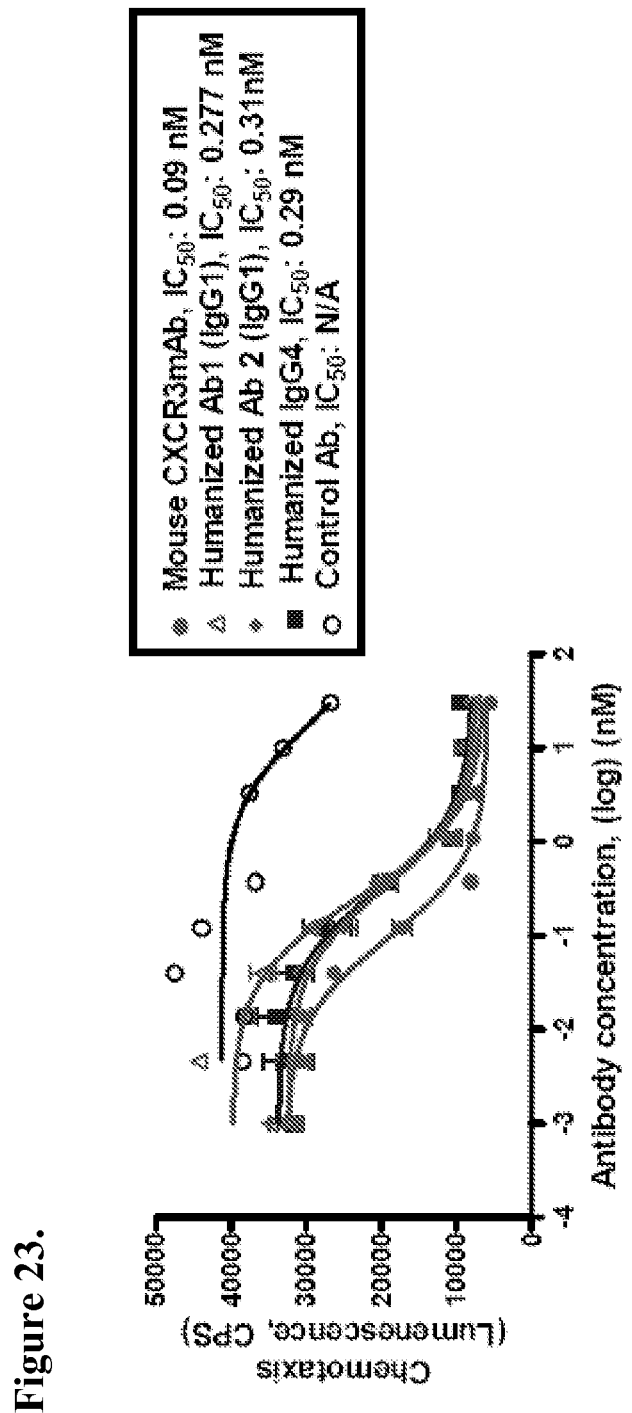
FIG. 23 illustrates inhibition CXCL10-induced Th1 cell chemotaxis by humanized CXCR3Abs. Chemotaxis assay was performed in a ChemoTx 96-well plate (Neuro Probe, Inc). Approximately 29 µL of CXCL10 or buffer control was added to the bottom wells. 25 µL of Th1 cell suspension in the absence or presence of various concentrations of humanized antibodies was added directly on the wells of the filter. After 2 hr incubation at 37° C., cells migrated to the bottom wells were determined by cell titer glo method (Promega).

Humanized antibodies were tested by binding and chemotaxis assays. The results of an Eu-CXCRmAb competitive binding assay are shown in FIG. 21. The results of the Eu-CXCL10 binding assay are shown in FIG. 22. The results of the Th1 chemotaxis assay are shown in FIG. 23.

Mouse Antibody Tested for Agonism of the CXCR3 Receptor

Figure 24:
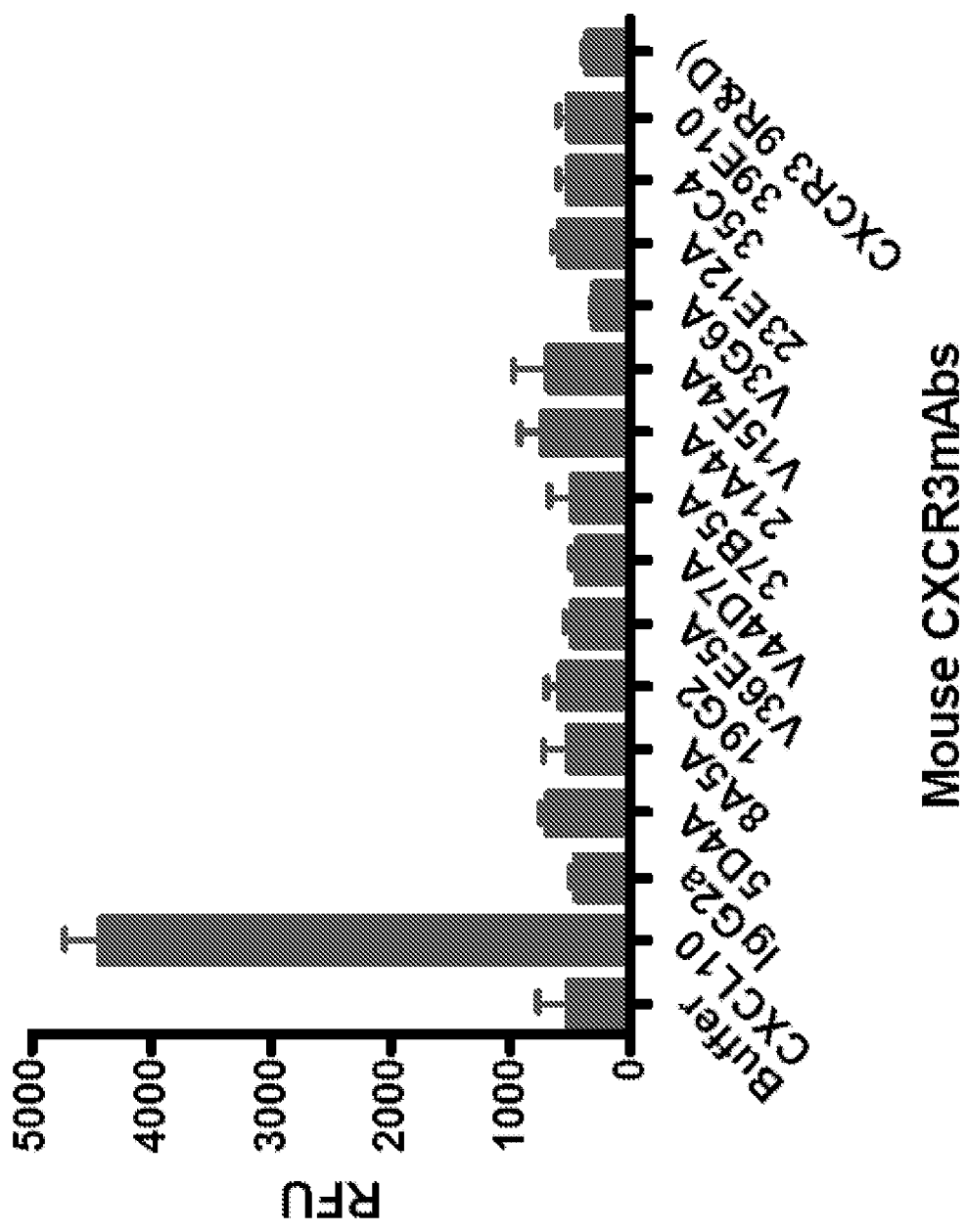
FIG. 24 illustrates an analysis of $Ca^{++}$ flux in Th1 cells. Th1 cells were loaded with Fluo-4,AM (Molecular Probes) and stimulated with various mouse CXCR3mAb antibodies as indicated. Increase in intracellular $Ca^{++}$ was determined FLIPR.

Mouse CXCR3mAbs were tested for agonistic activity in inducing ca mobilization in Th1 cells. As shown in FIG. 24, none of the antibodies s showed any agonistic activity in inducing Ca$^{++}$ flux.

TABLE 2

IC$_{50}$ Values of Different Humanized Antibodies As Determined From Binding and Chemotaxis Assays

| Antibody ID | Binding Assay, IC$_{50}$ (nM) Eu-IP-10 | Binding Assay, IC$_{50}$ (nM) Eu-V44 | Chemotaxis IC$_{50}$ (nM) | Percent Humanization H | Percent Humanization L |
|---|---|---|---|---|---|
| Mouse anti-CXCR3 V44D7 | 0.14 | 0.29 | 0.09 | 88 | 79 |
| Humanized Ab1 H5K1 | 0.8 | 2.6 | 0.31 | 100 | 96 |
| Humanized Ab2 H5K7 | 0.35 | 1.82 | 0.28 | 100 | 94 |
| Humanized Ab3 H5K2 | 1.25 | 1.86 | N.D. | 100 | 100 |
| Humanized Ab4 H5K3 | 0.38 | 0.56 | N.D. | 100 | 100 |
| Humanized Ab5 H5K4 | 0.69 | 1.49 | N.D. | 100 | 100 |
| Humanized Ab6 H5K5 | 0.42 | 0.65 | N.D. | 100 | 100 |

N.D. = not determined

In Table 2, Ab1 has a heavy chain sequence of humanized anti-CXCR3 V44D7 VH Lead #5 amino acid and a light chain sequence of humanized anti-CXCR3 V44D7 VK Lead #1 (see Informal Sequence Listing) in an IgG1 backbone. Ab2 has a heavy chain sequence of humanized anti-CXCR3 V44D7 VH Lead #5 and a light chain sequence of humanized anti-CXCR3 V44D7 VK Lead #7 (see Informal Sequence Listing) in an IgG1 backbone. Ab3 has a heavy chain sequence of humanized anti-CXCR3 V44D7 VH Lead #5 amino acid and a light chain sequence of humanized anti-CXCR3 V44D7 VK Lead #2 (see Informal Sequence Listing) in an IgG1 backbone. Ab4 has a heavy chain sequence of humanized anti-CXCR3 V44D7 VH Lead #5 and a light chain sequence of humanized anti-CXCR3 V44D7 VK Lead #3 (see Informal Sequence Listing) in an IgG1 backbone. Ab5 has a heavy chain sequence of humanized anti-CXCR3 V44D7 VH Lead #5 amino acid and a light chain sequence of humanized anti-CXCR3 V44D7 VK Lead #4 (see Informal Sequence Listing) in an IgG1 backbone. Ab6 has a heavy chain sequence of humanized anti-CXCR3 V44D7 VH Lead #5 and a light chain sequence of humanized anti-CXCR3 V44D7 VK Lead #5 (see Informal Sequence Listing) in an IgG1 backbone.

What is claimed is:

1. An antigen-binding polypeptide that binds specifically to CXCR3, comprising:
   (a) a humanized antibody heavy chain variable region comprising:
      (1) a CDR-H1 comprising the amino acid sequence of SEQ ID NO: 25;
      (2) a CDR-H2 comprising the amino acid sequence of SEQ ID NO: 2; and
      (3) a CDR-H3 comprising the amino acid sequence of SEQ ID NO: 3; and
   (b) a humanized antibody light chain variable region comprising:
      (1) a CDR-L1 comprising the amino acid sequence of SEQ ID NO: 4;
      (2) a CDR-L2 comprising the amino acid sequence of SEQ ID NO: 5; and
      (3) a CDR-L3 comprising the amino acid sequence of SEQ ID NO: 6.

2. The polypeptide of claim 1, wherein:
   (1) the CDR-H1 consists of the amino acid sequence of SEQ ID NO: 25;
   (2) the CDR-H2 consists of the amino acid sequence of SEQ ID NO: 2;
   (3) the CDR-H3 consists of the amino acid sequence of SEQ ID NO: 3;
   (4) the CDR-L1 consists of the amino acid sequence of SEQ ID NO: 4;
   (5) the CDR-L2 consists of the amino acid sequence of SEQ ID NO: 5; and
   (6) the CDR-L3 consists of the amino acid sequence of SEQ ID NO: 6.

3. The polypeptide of claim 1, wherein:
   (a) the humanized antibody heavy chain variable region comprises the amino acid sequence selected from the group consisting of:
      (i) SEQ ID NO: 47; and
      (ii) SEQ ID NO: 9;
   (b) the humanized antibody light chain variable region comprises the amino acid sequence of:
   SEQ ID NO: 11.

4. The polypeptide of claim 1, wherein the polypeptide is selected from the group consisting of an antibody molecule, a Fab fragment, a Fab' fragment, a F(ab')$_2$ fragment, and an scFv molecule.

5. The polypeptide of claim 4, wherein:
   (a) the polypeptide is an antibody and the antibody is a chimeric antibody comprising a human heavy chain constant region and a human light chain constant region; or
   (b) the polypeptide is an scFv molecule, and the scFv has a formula selected from the group consisting of NH$_2$-L-VH—X—VK—COOH and NH$_2$-L-VK—X—VH—COOH; wherein L is a leader sequence; VH is the humanized antibody heavy chain variable region; X is a linking polypeptide; and VK is the humanized antibody light chain variable region.

6. The polypeptide of claim 5, wherein the antibody is an IgG molecule.

7. The polypeptide of claim 6, wherein the antibody is an IgG1 or IgG4 molecule.

8. The polypeptide of claim 1, conjugated to a cytotoxic agent, a radioactive label, an immunomodulator, a hormone, an enzyme, an oligonucleotide, a photoactive agent, an ultrasound-enhancing agent, a non-radioactive label, or any combination thereof.

9. The polypeptide of claim 1, wherein:
   (a) the polypeptide is an antagonist of CXCR3; or
   (b) the polypeptide is not an agonist of CXCR3.

10. The polypeptide of claim 1, wherein the polypeptide binds to CXCR3 with an affinity constant of at least about $10^6 M^{-1}$.

11. The polypeptide of claim 10, wherein the polypeptide binds to CXCR3 with an affinity constant of at least about $10^7 M^{-1}$.

12. The polypeptide of claim 10, wherein the polypeptide binds to CXCR3 with an affinity constant of at least about $10^8 M^{-1}$.

13. The polypeptide of claim 10, wherein the polypeptide binds to CXCR3 with an affinity constant of at least about $10^9 M^{-1}$.

14. A composition comprising the polypeptide of claim 1 and a carrier.

15. An antigen-binding polypeptide that binds specifically to CXCR3, comprising:
   (a) a humanized antibody heavy chain variable region comprising the amino acid sequence of SEQ ID NO: 9; and
   (b) a humanized antibody light chain variable region comprising the amino acid sequence selected from the group consisting of SEQ ID NO: 11.

16. The polypeptide of claim 15, wherein the polypeptide is selected from the group consisting of an antibody molecule, a Fab fragment, a Fab' fragment, a F(ab')$_2$ fragment, and an scFv molecule.

17. The polypeptide of claim 16, wherein:
   (a) the polypeptide is an antibody, and the antibody is a chimeric antibody comprising a human heavy chain constant region and a human light chain constant region; or (b) the polypeptide is an scFv molecule, and the scFv has a formula selected from the group consisting of NH$_2$-L-VH—X—VK—COOH and NH$_2$-L-VK—X—VH—COOH; wherein L is a leader sequence; VH is the humanized antibody heavy chain variable region; X is a linking polypeptide; and VK is the humanized antibody light chain variable region.

18. The polypeptide of claim 17, wherein the antibody is an IgG molecule.

19. The polypeptide of claim 18, wherein the antibody is an IgG1 or IgG4 molecule.

20. The polypeptide of claim 15, conjugated to a cytotoxic agent, a radioactive label, an immunomodulator, a hormone, an enzyme, an oligonucleotide, a photoactive agent, an ultrasound-enhancing agent, a non-radioactive label, or any combination thereof.

21. The polypeptide of claim 15, wherein the polypeptide binds to CXCR3 with an affinity constant of at least about $10^6 M^{-1}$.

22. The polypeptide of claim 21, wherein the polypeptide binds to CXCR3 with an affinity constant of at least about $10^7 M^{-1}$.

23. The polypeptide of claim 21, wherein the polypeptide binds to CXCR3 with an affinity constant of at least about $10^8 M^{-1}$.

24. The polypeptide of claim 21, wherein the polypeptide binds to CXCR3 with an affinity constant of at least about $10^9 M^{-1}$.

25. A composition comprising the polypeptide of claim 15 and a carrier.

* * * * *

UNITED STATES PATENT AND TRADEMARK OFFICE
CERTIFICATE OF CORRECTION

| | | |
|---|---|---|
| PATENT NO. | : 8,435,522 B2 | Page 1 of 1 |
| APPLICATION NO. | : 12/449222 | |
| DATED | : May 7, 2013 | |
| INVENTOR(S) | : Smith et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 845 days.

Signed and Sealed this
Second Day of December, 2014

Michelle K. Lee
*Deputy Director of the United States Patent and Trademark Office*